US012605257B2

(12) United States Patent
    Mansmann

(10) Patent No.:  US 12,605,257 B2
(45) Date of Patent:      Apr. 21, 2026

(54) INSTRUMENTS AND METHODS FOR PREPARING PATIENT RECIPIENT SITE AND INSTALLING MEDICAL IMPLANT

(71) Applicant: FORMAE, INC., Paoli, PA (US)

(72) Inventor: Kevin A Mansmann, Paoli, PA (US)

(73) Assignee: FORMAE, INC., Paoli, PA (US)

( * ) Notice: Subject to any disclaimer, the term of this patent is extended or adjusted under 35 U.S.C. 154(b) by 259 days.

(21) Appl. No.: 18/259,191

(22) PCT Filed: Dec. 22, 2021

(86) PCT No.: PCT/US2021/064895
    § 371 (c)(1),
    (2) Date: Jun. 23, 2023

(87) PCT Pub. No.: WO2022/140564
    PCT Pub. Date: Jun. 30, 2022

(65)            Prior Publication Data
    US 2024/0050243 A1      Feb. 15, 2024

Related U.S. Application Data

(60) Provisional application No. 63/130,206, filed on Dec. 23, 2020.

(51) Int. Cl.
    *A61F 2/46*        (2006.01)
    *A61B 17/17*       (2006.01)
    *A61F 2/30*        (2006.01)
(52) U.S. Cl.
    CPC ........ *A61F 2/4618* (2013.01); *A61B 17/1764* (2013.01); *A61F 2002/30759* (2013.01); *A61F*

*2002/4632* (2013.01); *A61F 2002/4635* (2013.01); *A61F 2002/4677* (2013.01)

(58) Field of Classification Search
    CPC ........................... A61B 17/1764; A61F 2/4618
    See application file for complete search history.

(56)            References Cited

U.S. PATENT DOCUMENTS

| | | | |
|---|---|---|---|
| 5,891,150 A | 4/1999 | Chan | |
| 8,814,871 B2 | 8/2014 | Mansmann | |
| 8,814,914 B2 | 8/2014 | Miller | |
| 8,864,768 B2 | 10/2014 | Hanson et al. | |
| 2003/0130666 A1 | 7/2003 | Whittaker | |
| 2009/0240253 A1 | 9/2009 | Murray | |
| 2009/0318746 A1 | 12/2009 | Thurmond, II | |
| 2011/0125159 A1 | 5/2011 | Hanson et al. | |
| 2016/0287392 A1 | 10/2016 | Patrick et al. | |
| 2018/0153564 A1* | 6/2018 | Cunningham | ........ A61F 2/0811 |
| 2018/0289493 A1 | 10/2018 | Mansmann | |
| 2020/0375668 A1 | 12/2020 | Pandya | |
| 2022/0409379 A1 | 12/2022 | Mansmann | |

FOREIGN PATENT DOCUMENTS

| | | |
|---|---|---|
| CN | 108289733 A | 7/2018 |
| EP | 0739185 B1 | 9/2004 |
| GB | 2454325 A | 5/2009 |

* cited by examiner

*Primary Examiner* — Andrew Yang
(74) *Attorney, Agent, or Firm* — Volpe Koenig

(57)            ABSTRACT

A surgical tool assembly is disclosed herein. The assembly includes a first guide tool portion configured to support an instrument. The first guide tool portion is configured to limit movement of the instrument relative to a patient site. A second guide tool portion is provided that is configured to receive at least one K-wire to stabilize the surgical tool assembly.

15 Claims, 73 Drawing Sheets

TABLE 1

| KNEE FEMORAL CONDYLE | | | | | |
|---|---|---|---|---|---|
| CAM ZONE - JOINT SURFACE CURVE RADIUS | | | | | |
| P POSTERIOR | MP MID-POSTERIOR | D DISTAL | MA MID-ANTERIOR | A ANTERIOR |
| 18+ | 22 | 25 | 28 | 32+ |
| 18+ | 22 | 25 | 28 | 32+ |
| 18+ | 22 | 25 | 28 | 32+ |

18

18'

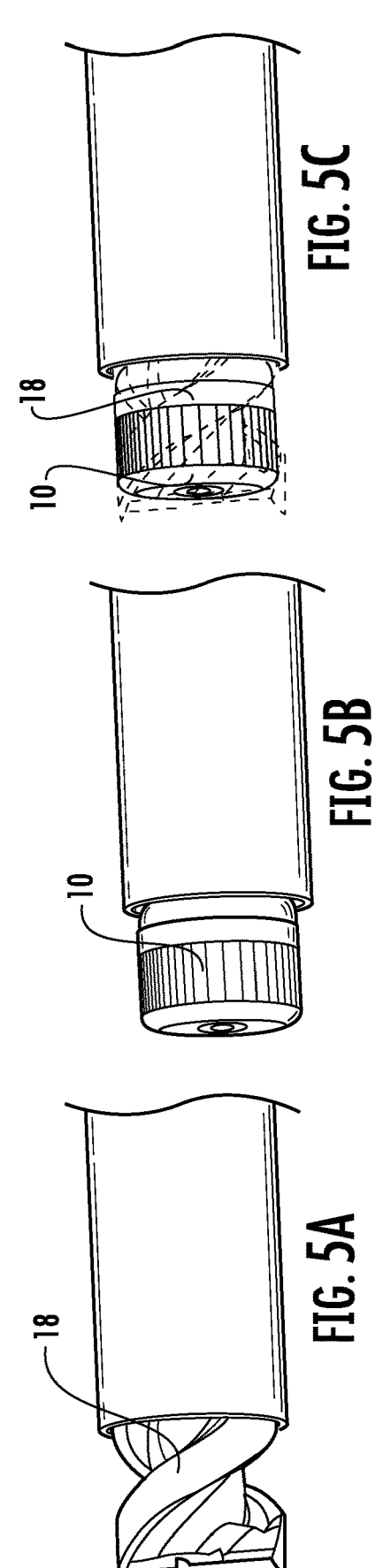
FIG. 5C
FIG. 5B
FIG. 5A
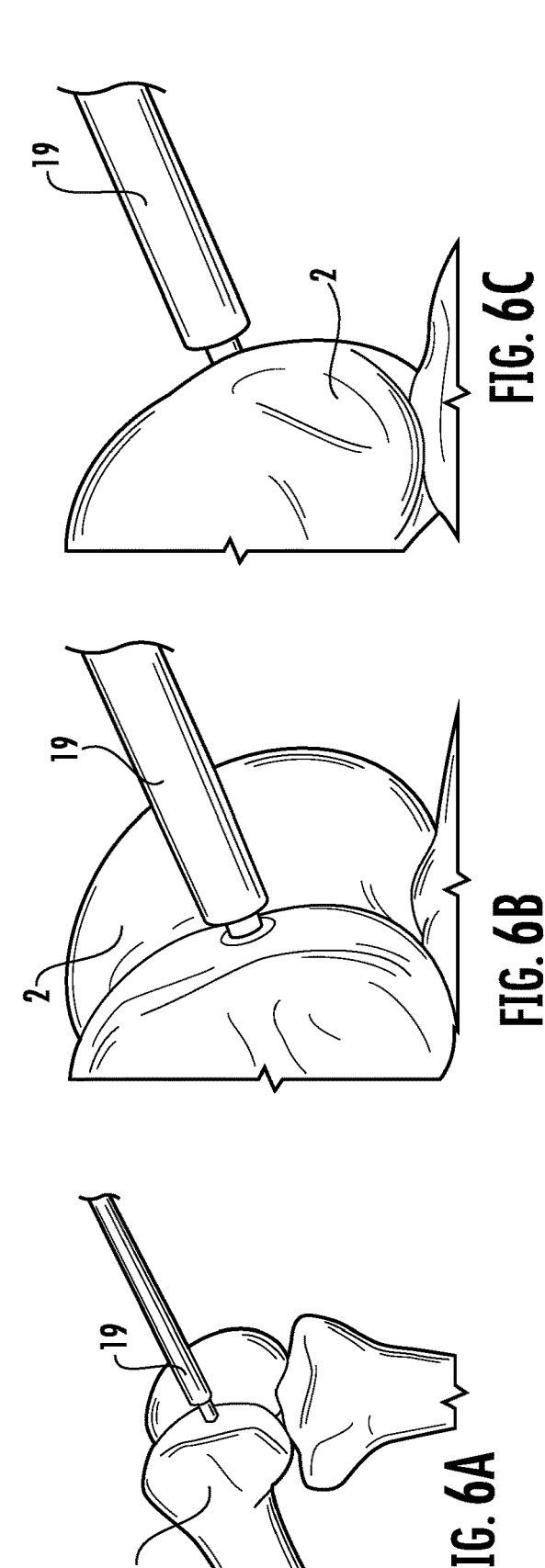
FIG. 6C
FIG. 6B
FIG. 6A

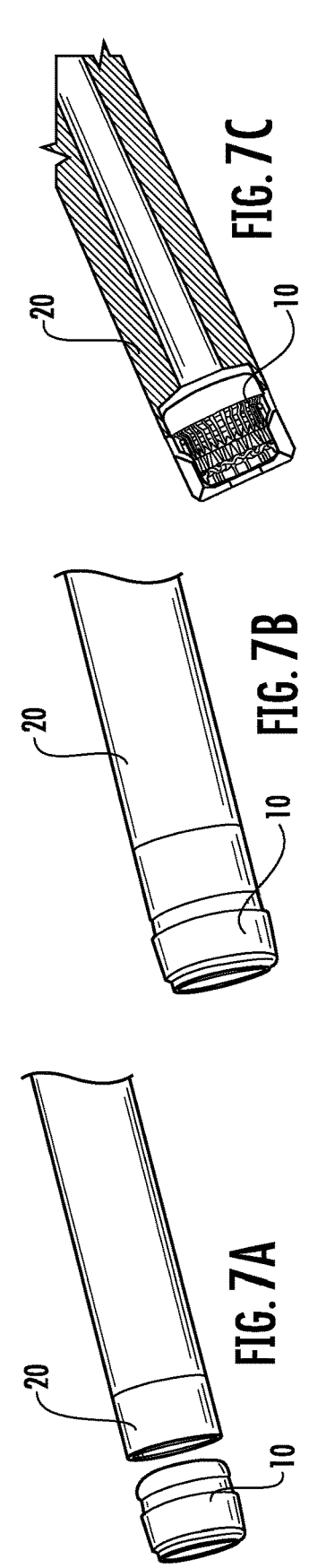
FIG. 7C
FIG. 7B
FIG. 7A
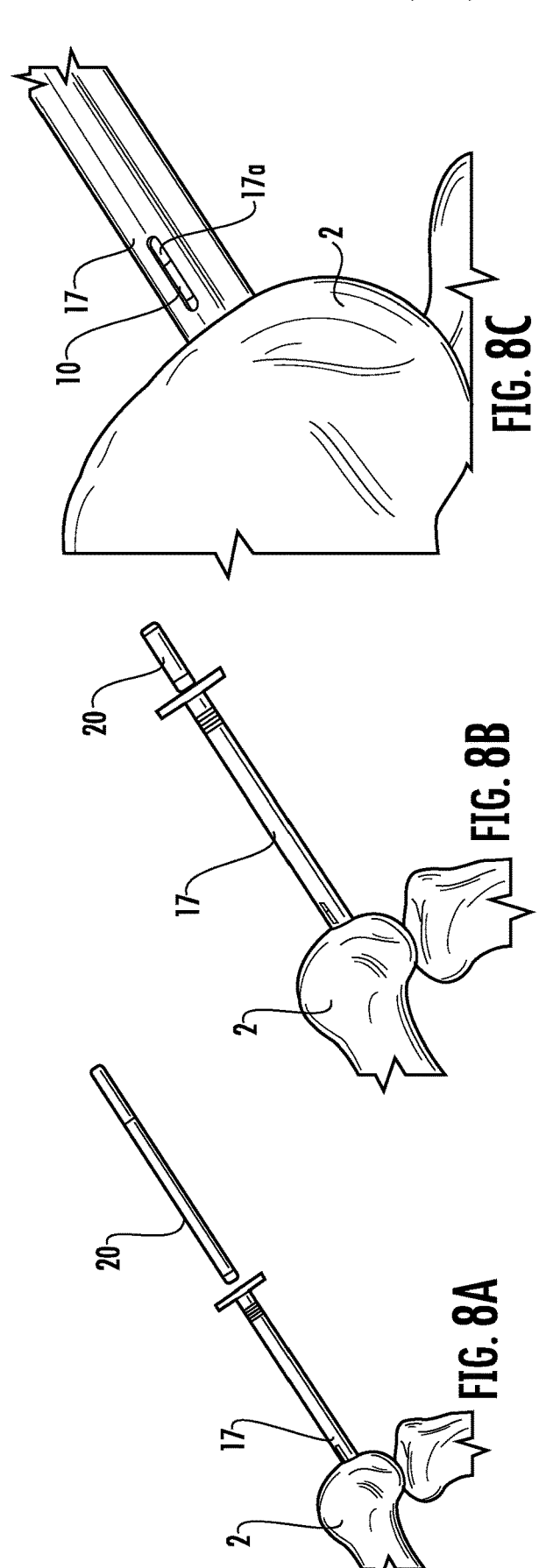
FIG. 8C
FIG. 8B
FIG. 8A

25

37a

37c

38

101

101c

101b

102

103

103a

INSTRUMENTS AND METHODS FOR PREPARING PATIENT RECIPIENT SITE AND INSTALLING MEDICAL IMPLANT

INCORPORATION BY REFERENCE

This application is a national stage entry of International Application No. PCT/US2021/064895, filed on Dec. 22, 2021, which claims the benefit of U.S. Provisional Patent Application 63/130,206, filed on Dec. 23, 2020, the contents of all of which are incorporated herein by reference as if fully set forth herein.

FIELD OF INVENTION

This disclosure relates to surgical instruments for preparing bone recipient sites for implants and also installing the implants in the recipient sites. The instruments described herein are configured to enable the machining of bone, with limited direct access, in preparation for the installation of a medical device, such as an implant. Specifically, this disclosure pertains to the preparation of the bone under the damaged cartilage articular surface of a mammalian synovial joint.

BACKGROUND

As explained in US Patent Pub. 2018/0289493, which is incorporated by reference as if fully set forth herein, cartilage is a flexible and relatively soft biological material that generally protects relatively hard bone, especially in the area of joints where bone is likely to be contacted by other hard surfaces. Natural cartilage forms a thin layer which covers certain bone surfaces. Over time, cartilage deteriorates and becomes damaged due to use or other conditions. This is especially a problem of hyaline cartilage, a material that is found articulating joints, including knees, hips, and shoulders in humans. For a variety of reasons, such cartilage is not as self-sustaining as other tissues, which leads to a need for repair and/or prosthetic replacement procedures, especially in the elderly. In order to repair these joints, it is known that implants can be installed to replace a portion of the bearing surfaces. PCT Application PCT/US2020/063539, which is also owned by the current Applicant (Formae, Inc.), describes one known type of implant, and is also incorporated by reference as if fully set forth herein.

In order to access the sites in need of repair, surgeons must use various tools and instruments. Surgeons generally must machine and prepare the recipient site for a medical implant. In some situations, direct access to the recipient site may be possible. However, in other situations, direct access to the recipient site may not be possible or may be limited.

Accordingly, there is a need for various solutions, such as instruments, surgical tools, and processes, that would provide the ability for a surgeon to engage with the recipient site (i.e. to machine, bore, ream, drill, etc.) regardless of whether direct or indirect access is available.

SUMMARY

As disclosed in the embodiments herein, a guide assembly is generally provided that includes a guide tool (which can be handheld or otherwise manipulated by hand), a cutting guide (which is generally configured to receive a cutting end of a drill), and an alignment and fixation assembly (which may include various components, such as K-wires). In one aspect, a K-wire engages an underside of the cutting guide, and a drill (which is also referred to as a cutting tool) engages a top side of the cutting guide to secure the cutting guide relative to a recipient site. The drill is secured within the cutting guide such that any subsequent cutting, drilling, etc., of the drill is guided, controlled and limited to a predetermined geometry.

In one aspect, a method of preparing an implant site and a system for preparing an implant site are provided. The methods and systems include a guide tool and a cutting tool. In one aspect, the cutting tool comprises a right-angle drill. The guide tool can have a triangular profile when viewed from the side. In one aspect, a cutting guide (also referred to herein as a platform) is dimensioned to be partially arranged within and/or surrounding a recipient site, and the cutting guide is coupled with the cutting tool. The cutting tool can be coupled to the guide tool such that a geometric cutting profile of a cutting end of the cutting tool is restricted via the guide tool.

In one aspect, at least three K-wires are provided for stabilizing the guide tool and/or securing the cutting guide in place. At least two of the K-wires extend approximately parallel to each other, and a third K-wire extends at an angle relative to the two other K-wires.

In one aspect, the cutting guide limits a cutting profile of the cutting tool to a circular profile. The term cutting guide is used herein to refer to any structure or component that limits or restricts movement of the cutting tool.

An alignment guide assembly can be provided on the guide tool that defines a plurality of openings dimensioned to allow K-wires to extend therethrough and fix the assembly in place relative to a patient.

An instrument guide assembly can be provided that includes a bracket slidably secured on a base portion of the guide tool. The base portion of the guide tool can define a track having a predetermined length for the bracket to slide along, and an interface pivotably secured to the bracket and including a channel or receptacle configured to couple with the cutting tool.

The cutting guide can include a flat perimeter configured to sit on or otherwise rest against a worn-out joint surface and stabilized via a flat perimeter edge. In one aspect, the flat perimeter of the cutting guide is coated with or otherwise comprises a hydrogel or soft durometer polymer.

In one aspect, a coupler is configured to attach a cutting end of the cutting tool to a guide arm of the guide tool.

A surgical tool assembly is also disclosed herein. The assembly includes a first guide tool portion configured to support an instrument. The first guide tool portion is configured to limit movement of the instrument relative to a patient site. A second guide tool portion is configured to receive at least one K-wire to stabilize the surgical tool assembly. The first guide tool portion can further comprise an instrument guide assembly configured to engage with a portion of the instrument. The instrument guide assembly can comprise a slider that is slidably secured along a track defined by a base portion of the first guide tool portion, and a support interface configured to engage with the portion of the instrument. The support interface is configured to pivot relative to the slider.

The first guide tool portion can further comprise a first support guide defining a plurality of openings each configured to receive at least one K-wire. The K-wires configured to be received in the first support guide and the second guide tool portion can be configured to be arranged at an oblique angle relative to each other.

The first guide tool portion can further comprise a guide arm including an end defining a first receptacle. The end is configured engage against the patient site, and the first receptacle is configured to constrict movement of an end of the instrument relative to the patient site.

The guide arm can be configured to extend in a tangential direction relative to the patient site. The first guide tool portion can further comprise a second receptacle configured to receive another portion of the instrument. The instrument can include a protrusion configured to project within the second receptacle. The end of the guide arm can be coated with a hydrogel or soft durometer polymer to avoid damaging the patient's anatomy.

An instrument guide can be provided that is configured to receive a terminal end of instrument. The instrument guide can be configured to be engaged by the at least one K-wire received within the second guide tool portion.

The first guide tool portion and the second guide tool portion can be adjustable relative to each other.

The second guide tool portion can be configured to support a cannula dimensioned to receive the at least one K-wire, and the cannula can be configured to engage against a patient's anatomy.

In another aspect, an alignment guide tool is provided that includes a primary body defining at least one opening configured to receive at least one K-wire, a guide interface configured to receive a first portion of an instrument, and a receptacle configured to receive a second portion of the instrument.

The guide interface can be configured to pivot relative to the primary body, and the guide interface is a ring. The receptacle can have a circular profile, i.e. a profile that generally matches the implant. At least one strut can extend from the primary body for stabilization.

A method of engaging an instrument with an implant recipient site using a surgical tool assembly is also disclosed herein. The method includes providing a first guide tool portion comprising an instrument guide assembly and a guide arm defining a first receptacle, and a second guide tool portion configured to receive a K-wire. The method includes aligning the first receptacle with the implant recipient site. The method also includes stabilizing the surgical tool assembly via insertion of at least one K-wire through at least one of the first guide tool portion or the second guide tool portion. The method includes attaching an instrument to the instrument guide assembly, and then maneuvering the instrument relative to the implant recipient site.

The instrument guide assembly is configured to pivot such that the instrument is at least partially rotatable while attached to the instrument guide assembly. The first receptacle is configured to limit movement of a terminal end of the instrument, and the first guide tool portion further comprises a second receptacle configured to engage a protrusion on the instrument to further limit movement of the instrument.

In one aspect, least two K-wires extend through the first guide tool portion and at least one K-wire extends through the second guide tool portion to stabilize the surgical tool assembly.

The present disclosure provides instrumentation to install an improved anchoring system to deliver and securely anchor a hydrogel medical device to replace damaged cartilage in a mammalian joint, using an anchor having a hollow or shelled out interior (i.e. internal cavity), to optimize the secure fixation of the bone anchor to the cartilage replacing hydrogel to enhance the longevity of the connection between the anchor and the hydrogel being anchored.

Additional aspects and embodiments are described herein.

BRIEF DESCRIPTION OF THE DRAWINGS

The foregoing Summary and the following detailed description will be better understood when read in conjunction with the appended drawings, which illustrate a preferred embodiment of the invention. In the drawings:

FIGS. 5A-5C illustrate aspects of a reamer tool in various states.

FIGS. 6A-6C illustrate steps for using a trial implant to check various parameters of a patient recipient site.

FIGS. 7A-7C illustrate an impact tool and an implant according to one aspect.

FIGS. 8A-8C illustrate aspects of a cannula engaged with a patient's anatomy according to one embodiment.

FIG. 9E is a top view of the alignment guide tool and the drill of.

FIG. 9O is a perspective view of the alignment guide tool.

DETAILED DESCRIPTION OF THE PREFERRED EMBODIMENTS

Figures 1A, 1B, 1C, 1D, 1E:
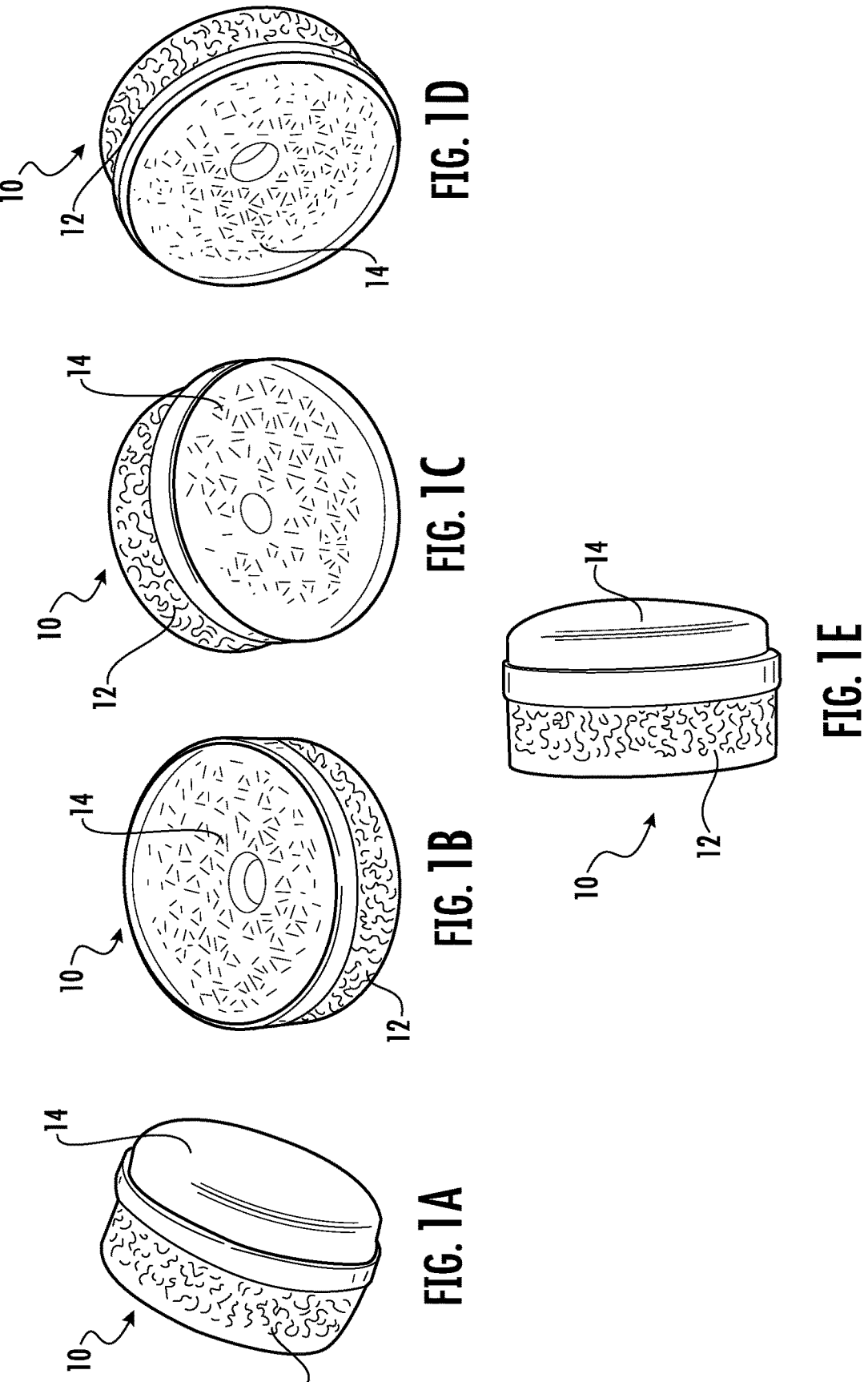
FIGS. 1A-1E are various perspective and side views of a medical implant that is configured to be implanted or installed using various instruments disclosed herein.

The description provided herein is to enable those skilled in the art to make and use the described embodiments set forth. Various modifications, equivalents, variations, combinations, and alternatives, however, will remain readily apparent to those skilled in the art. Any and all such modifications, variations, equivalents, combinations, and alternatives are intended to fall within the spirit and scope of the present invention defined by claims.

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced items unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

Instruments to install medical devices are generally designed corresponding to the medical device being installed. One type of implant includes a round medical implant plug 10 as shown in FIGS. 1A-1E. These implants 10 can be press fit into a round hole prepared in the bone directly under the damaged articular joint surface, similar to a dowel into a corresponding recipient hole. The recipient hole can be precisely made to tolerances that result in a recipient hole which is undersized relative to the medical implant 10 to optimize a stable and secure press fit, such that the bone surrounding the medical implant 10 can grow into the implant 10, such as in connection with a healing process. This healing process is termed osseointegration, in that the healing bone into the porous outer layer of the medical implant effectively integrates the implant with the bone, for permanent fixation of the medical device. The challenge is to do this precisely with only limited access through a minimal incision, at an angle that does not permit direct access to the desired recipient site, ultimately to reduce patient risk, pain, suffering, healing and rehabilitation.

The implant 10 disclosed in FIGS. 1A-1E, which can be used with any of the instruments disclosed herein, can generally include an anchor body 12 defining a cavity, and an elastic articulating element 14 that is secured within the cavity. Attachment features, such as lattice structures, can be provided on the anchor body 12 to secure the elastic articulating element 14 to the anchor body. An outer surface of the sidewall can include a porous structure configured to promote bone ingrowth. Additional features of the implant 10 are disclosed in PCT Application PCT/US2020/063539, the entire contents of which are incorporated by reference herein.

Direct Access Instrumentation

Figure 3:
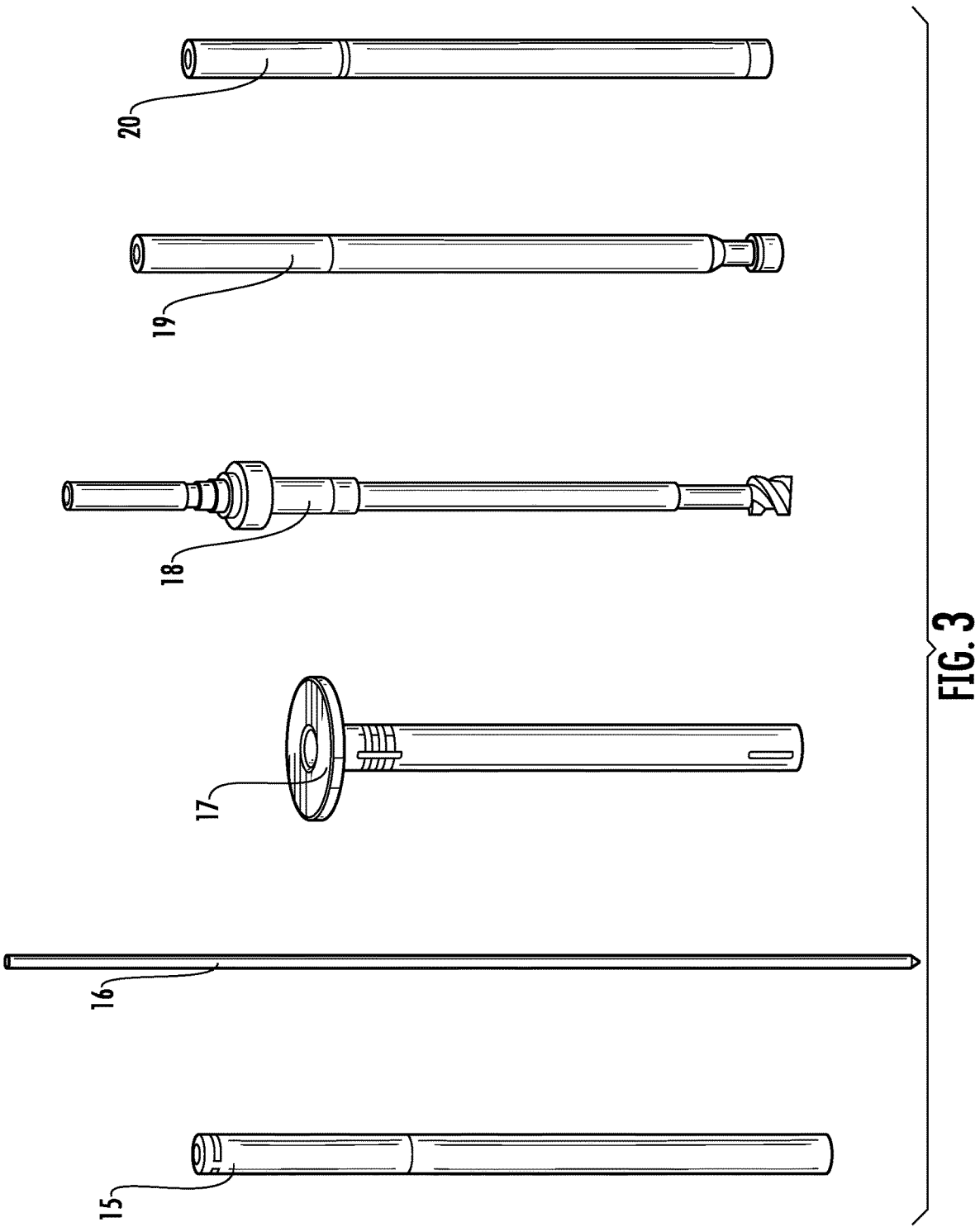
FIG. 3 illustrates an assembly of surgical tools for direct implantation.

The instruments necessary for preparing a recipient site in the bone is dependent upon the surgeon's access to the damaged cartilage surface to be replaced. In one arrangement, the surgeon has direct access, which can be radial or perpendicular, to the joint cartilage surface being replaced. In this situation, the instruments illustrated in FIG. 3 can be used. FIG. 3 illustrates a trocar drill guide 15, which is shown in use in FIG. 4A. FIG. 3 illustrates a K-wire 16, which is shown in use in connection with the trocar drill guide 15 in FIG. 4B. FIG. 3 illustrates a cannula 17, which is shown in use with the trocar drill guide 15 and the K-wire 16 in FIG. 4C. FIG. 3 illustrates a reamer 18, which is shown in use with the trocar drill guide 15, the K-wire 16, and the cannula 17 in FIG. 4D. FIG. 3 illustrates a trial tool 19, which is shown in use in FIGS. 6A-6C. FIG. 3 also illustrates an impactor tool 20, which is described in more detail herein.

Figure 2A:
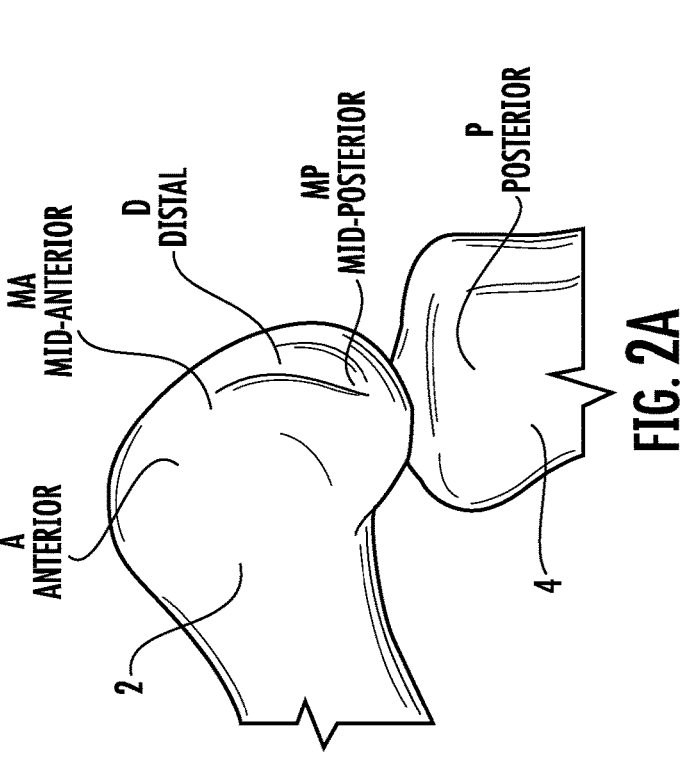
FIG. 2A illustrates various regions of a patient's anatomy.
Figure 2B:
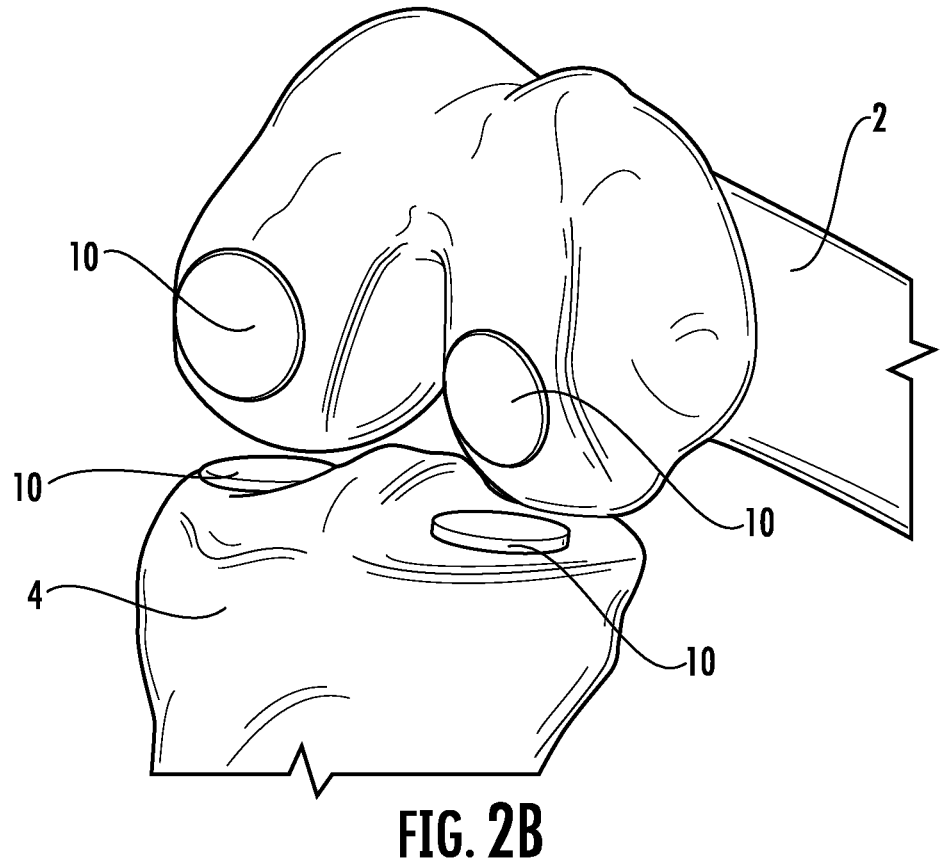
FIGS. 2B and 2C illustrate implants installed with various regions of a patient's anatomy.
Figure 2C:
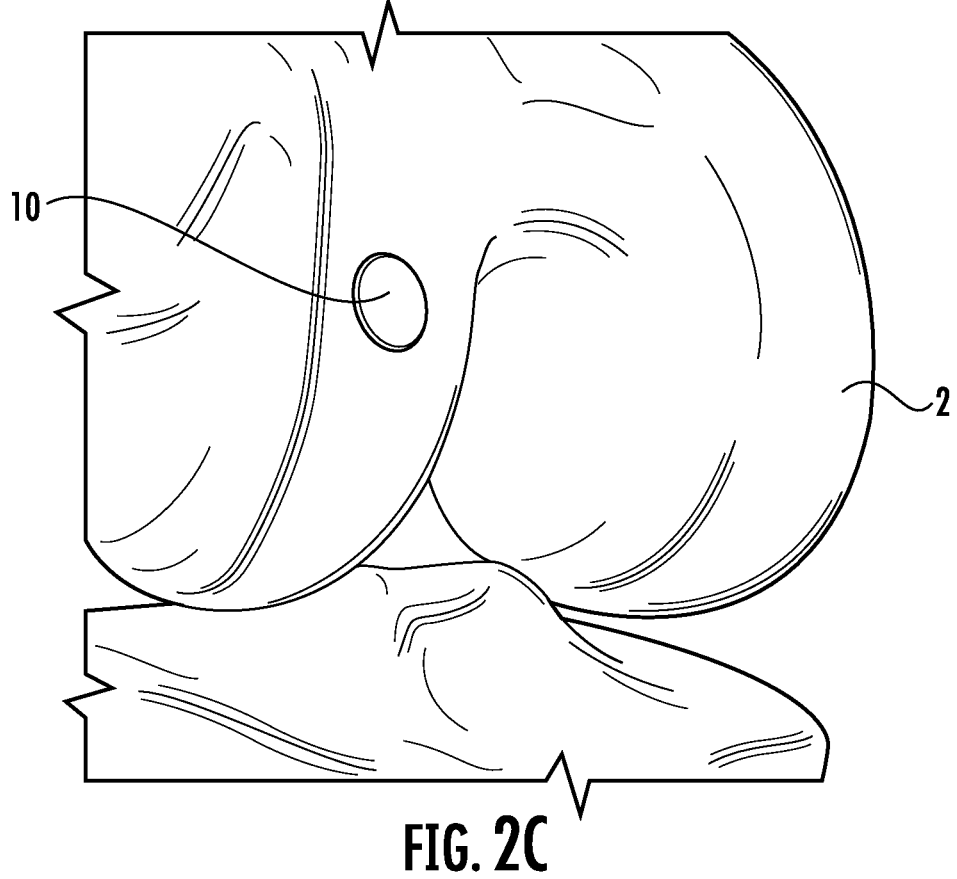

Aspects of the procedure are outlined in Table 1, along with FIG. 2A, which illustrates various regions of the femoral cam zones on the femur 2. FIG. 2A also shows an interface of the femur 2 with the tibia 4. As shown in Table 1, for each zone of the exemplary cam zones, there is a corresponding joint surface curve radius, which is shown in degrees in Table 1. The radius of curvature of the knee femoral condyle articulating surface is cam-shaped. To optimize the implant/host bearing surface match of an implant to the patient, the surgeon must ascertain the anatomic location of the cartilage defect being replaced and confirm the optimal match with the trocar drill guide. FIGS. 2B and 2C provide further illustrations of implants 10 arranged in the femur 2 and the tibia 4.

In any of the processes or descriptions provided herein, the implant 10 is installed to the correct depth, such that a bearing surface of the implant 10 is co-planar with the contiguous surrounding joint cartilage surface. The anchor body of the implant 10 can be entirely countersunk into the recipient bone (i.e. femur). In the event that the implant 10 is inadvertently installed too deep, the implant site can be cored out and a larger implant 10 can be installed as a replacement.

Figure 4A:
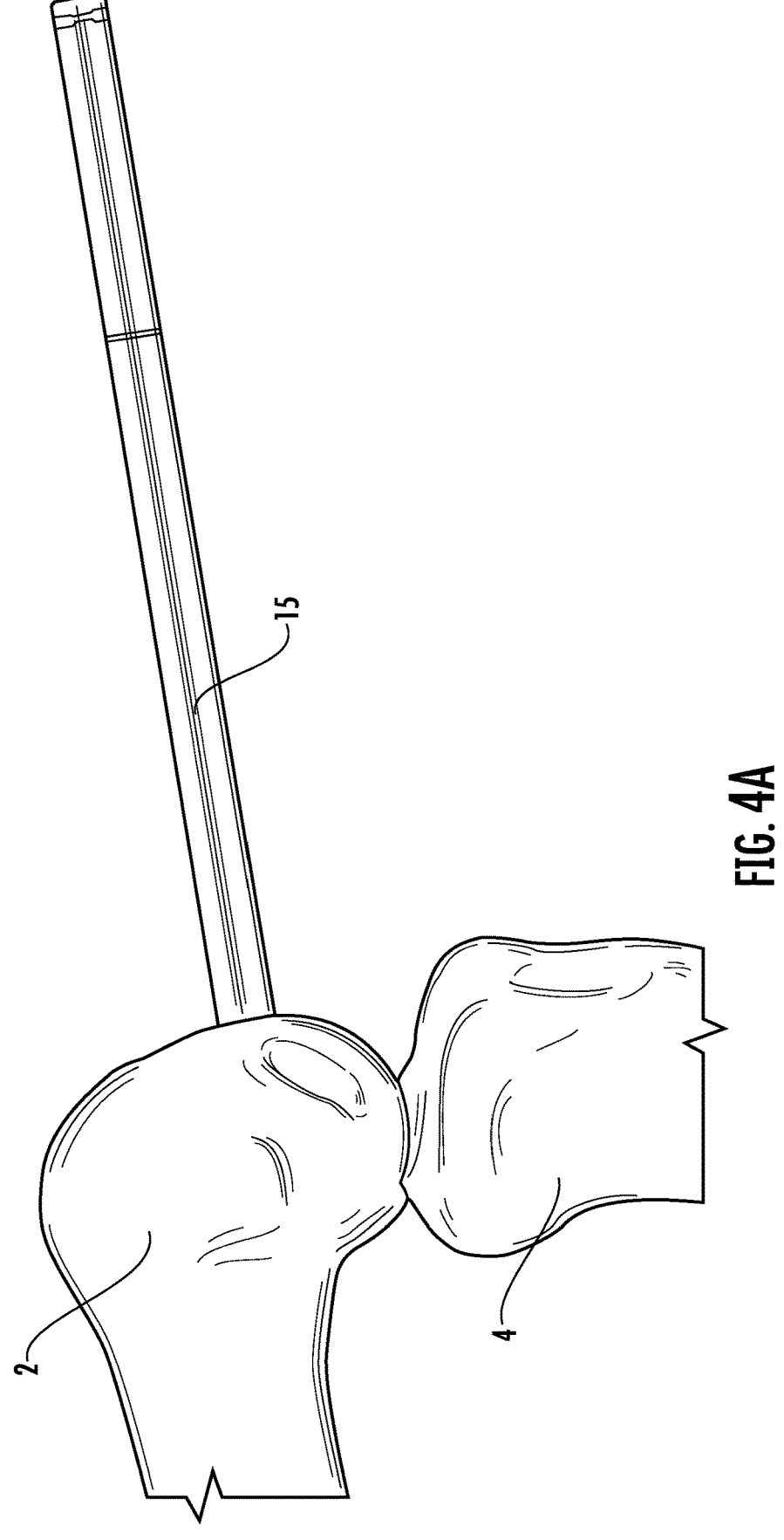
FIGS. 4A-4E illustrate various steps for preparing a recipient site for an implant and various steps of using associated instruments.

As shown in FIG. 4A, the process can include confirming the size and alignment of the patient's anatomy defects. The size of the cartilage surface defect is sized, measured, or detected using a trocar drill guide 15 centered over osteoarthritic grade III-IV lesion of femoral condyle articular surface. The process includes aligning the trocar drill guide 15, such that it is centered over eroded cartilage exposed bone. The process includes angling the trocar drill guide 15 to align the implant bearing surface with joint cartilage surface to optimize restored joint surface congruity. The process includes adjusting the trocar drill guide 15 to maximize circumferential rim contact of the trocar drill guide 15 with recipient site cartilage to optimize congruity of intact host joint cartilage and the implant bearing surface. In one aspect, this process is performed using compression, such as tactile compression, in which a surgeon compresses the trocar drill guide 15 onto the cartilage defect. This process can be performed until some tactile feedback is detected that there is contact with the rim of the implant recipient site.

Figure 4B:
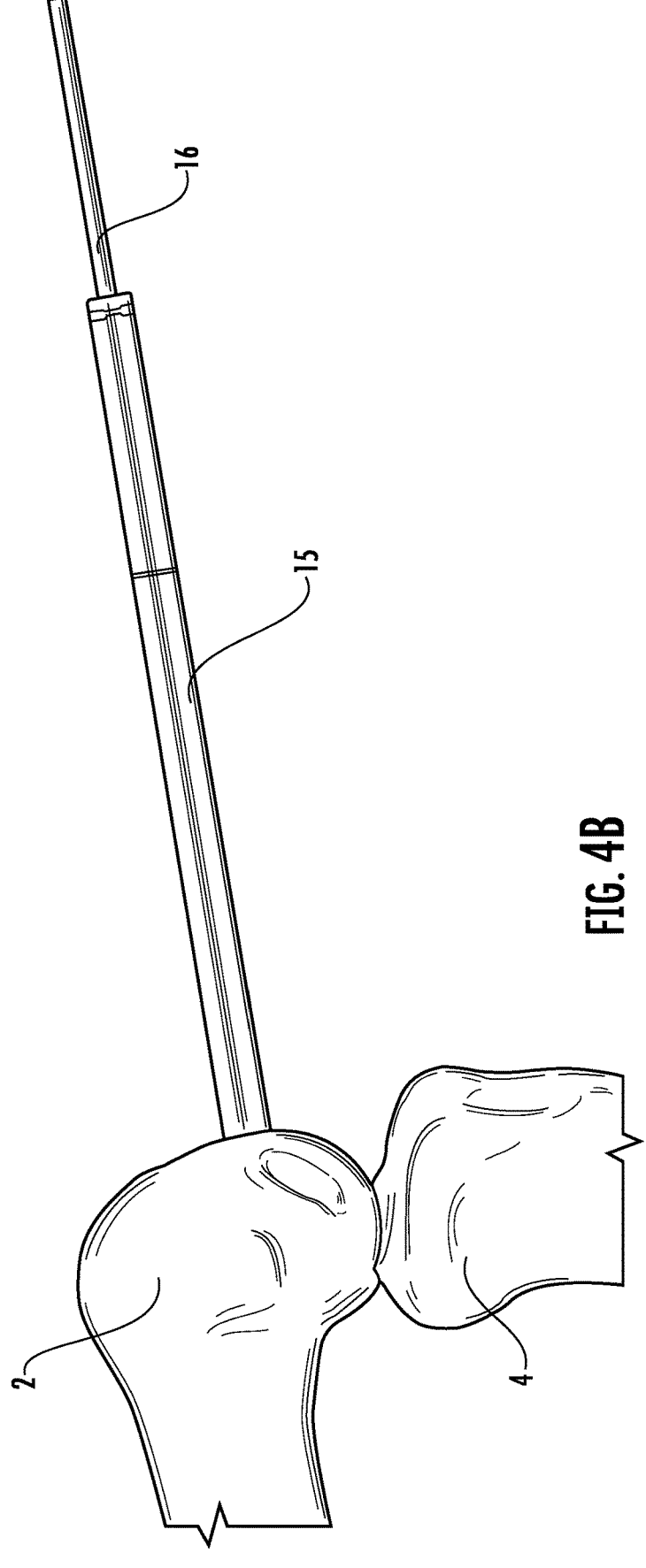

As shown in FIG. 4B, a K-wire 16 is inserted through the trocar drill guide 15. The process can include centering the trocar drill guide 15 to cover cartilage eroded exposed bone. The process includes adjusting alignment of the trocar drill guide 15 perpendicular to the femoral condyle and to a tangential plane of the cartilage defect. Alignment is confirmed via circumferential rim contact of a contoured surface of the trocar drill guide 15, through direct arthroscopic visualization. The K-wire 16 is installed for alignment fixation through a cannula in the trocar drill guide 15. The position and alignment of the K-wire 16 is critical for the remainder of the procedure.

Figure 4C:
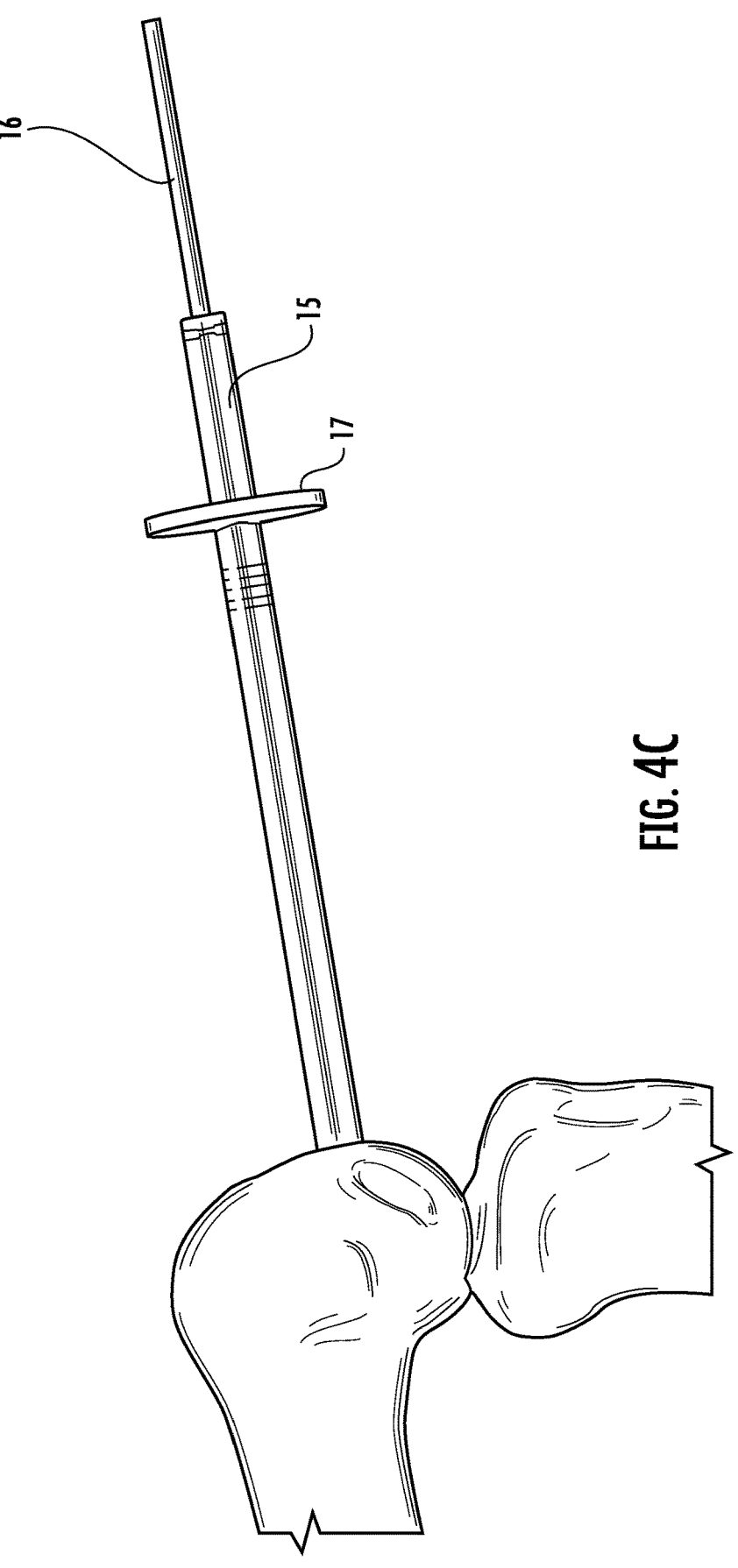

As shown in FIG. 4C, the cannula 17 is positioned such that it is aligned and slides over the trocar drill guide 15, which is stabilized by the K-wire 16. The cannula 17 is positioned on the cartilage rim of the recipient site surface defect.

Figure 4D:
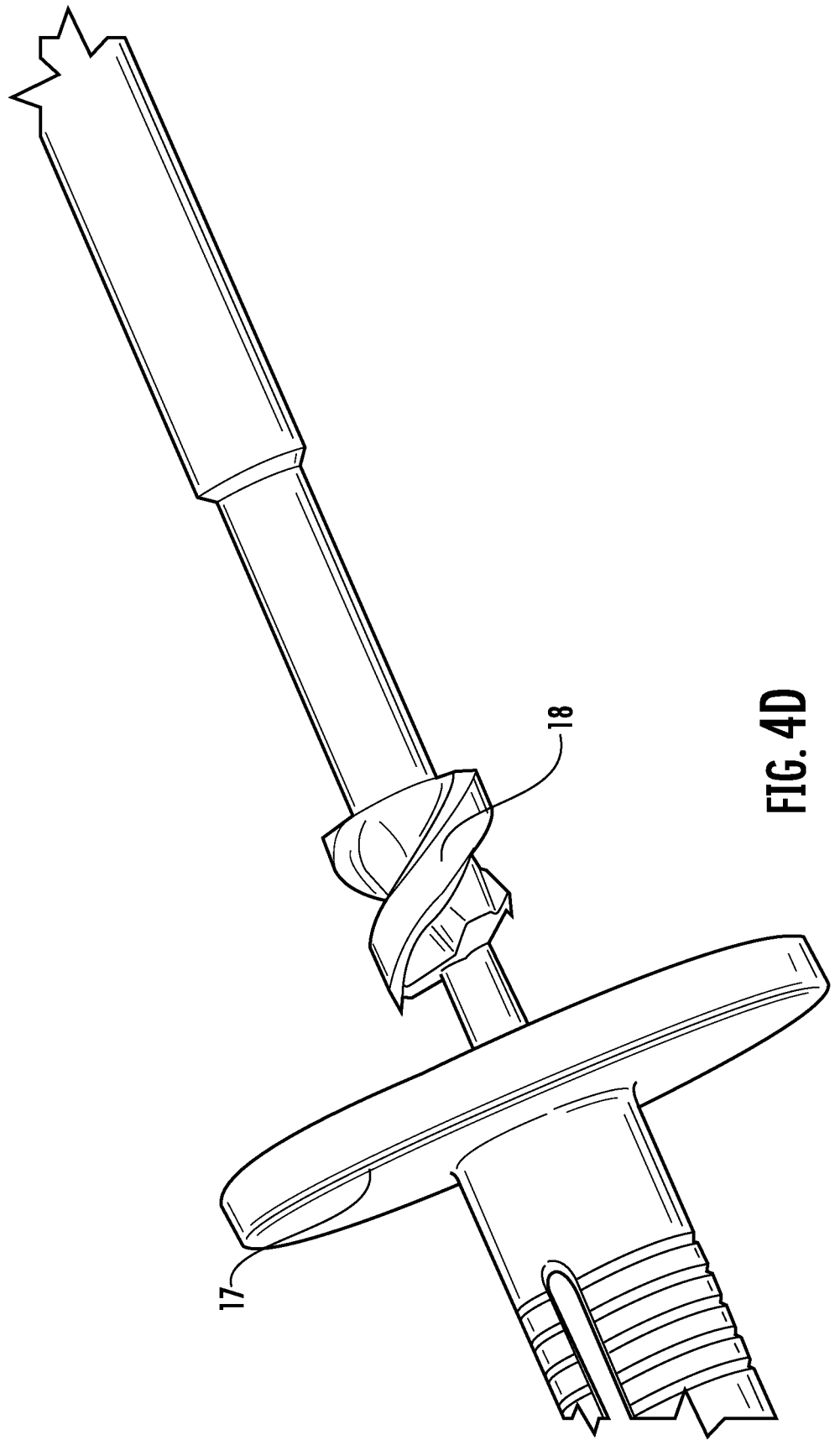
Figure 4E:

FIGS. 4D and 4E illustrate removal of the trocar drill guide 15 and placing the reamer 18 over the K-wire 16. The reamer 18 is configured to drill into or ream the patient's anatomy to prepare the recipient site for implant 10. The reamer 18 includes a stop 18' that prevents over reaming.

FIGS. 5A-5C illustrate further details of the reamer 18. Specifically, FIG. 5C overlays the implant 10 with a cutting end of the reamer 18 (shown in dashed lines) to show how the cutting end of the reamer 18 is undersized relative to the implant 10 in order to provide a press fit fixation of the implant 10 relative to the recipient site that is reamed via the reamer 18. The reamer 18 is configured to pull bone debris into the cannula 17. In one aspect, the reamer 18 is undersized and has a straight edge or outer perimeter, while the implant 10 has a tapered side wall. This difference in geometry facilitates installing the implant 10 in the recipient site, which is followed by adjusting the angle of insertion as a final check that the implant 10 can be adequately installed.

FIGS. 6A-6C illustrate a trial tool 19 used for determining trial implant depth and alignment. If necessary, the K-wire 16 can be removed to adjust the trial tool 19. The recipient hole is undersized and has a straight cylindrical profile, while the sidewalls of the implant 10 are tapered, permitting adjustments of alignment. The trial tool 19 can be adjusted as required and prepare the site for installation of the implant 10. The trial tool 19 specifically can be used to assess and analyze the appropriate size for the implant rim and surrounding cartilage surface congruence.

FIGS. 7A-7C illustrate the implant 10 being installed with an impactor tool 20. The impactor tool 20 can include a rim impactor that engages a sidewall of the implant 10 to install the implant 10 through the cannula 17. The impactor tool 20 can engage a rim of the anchor body of the implant 10. A depth of the installation can be assessed to align the bearing surface of the implant 10 to be coplanar with the intact contiguous cartilage surface. The impactor tool 20 protects a hydrogel or bearing surface of the implant 10 during installation by applying force or impacting the rim of the implant 10 and not the bearing surface.

FIGS. 8A-8C illustrate that the cannula 17 includes at least one open slot 17a such that direct observation of the implant 10 is possible while the implant 10 is delivered to the recipient site via engagement with the impactor tool 20. The at least one slot 17a could be formed as any shape or profile, as long as some visual line of sight is provided from the exterior to the interior of the cannula 17.

Based on the instruments disclosed herein, the following technique can be employed to install the implant 10. First, an alignment process can be performed during which the trocar drill guide 15 can be aligned with the recipient site via tactile compression to ensure an optimal end surface contact with the cartilage surface apposition. A K-wire 16 can then be installed to a depth such that it maintains alignment through later drilling and trial steps. The trial tool 19 is then utilized to determine the recipient site depth and alignment. Next, the K-wire 16 can be removed. Finally, the implant 10 can be installed through the cannula 17 via manual compression and subsequent tapping with the impactor tool 20. Additional verification steps can be performed to ensure proper alignment before final seating.

In one aspect, using the tools disclosed herein, a method for installing an implant in a patient recipient site is disclosed. The method includes arranging a first instrument relative to the patient recipient site to confirm initial characteristics of the patient recipient site. The first instrument can be a trocar drill guide 15, in one aspect. The method can also include inserting a K-wire through the first instrument into a patient's anatomy. The method can includes arranging a second instrument, such as the cannula 17, around the first instrument and removing the first instrument. The method includes inserting a cutting tool, such as reamer 18 or other cutting, drilling, or reaming tool, inside of the second instrument and into engagement with the patient recipient site. The cutting tool has an outer circumferential cutting profile that is less than an outer circumferential profile of the implant. This ensures that the implant will have a secure press-fit or seat with the patient recipient site. The cutting tool is configured to remove bone debris from the patient recipient site. The method includes inserting a third instrument, such as the trial tool 19, into the patient recipient site to determine characteristics of the patient recipient site after removing bone debris from the patient recipient site. Next, the method includes installing the implant into the patient recipient site using a fourth instrument, such as impactor tool 20. The fourth instrument can include a rim configured to engage a peripheral sidewall of the implant, and avoid damaging the bearing surface defined by the implant. One of ordinary skill in the art would understand that various other steps and instruments could be used in connection with these steps.

Indirect Access Instrumentation

Difficulties arise when the surgeon does not have direct access or a direct line, i.e. radial or perpendicular, to the joint cartilage surface being replaced. The challenge is to do this precisely with only limited access through a minimal incision, at an angle that does not permit direct drilling. This disclosure also provides instruments and surgical techniques for preparing the recipient site for resurfacing the damaged cartilage joint surface that is not perpendicular to the surgeon's access to the damaged joint surface. This disclosure describes the instruments necessary for the installation of the medical implant 10 and indirect variable angles.

FIGS. 9A-9R, FIGS. 10A-10J, FIGS. 11A-11E, FIGS. 12A-12F, and FIGS. 13A-13L illustrate tools for indirect access machining of bone recipient sites. These tools allow for machining of a bone in which direct access to the bone is not available. In one aspect, the bone can be the femur 2, and in another aspect the bone can be the tibia 4.

Figure 9A:
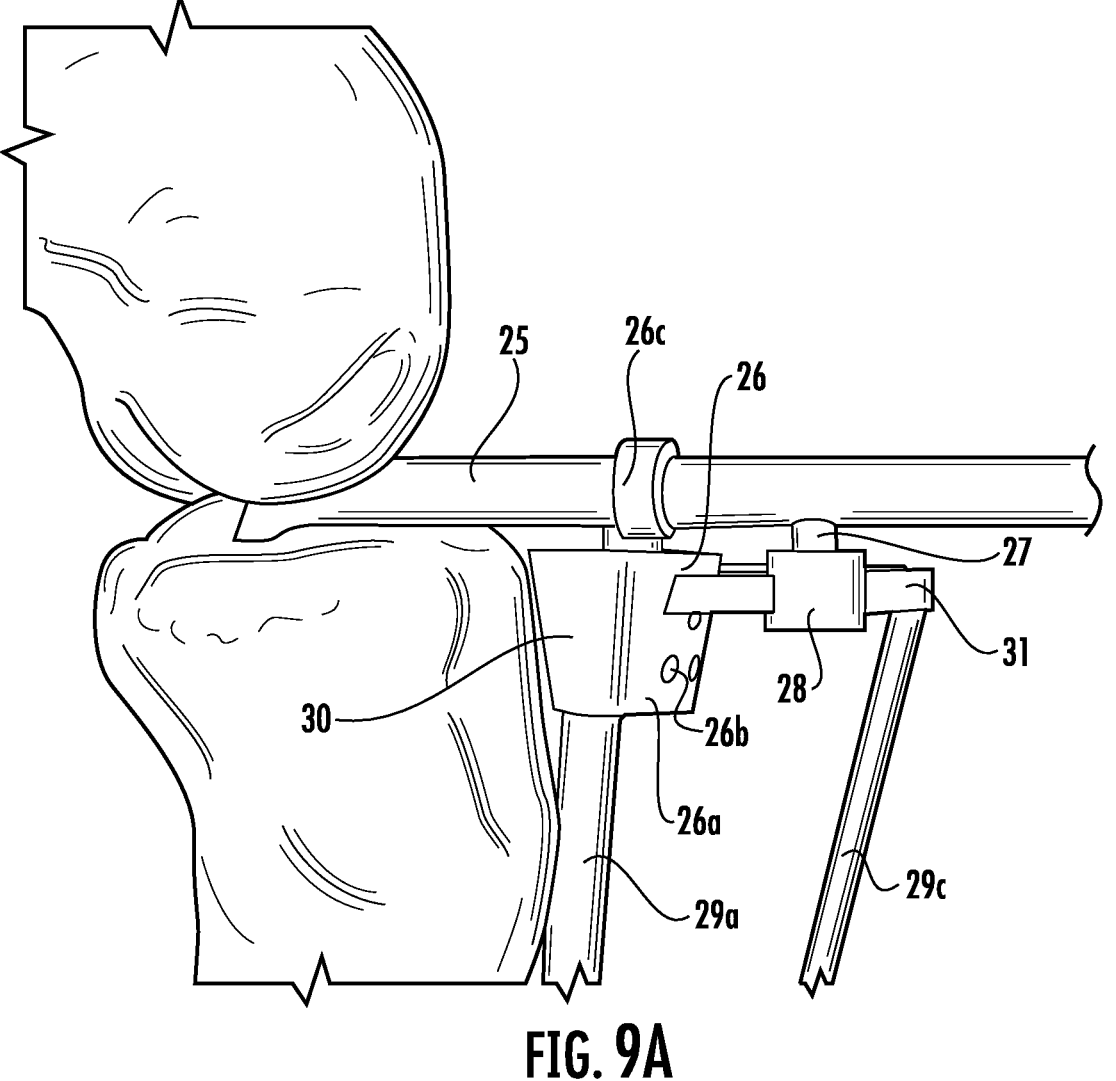
FIGS. 9A and 9B illustrate an alignment guide tool and a drill engaging a patient's anatomy according to one aspect.
Figure 9B:
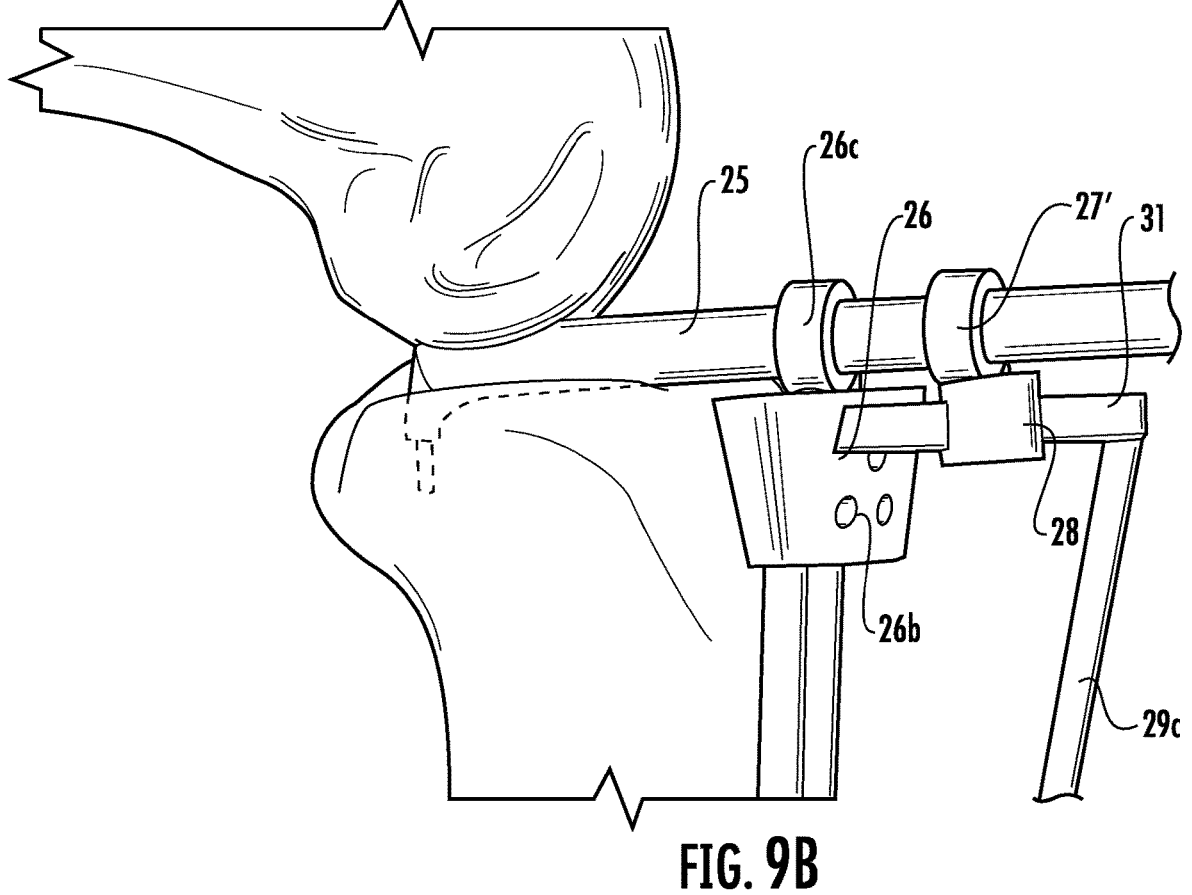
Figure 9C:
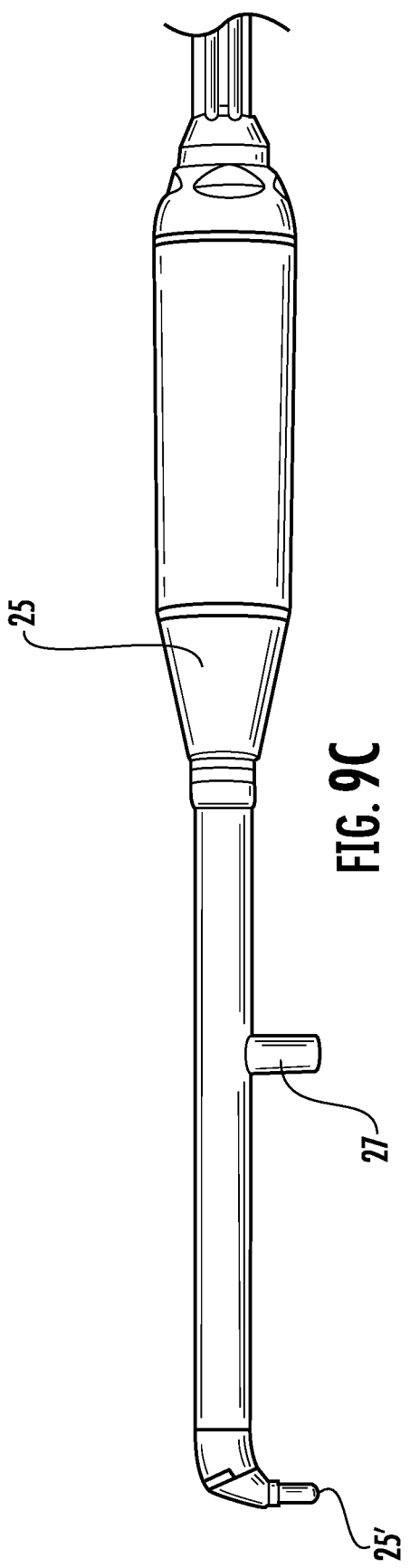
FIG. 9C illustrates the drill of FIGS. 9A-9B.
Figure 9D:
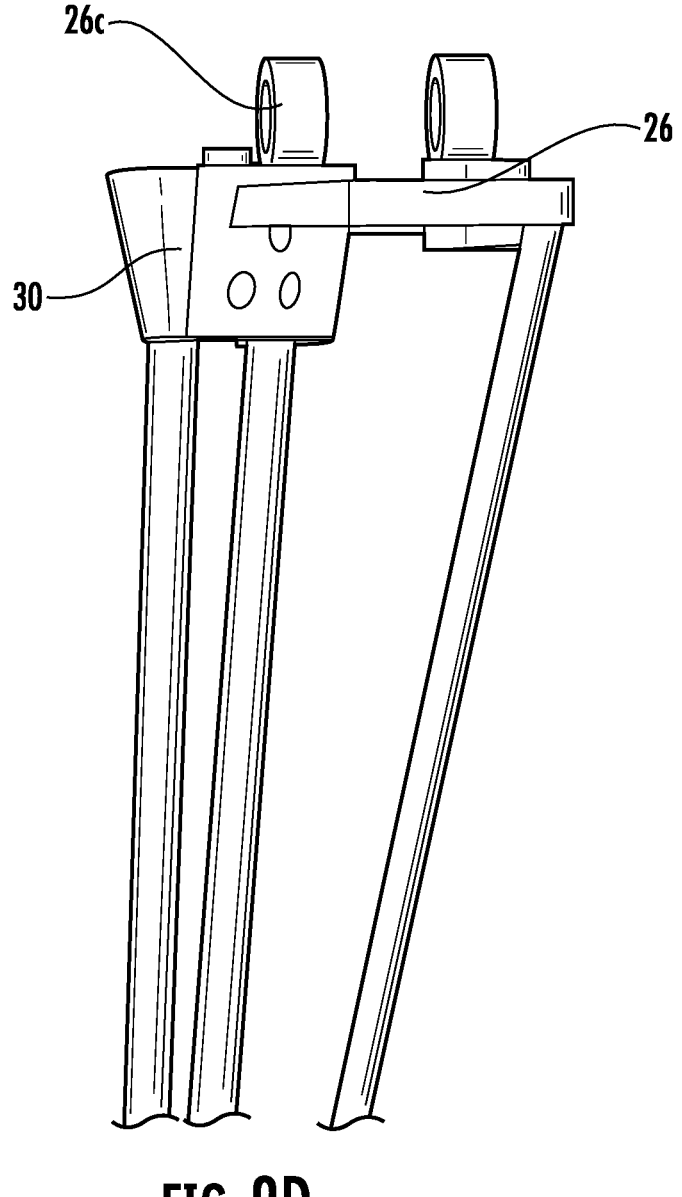
FIG. 9D illustrates the alignment guide tool of FIGS. 9A-9B.
Figure 9E:
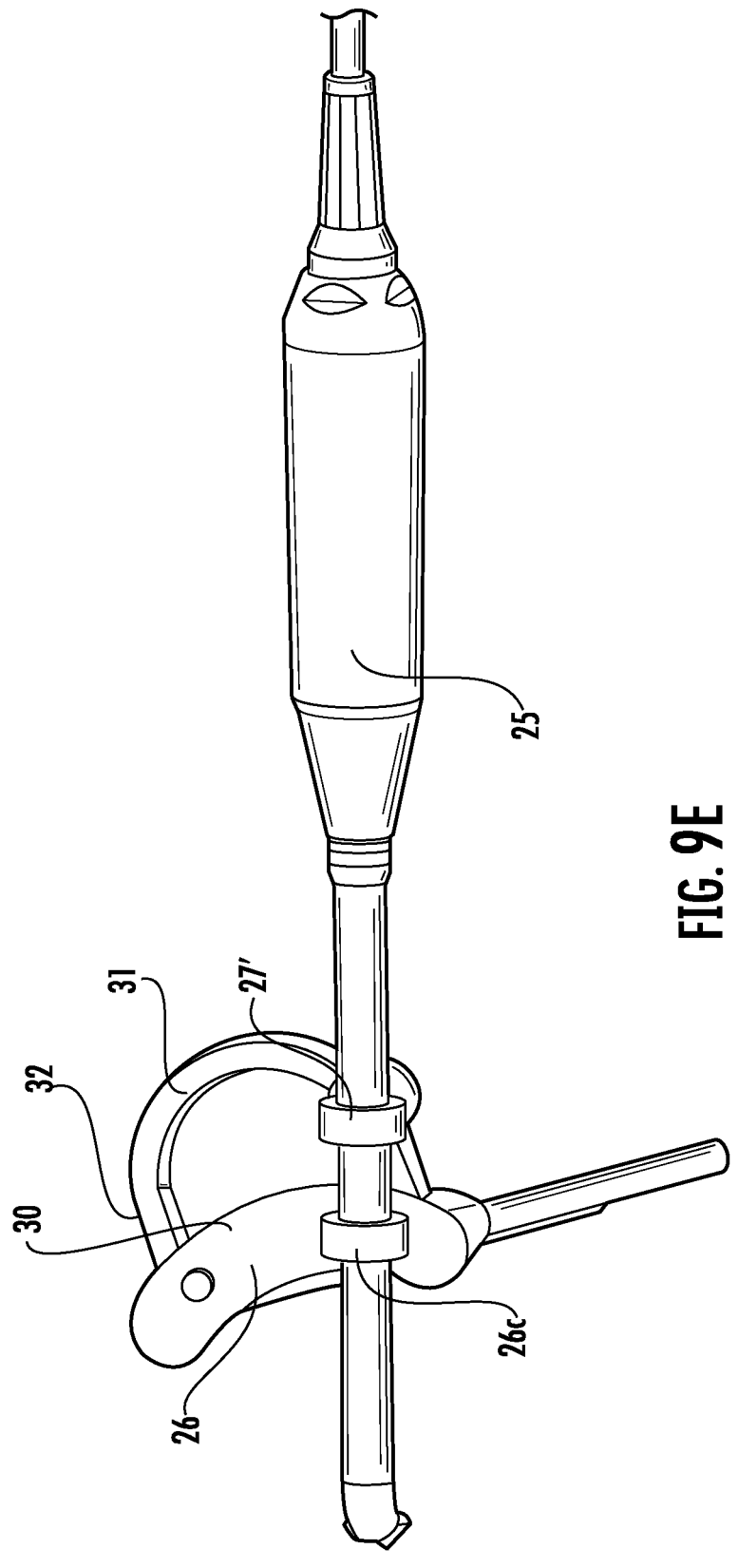
Figure 9F:
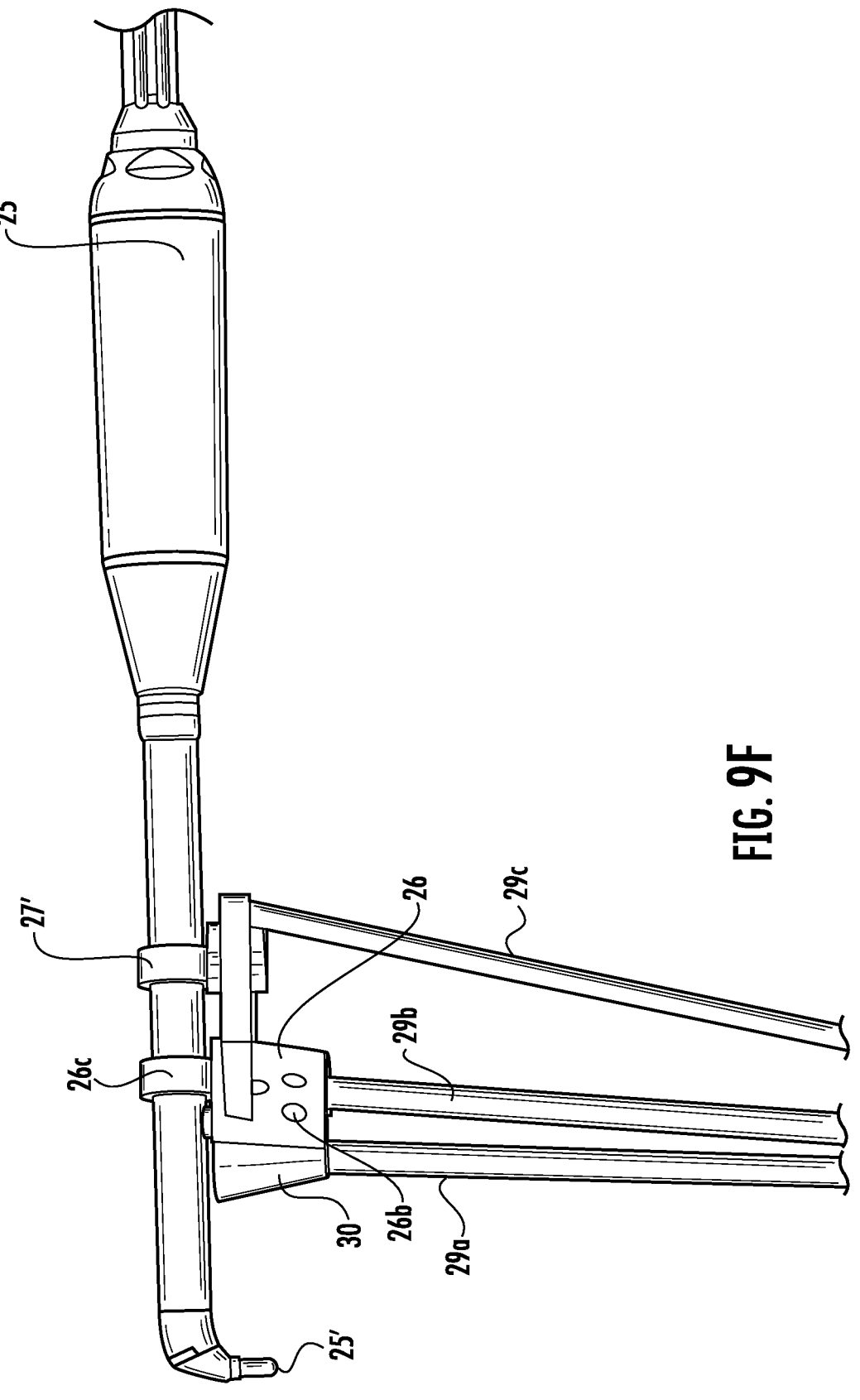
FIG. 9F is a side view of the alignment guide tool and the drill.
Figure 9G:
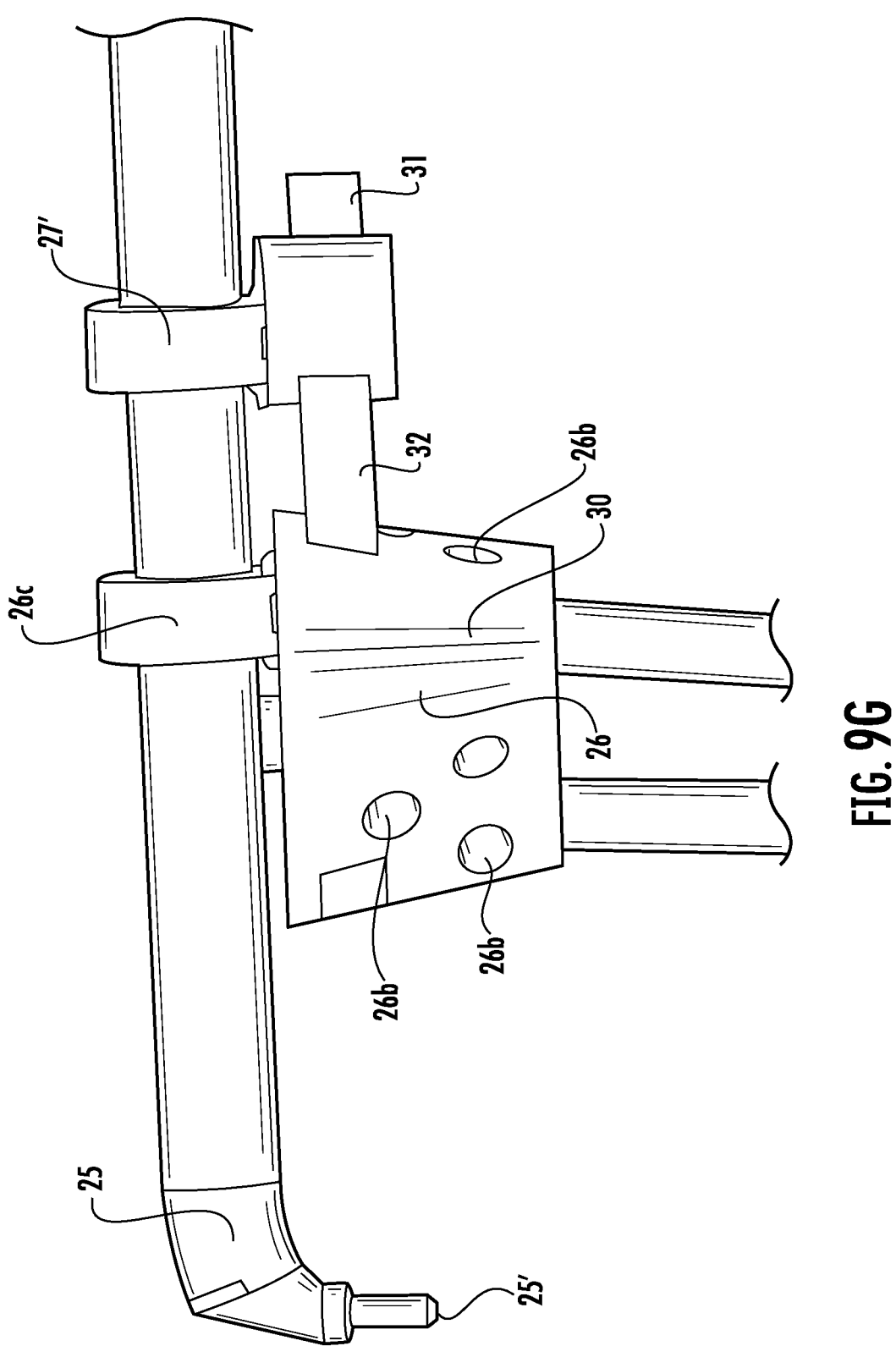
FIG. 9G is a magnified view of the alignment guide tool and the drill.
Figure 9H:
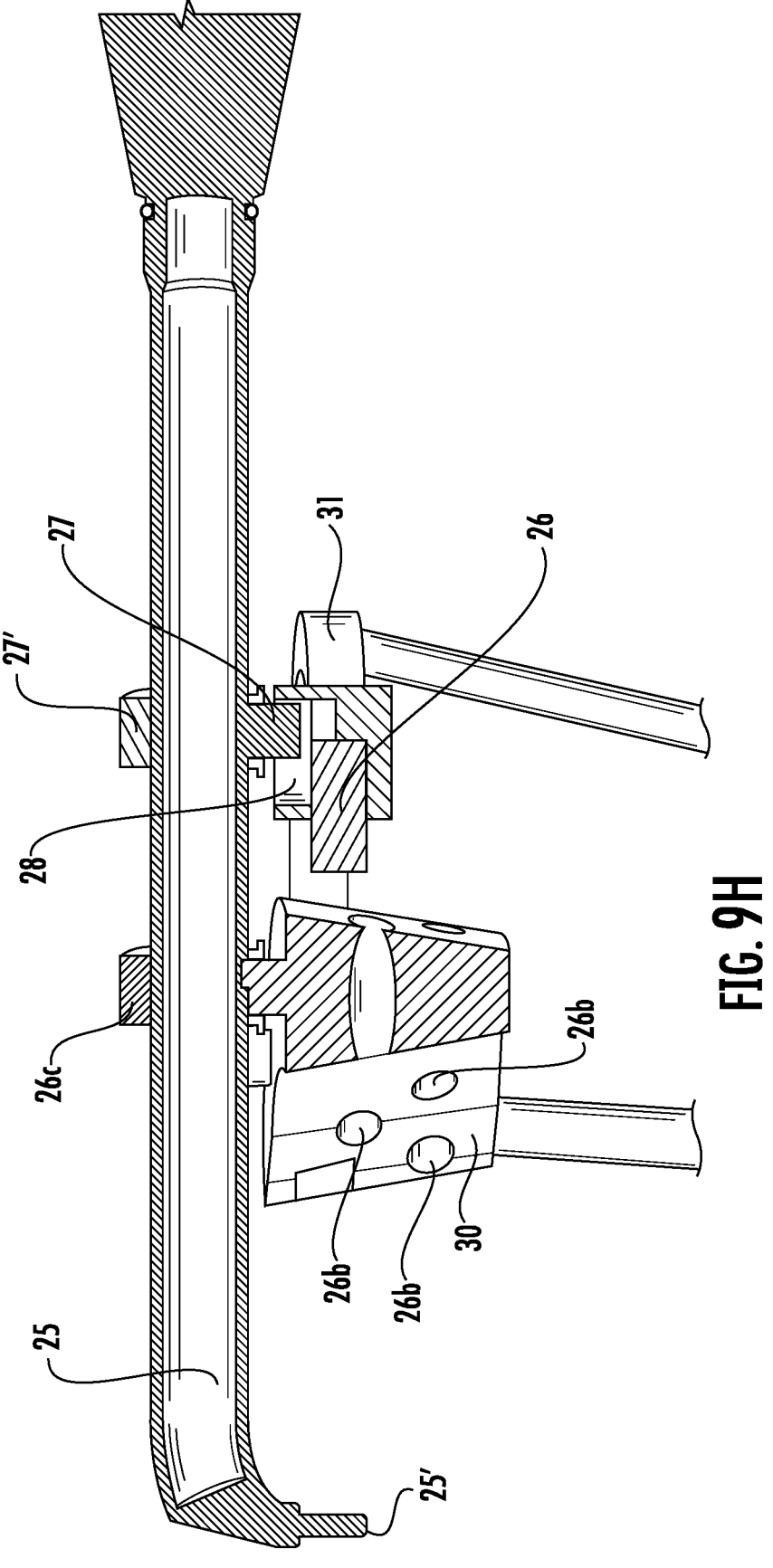
FIG. 9H is a cross-sectional view of the alignment guide tool and the drill.
Figure 9I:
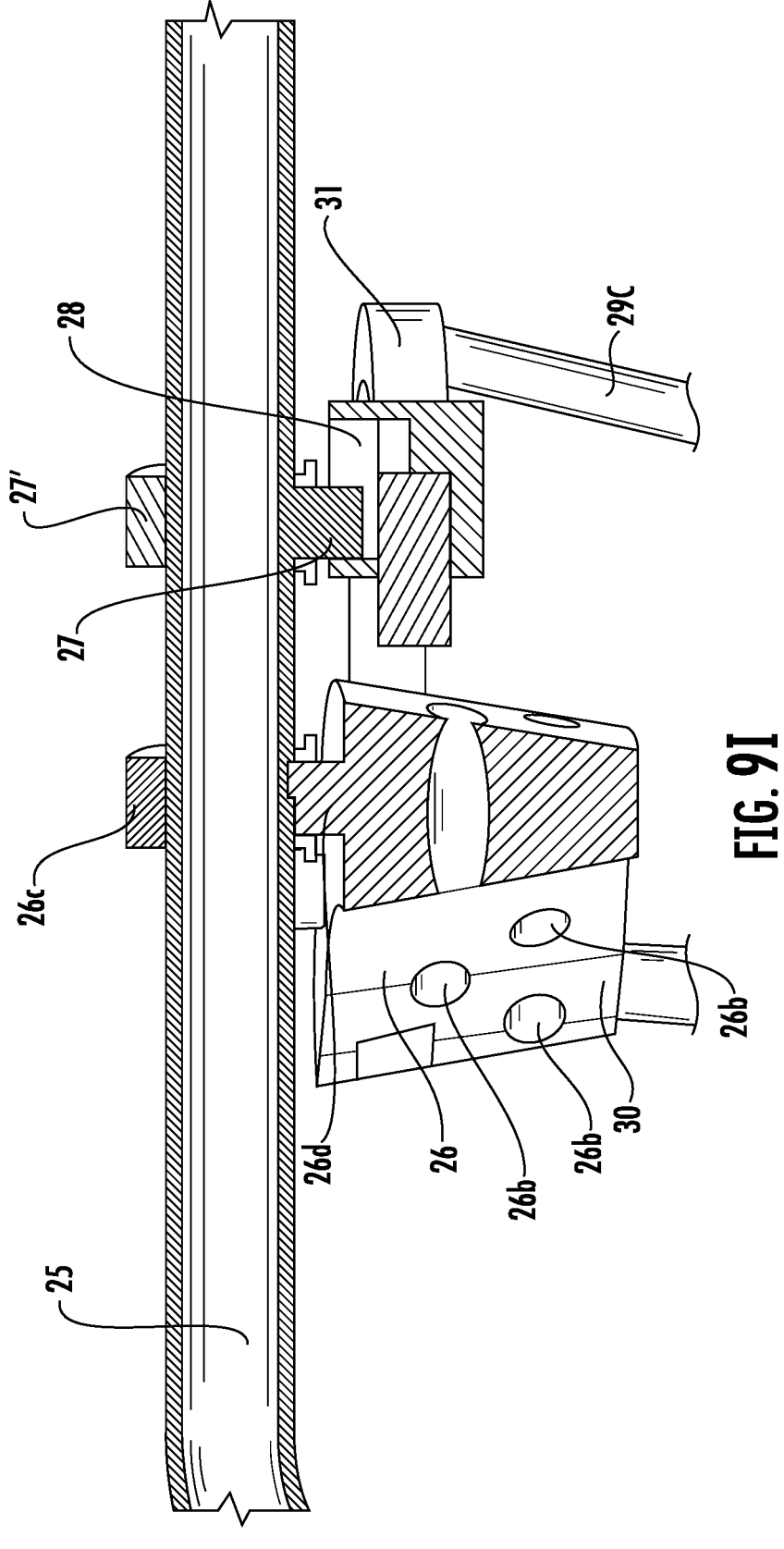
FIG. 9I is a magnified cross-sectional view of the alignment guide tool and the drill in a first position.
Figure 9J:
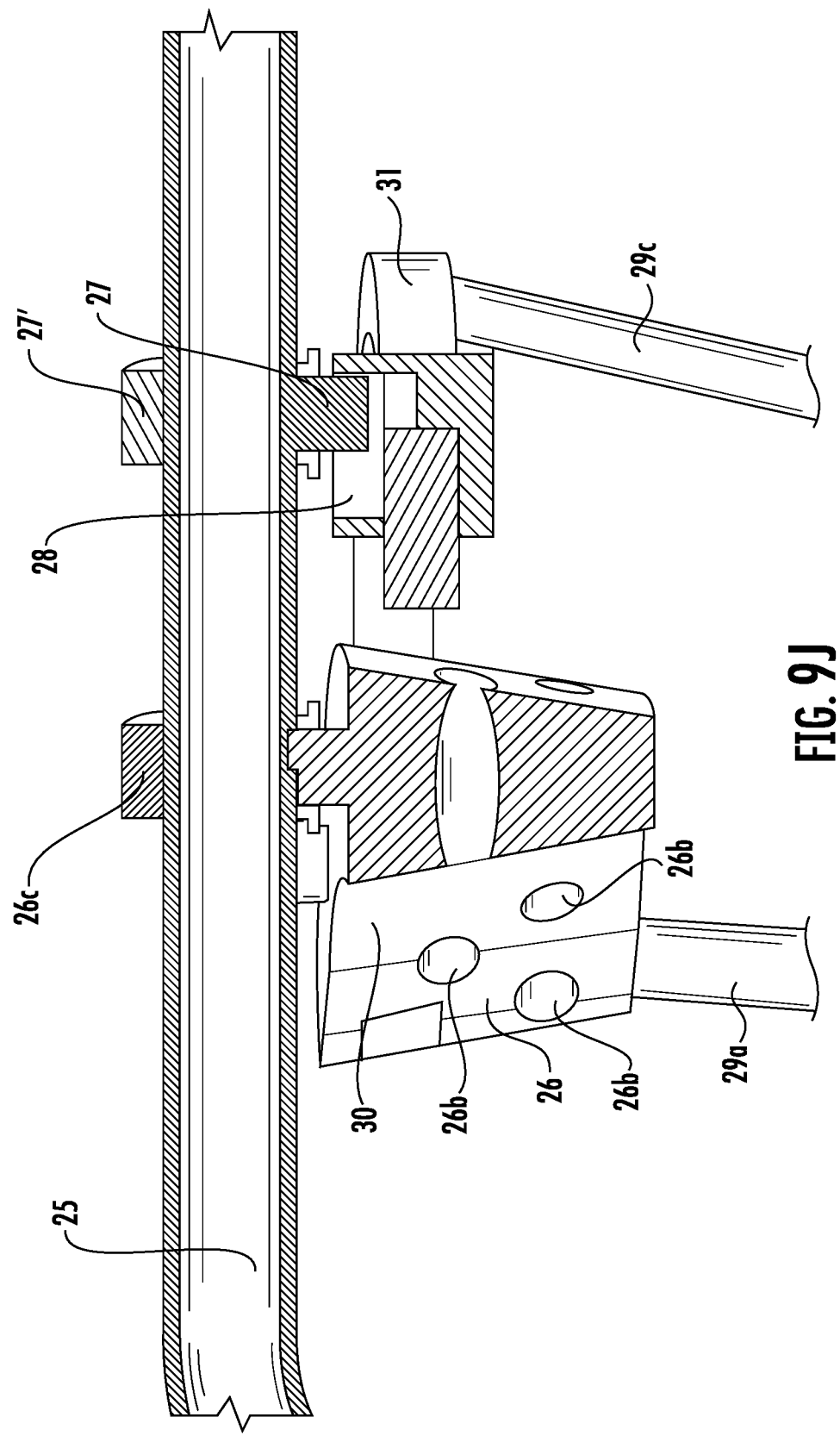
FIG. 9J is a magnified cross-sectional view of the alignment guide tool and the drill in a second position.
Figure 9K:
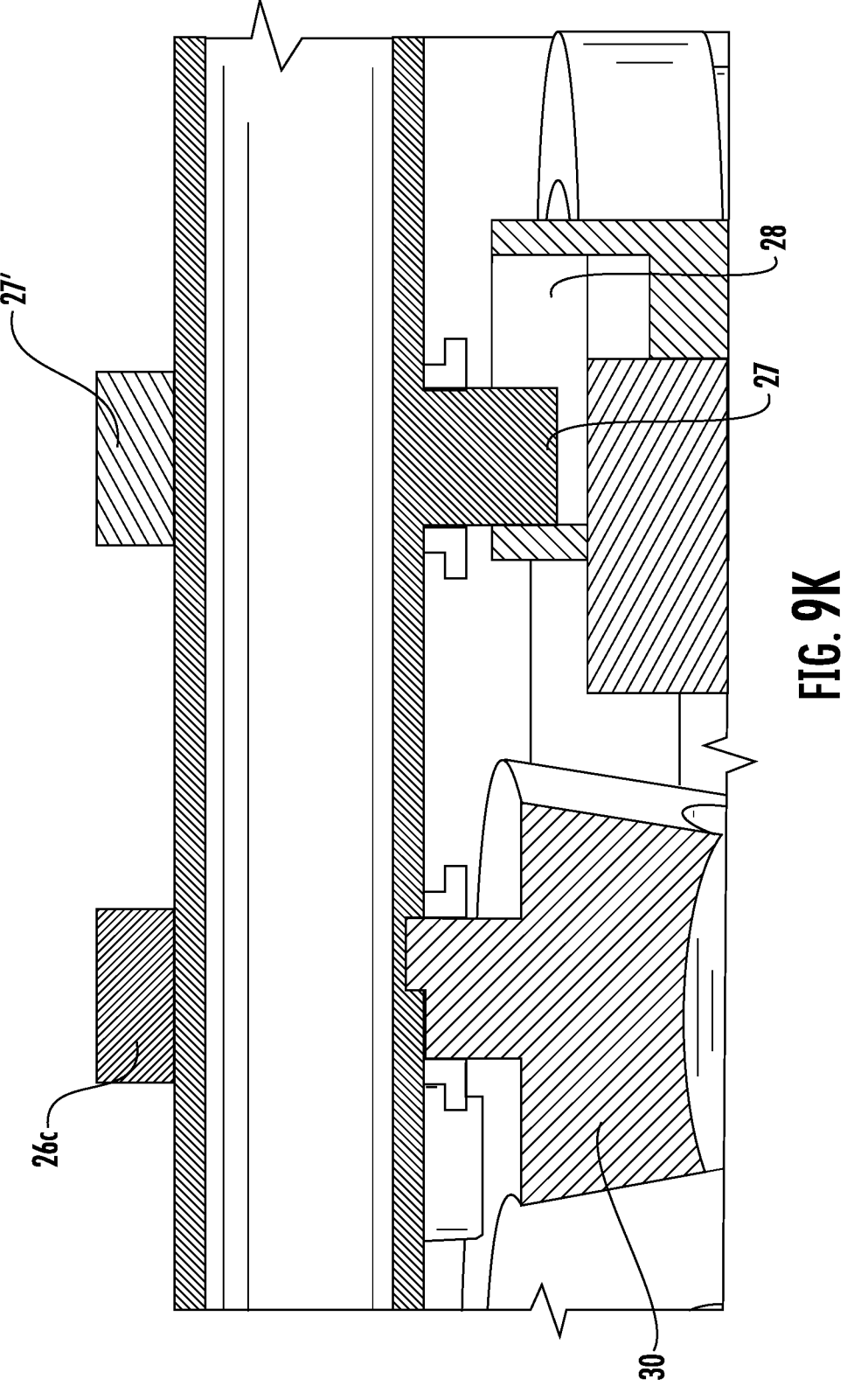
FIG. 9K is a further magnified cross-sectional view of the alignment guide tool and the drill in the first position.
Figure 9L:
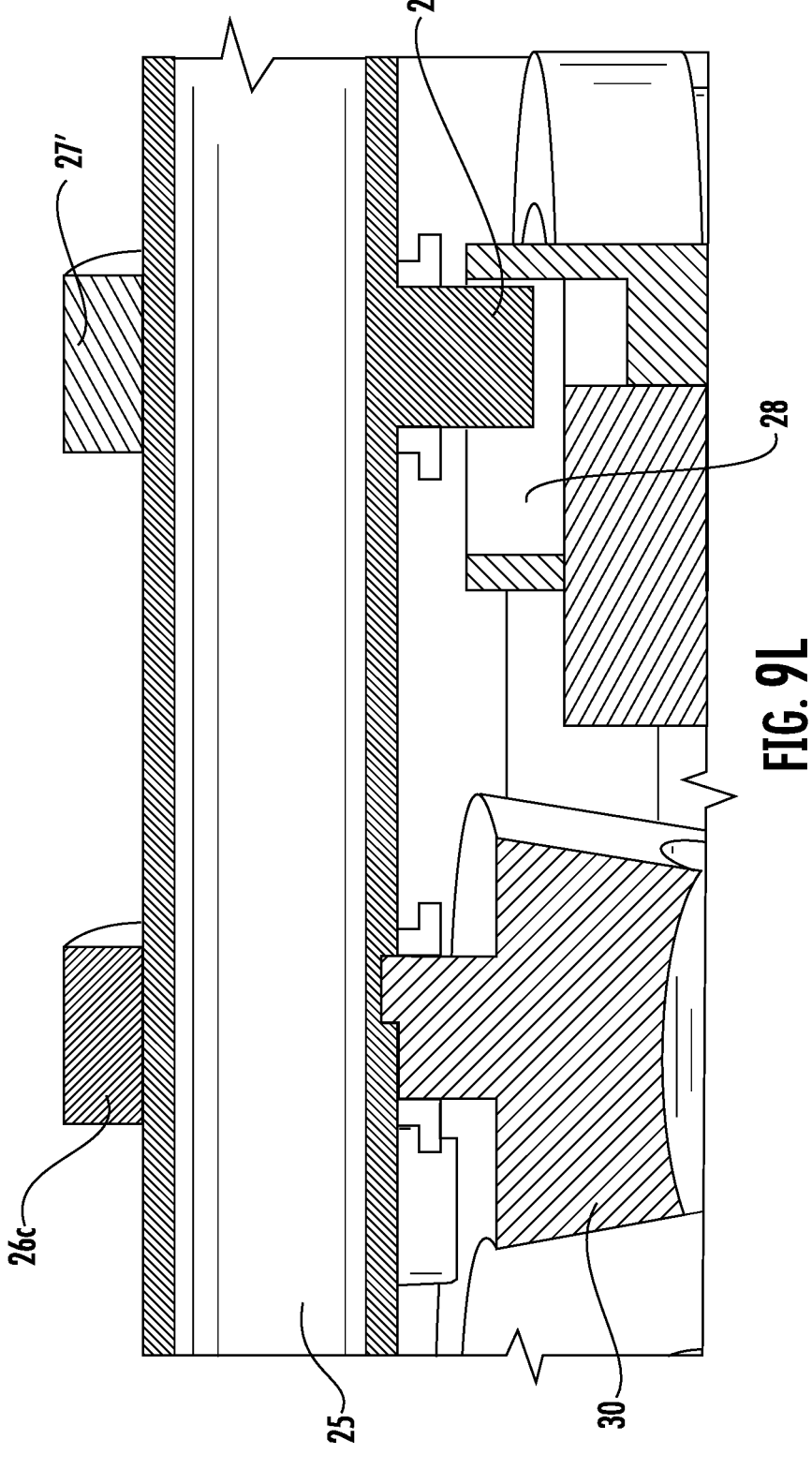
FIG. 9L is a further magnified cross-sectional view of the alignment guide tool and the drill in the second position.
Figure 9M:
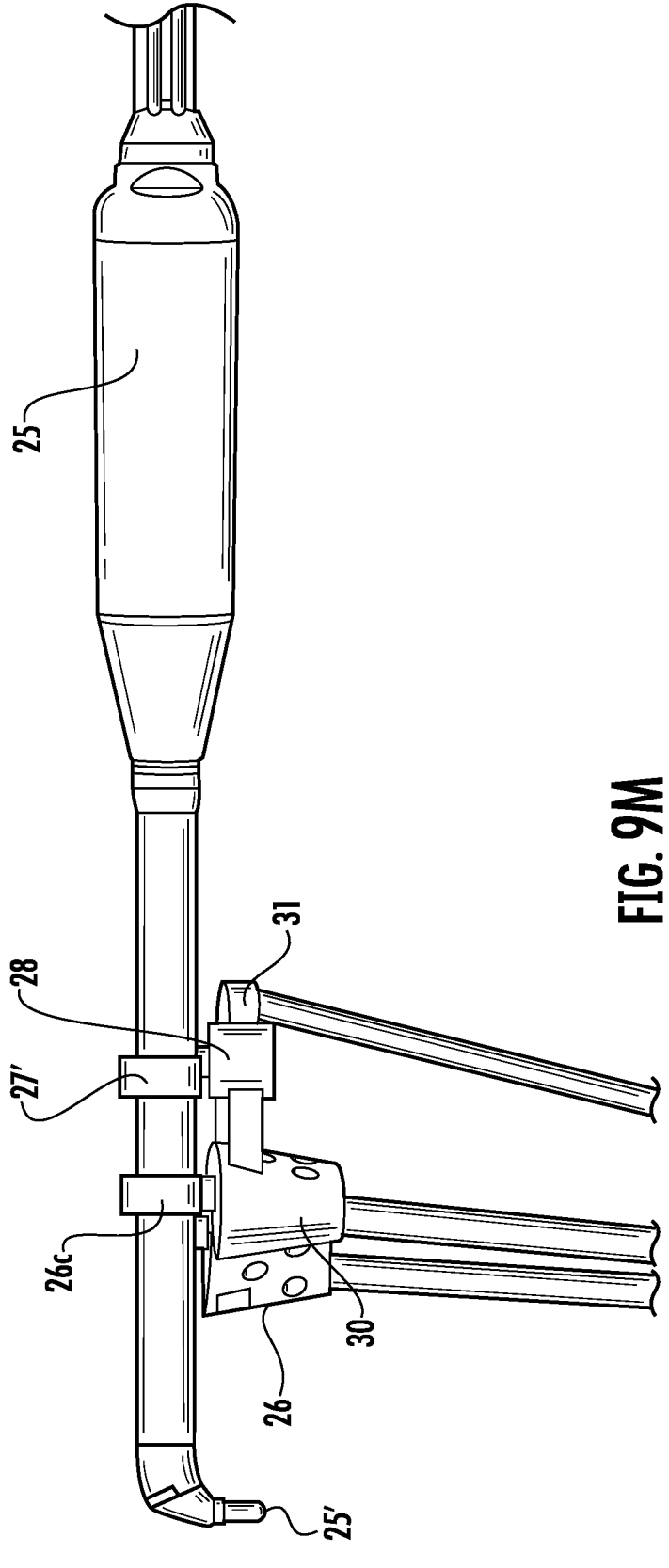
FIG. 9M is another view of the alignment guide tool and the drill.
Figure 9N:
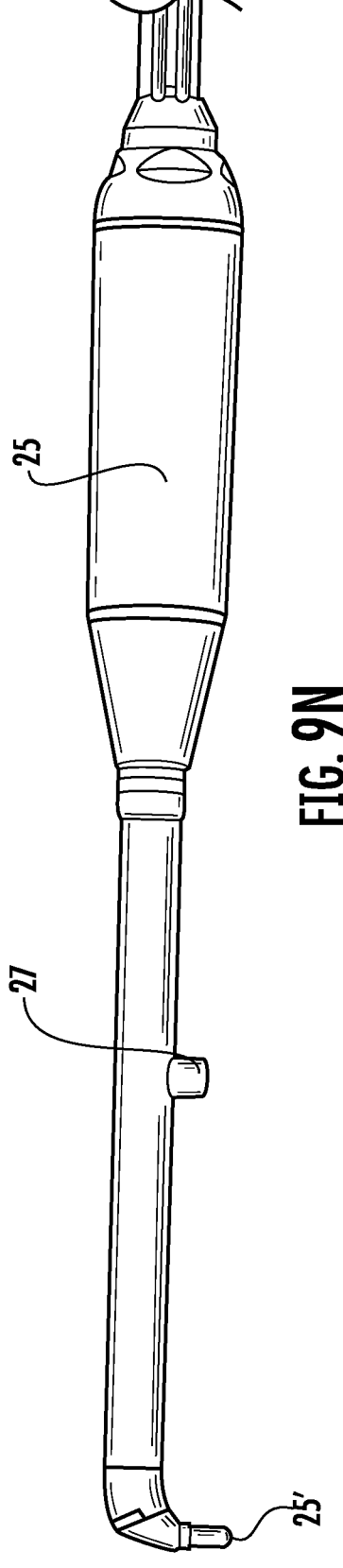
FIG. 9N is a perspective view of the drill.
Figure 90:
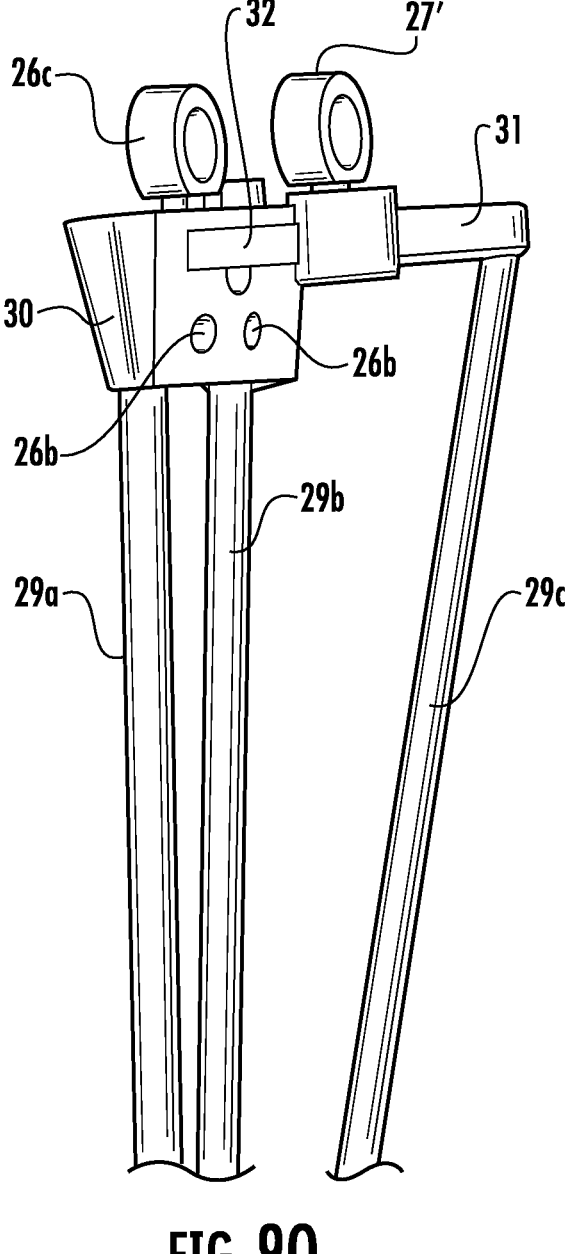
Figure 9P:
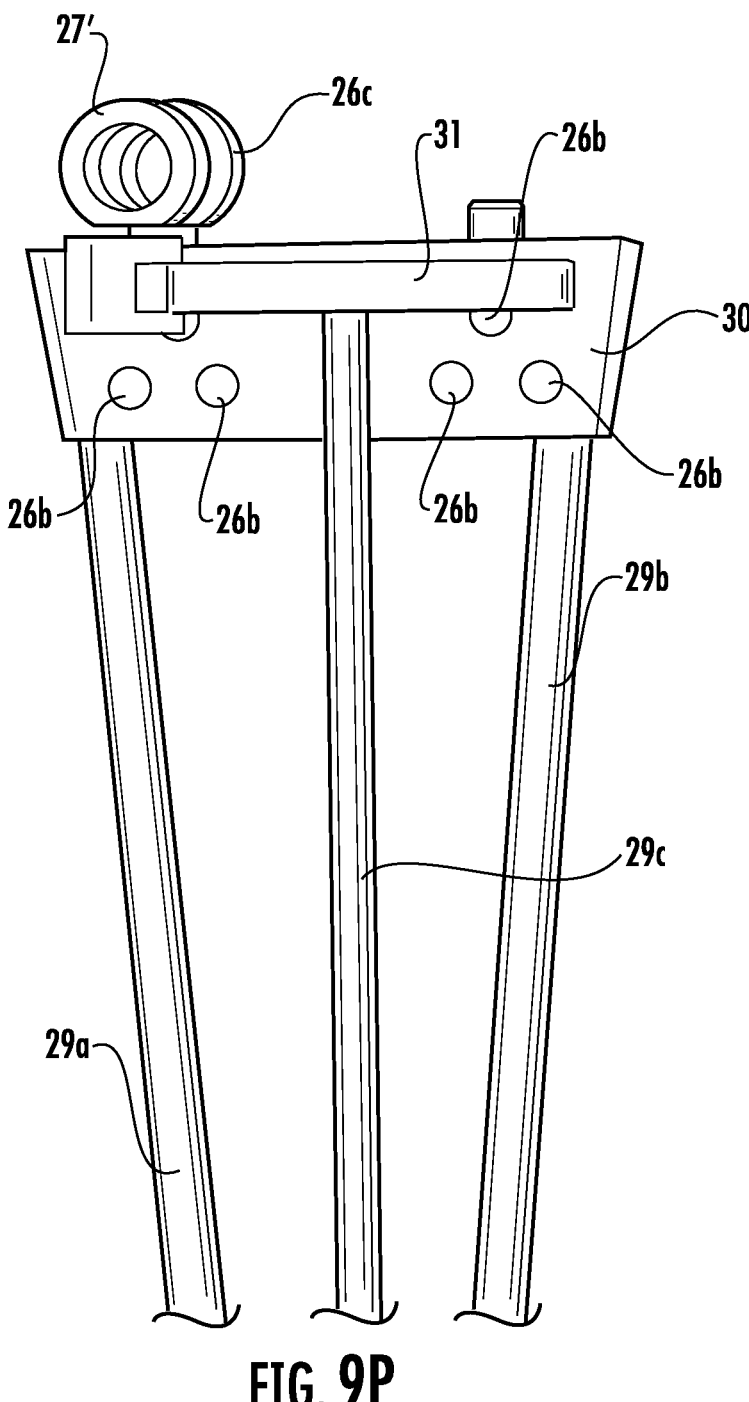
FIG. 9P is another view of the alignment guide tool.
Figure 9Q:
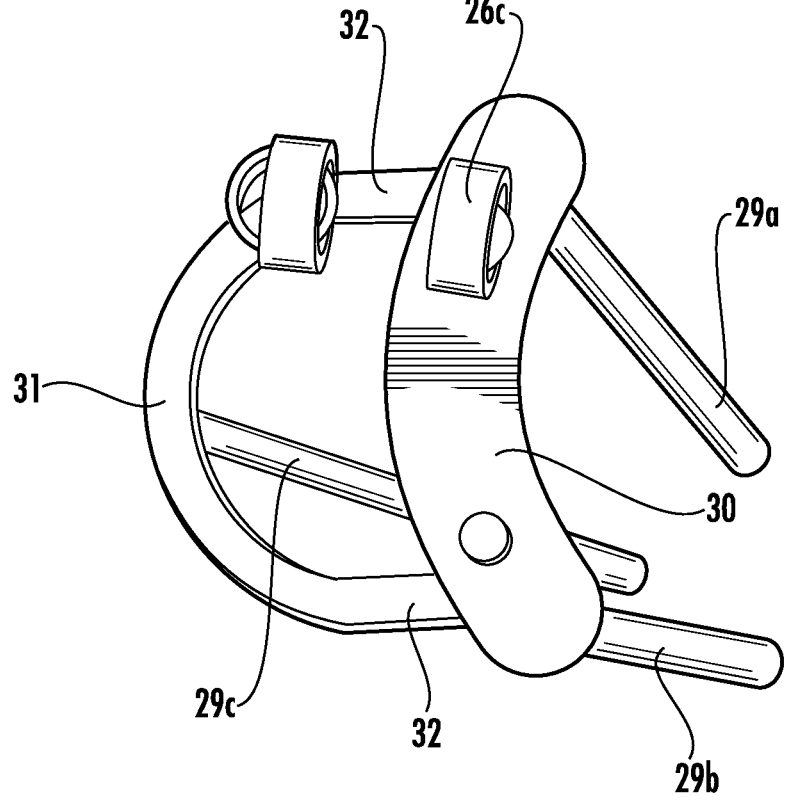
FIG. 9Q is a top view of the alignment guide tool.
Figure 9R:
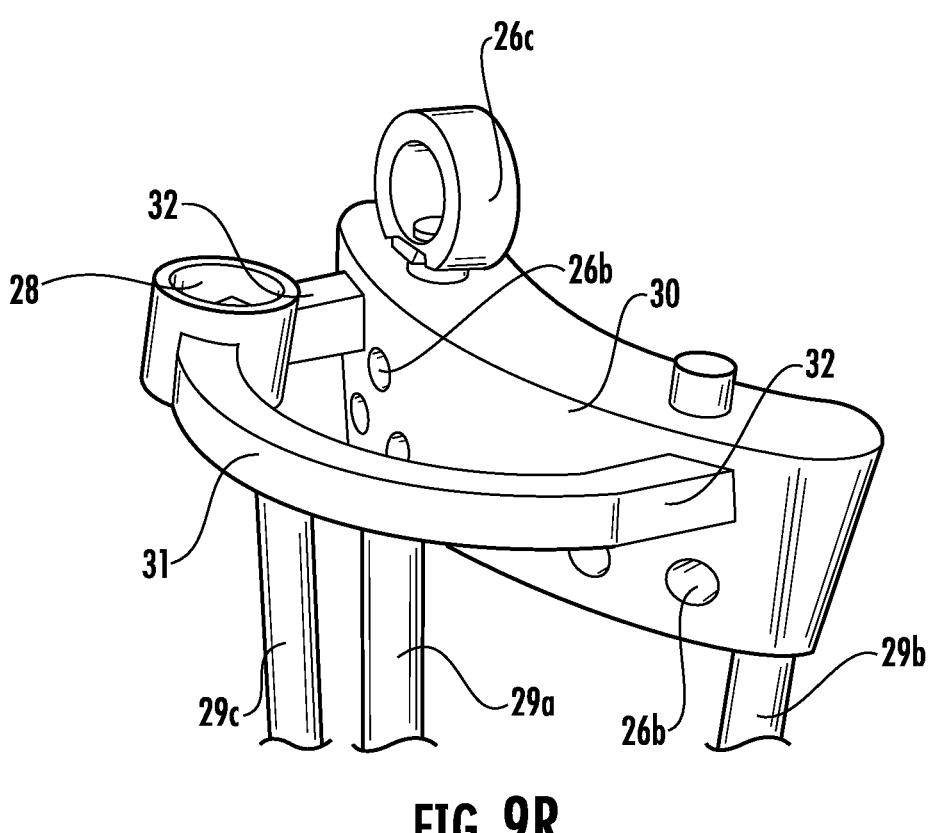
FIG. 9R is a magnified view of a portion of the alignment guide tool.

Referring to FIGS. 9A-9R, in one aspect, these tools include a drill 25, and an alignment guide tool 26. In one embodiment, the drill 25 is a right-angle drill and the alignment guide tool 26 is a tibial alignment guide tool. One of ordinary skill in the art would understand that other types of drills 25 could be used. Additionally, other tools besides a drill or cutting tool can be used with the alignment guide tool 26.

The alignment guide tool 26 can comprise a primary body 30 including a curved base portion that includes a plurality of bores or openings 26b configured to receive another component, such as K-wires. One of ordinary skill in the art would understand that the primary body 30 can have varying profiles. In one aspect, the primary body 30 has a curvature that is generally configured to rest against a patient's anatomy during use.

The primary body 30 also comprises a passage defined by a guide interface 26c configured to receive a portion of the drill 25. The guide interface 26c can be formed as a closed loop in one embodiment. The guide interface 26c can comprise a post 26d formed on the primary body 30, and the guide interface 26c can include a ring that is pivotally mounted on the post 26d. The closed loop of the guide interface 26c can be dimensioned to allow sliding movement of the drill 25 therein. The guide interface 26c can include a pivoting or swivel attachment to the primary body 30 such that the drill 25 can be moved side-to-side or laterally while supported within the guide interface 26c.

A tool excursion limiting assembly is provided via a protrusion 27 arranged within a receptacle 28 formed on the alignment guide tool 26. In one aspect, the protrusion 27 is provided integrally on the drill 25, as shown in FIGS. 9A and 9C. In another aspect, the protrusion 27 can be formed as a separate piece, and can be formed on a ring 27' or other element that is configured to be attached or arranged on the drill 25, as shown in FIG. 9B and FIGS. 9G-9L.

The protrusion 27 and the receptacle 28 act as a control for restricting the drill 25 from leaving a predetermined geometric shape, and thereby precisely controlling the shape of the machined recipient site. This configuration controls the geometry of the machined recipient site. The predetermined geometric shape of the receptacle 28 can mimic or reflect the general dimensions or parameters of the recipient site. For example, the predetermined geometric shape of the receptacle 28 can generally match the perimeter or outer profile of the implant 10, or can be slightly smaller than the perimeter or outer profile of the implant 10. Therefore, the receptacle 28 restricts the machining of the bone to the desired shape outlined by the receptacle 28. A depth of the receptacle 28 is dimensioned such that the receptacle 28 consistently retains the protrusion 27 within the receptacle 28.

One of ordinary skill in the art would understand that in an alternative embodiment, a male feature, i.e. protrusion 27, could be defined on the alignment guide tool 26, and a female feature, i.e. receptacle 28, could be formed on the drill 25. Additionally, various other configurations could be provided that limit the amount of reach of the drill 25 via some interface or engagement with the alignment guide tool 26.

The alignment guide tool 26 can include a plurality of struts 29a, 29b, 29c. While three struts are shown, one skilled in the art would understand that more or less struts can be used in different aspects. These struts 29a, 29b, 29c can be pinned to the tibia through holes for stability. These struts 29a, 29b, 29c can be considered extramedullary guides which can be fixed to the leg with straps that wrap around the ankle and calf, further stabilizing the working platform. The plurality of struts 29a, 29b, 29c can be formed integrally with the alignment guide tool 26.

The alignment guide tool 26 can further comprise a secondary body 31, shown for example in FIGS. 9A, 9B, 9Q, 9R, with at least one connection arm 32 extending to the primary body 30. In one aspect, at least two connection arms 32 can be provided between the primary body 30 and the secondary body 31. One of the plurality of struts 29c can be formed with the secondary body 31, and two of the plurality of struts 29a, 29b can be formed with the primary body 30. One of ordinary skill in the art would understand that alternative configurations for the struts 29a, 29b, 29c relative to the primary body 30 and secondary body 31 are possible. In one aspect, the receptacle 28 is formed on the secondary body 31.

Triangulating Targeting Device for Treating Cartilage Disorders

Once a surgeon identifies a cartilage defect in a joint during arthroscopy on the tibia in the knee joint, difficulties arise in preparing the site for an implant to replace the damaged cartilage. The present disclosure provides various solutions that address these difficulties. One skilled in the art would understand that the devices, systems, methods, and processes disclosed herein can be used to prepare and install an implant in various parts of the body, and as such, are not limited by location or body part. A surgical tool assembly is disclosed herein that generally has a triangular profile and allows for a more stable engagement with a patient's anatomy.

FIGS. 10A-10J illustrate guide instruments for indirect access in order to machine a bone recipient site to prepare the bone site. In particular, a surgical tool assembly 34 is provided that comprises a first guide tool portion 35 and a second guide tool portion 44. The first guide tool portion 35 and the second guide tool portion 44 can be formed as separate structures in one embodiment. In another embodiment, the first guide tool portion 35 and the second guide tool portion 44 can be formed integrally with each other.

Figure 10A:
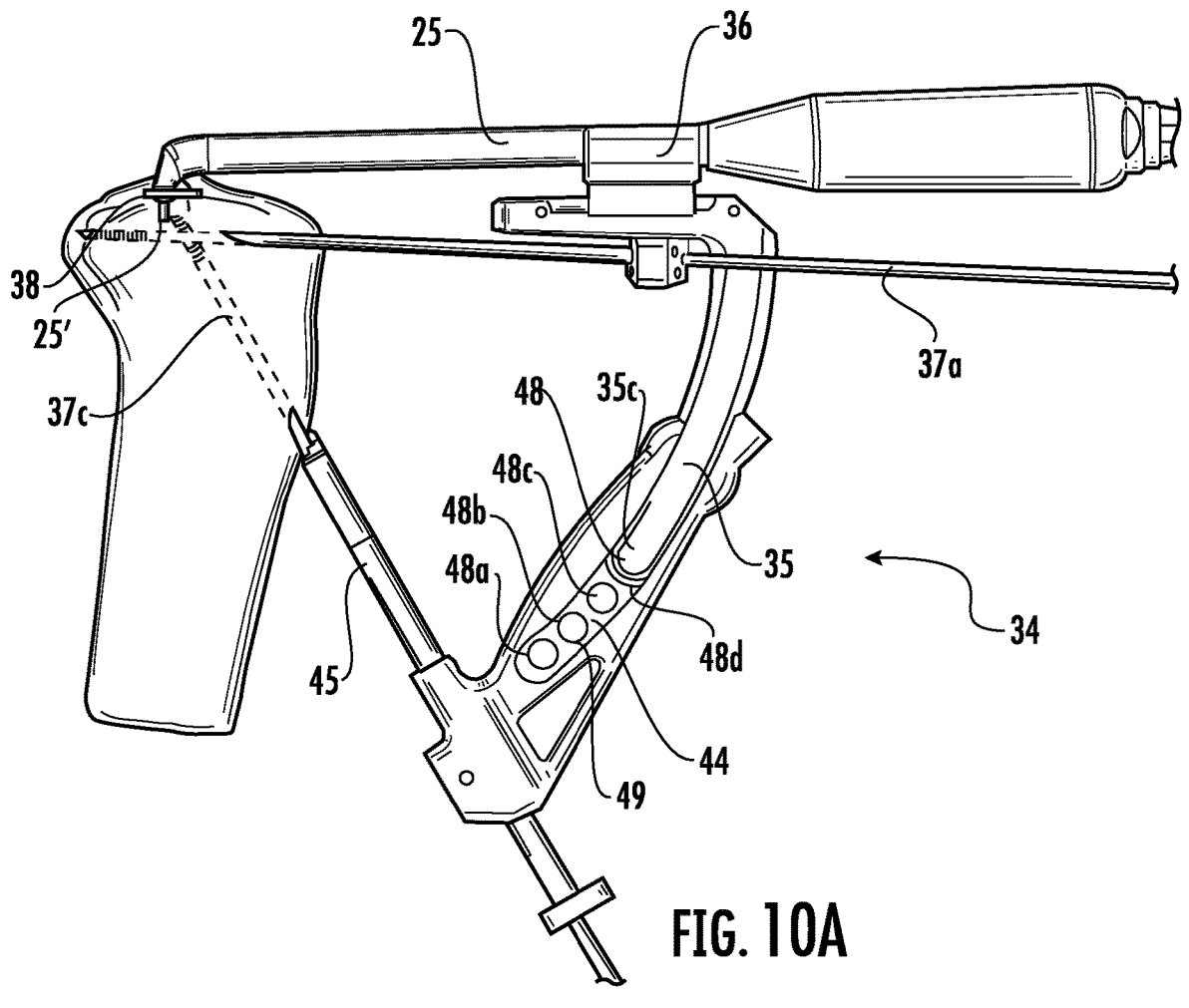
FIG. 10A is a side view of a surgical tool assembly and a drill.
Figure 10B:
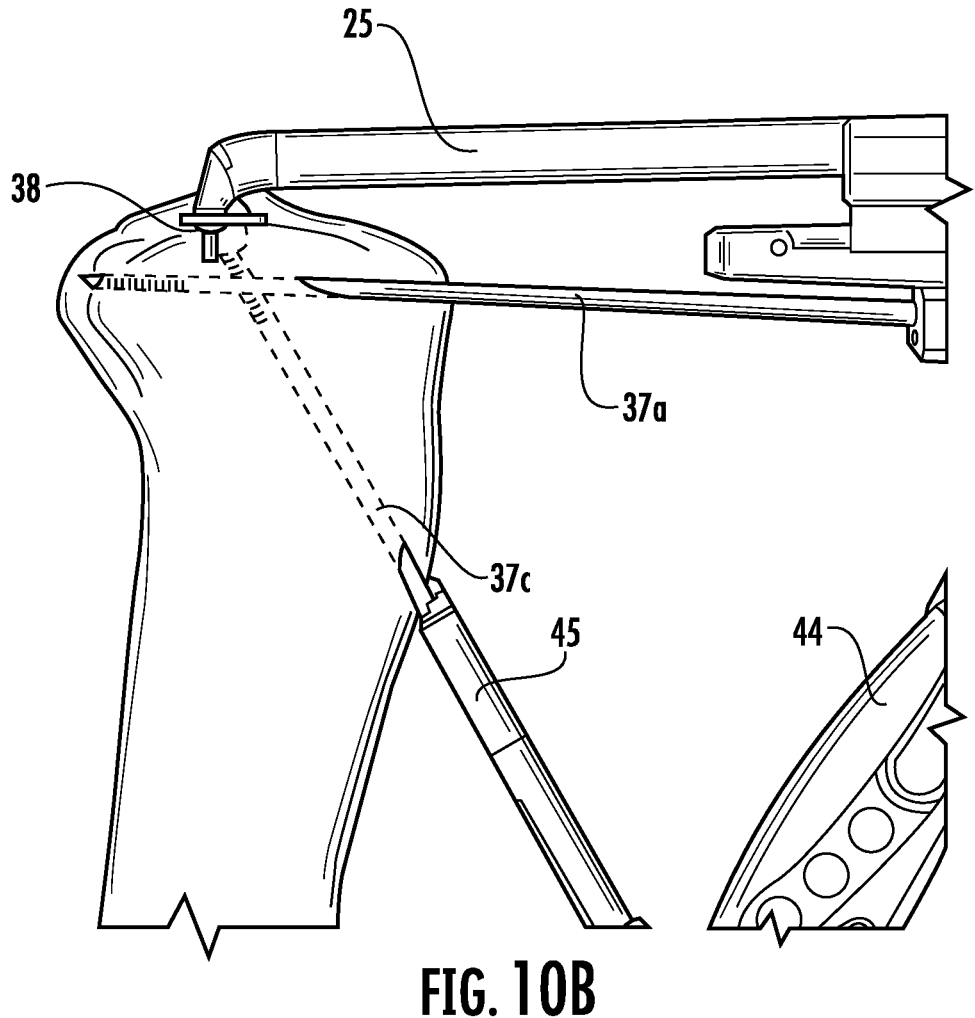
FIG. 10B is a magnified view of a portion of the surgical tool assembly and the drill engaged with a patient's anatomy.
Figure 10C:
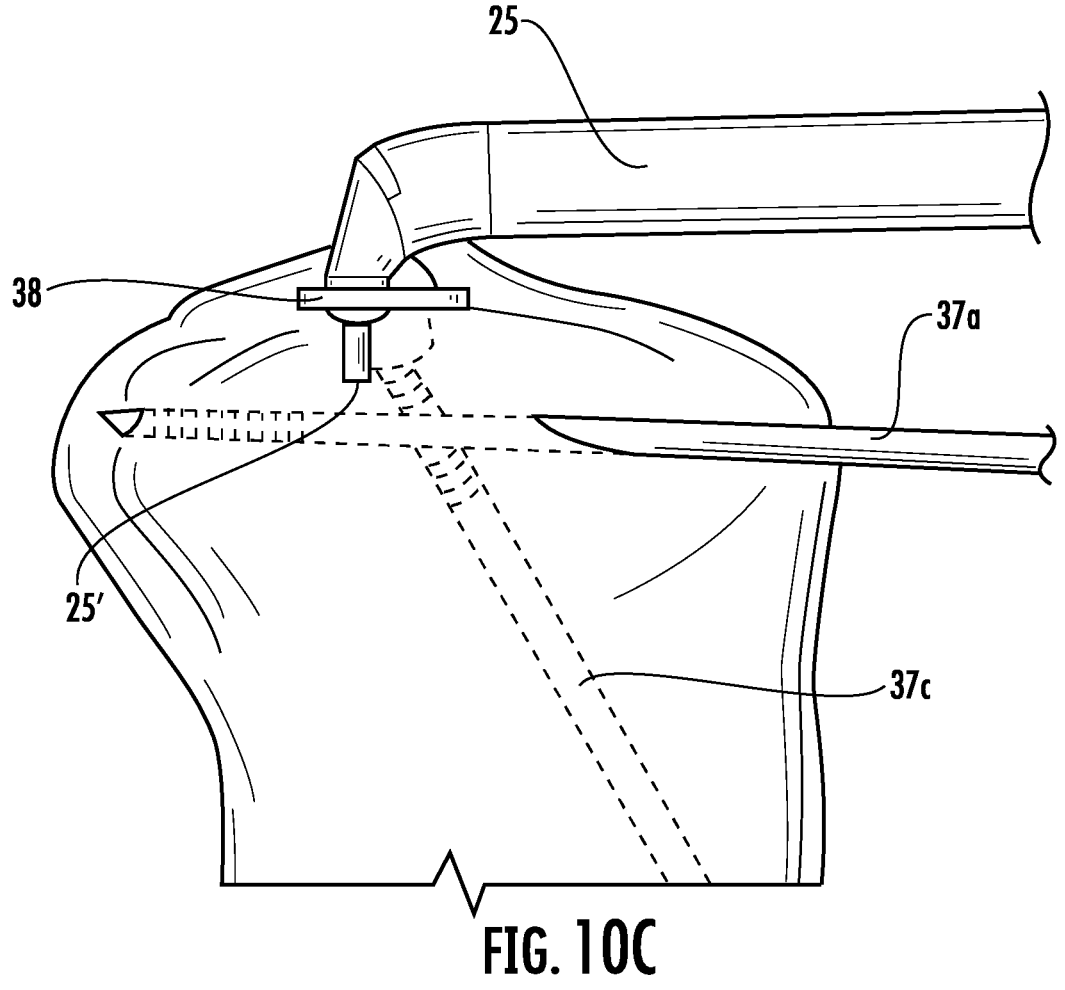
FIG. 10C is a further magnified view of a portion of the surgical tool assembly and the drill engaged with a patient's anatomy.
Figure 10D:
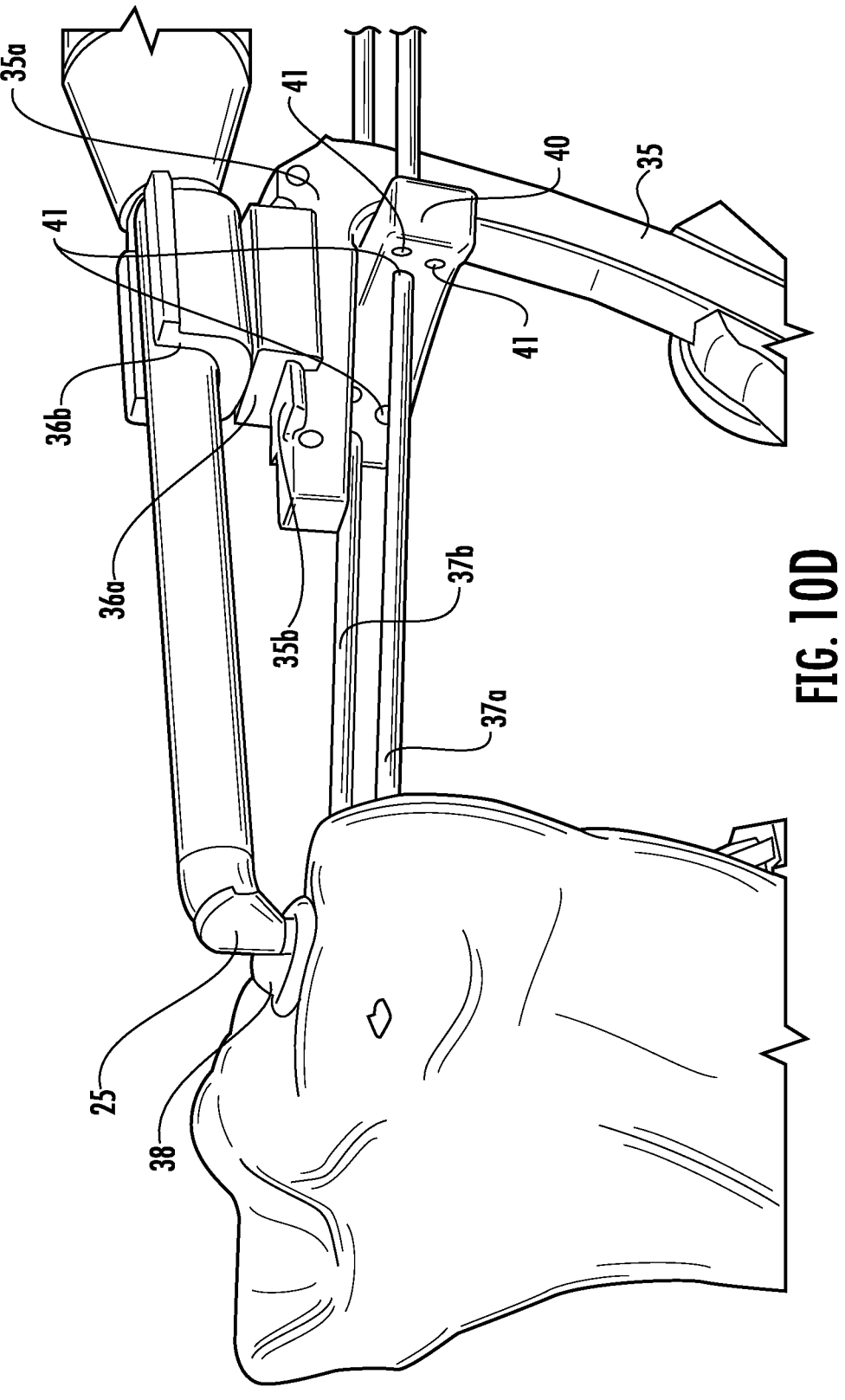
FIG. 10D is another view of the surgical tool assembly and the drill.

The first guide tool portion 35 includes a support or instrument guide assembly 36 for the drill 25, and a first support guide 40 dimensioned to allow passage of K-wires. A plurality of K-wires 37a, 37b, 37c can be provided to stabilize the surgical tool assembly 34. As shown in FIG. 10D, the first support guide 40 defines a plurality of openings 41 dimensioned to permit the K-wires to extend therethrough. The plurality of K-wires 37a, 37b, 37c can engage with the perimeter or edge of the openings 41 to secure the first support guide 40 in place.

The second guide tool portion 44 can be connected to the first guide tool portion 35 via an interface 48. The interface 48 can include a plurality of adjustment openings 48a, 48b, 48c, 48d that are configured to allow for relative adjustment between a connection of the first guide tool portion 35 to the second guide tool portion 44. For example, a terminal end 35c of the first guide tool portion 35 can include a prong or post configured to be received within the plurality of adjustment openings 48a, 48b, 48c, 48d. A track 49 can be defined on the second guide tool portion 44 that is dimensioned to receive a portion of the first guide tool portion 35, i.e. terminal end 35c. The track 49 can be formed as a slot or recess. A locking assembly 58, shown in FIG. 10H, can be provided to secure the first guide tool portion 35 with the second support guide 44. One of ordinary skill in the art would understand that various types of connections or interfaces can be provided between the first guide tool portion 35 and the second guide tool portion 44, such that a relative position between to the first guide tool portion 35 and the second guide tool portion 44 is adjustable.

The surgical tool assembly 34 can also include a cutting guide 38 (also referred to herein as a rotating drill guide or a pivot ball planar guide), which is described in more detail herein.

The second support guide 44 can include at least one opening configured to receive at least one K-wire, such as K-wire 37c. The second support guide 44 can be considered a stabilizing guide, in one aspect. In one aspect, the second support guide 44 can include a cannula 45 that defines an opening for the K-wire 37c. The K-wire 37 can be generally oriented at an oblique angle relative to the K-wires 37a, 37b that are supported by the first guide tool portion 35. The cannula 45 can have a ratcheted adjustment feature such that the cannula 45 can be manually adjusted within an opening defined by the second support guide 44 configured to support the cannula 45. For example, rotation of the cannula 45 in a first direction can extend the cannula 45 further from the second support guide 44 while rotation in a second, opposite direction can pull the cannula 45 backwards from the second support guide 44. An end of the cannula 45 can have an engagement surface configured to help secure the cannula 45 against a portion of the patient's anatomy.

In this arrangement, triangulation targeting of the desired joint surface implant recipient site is controlled. At least one K-wire 37c can engage the cutting guide 38, which restricts and guides the right-angle drill 25 relative to the desired recipient site. At least two additional K-wires 37a, 37b can be used to stabilize the first guide tool portion 35 relative to the joint surface recipient site. In one aspect, an angle defined between the K-wire 37c and either one of the other two K-wires 37a, 37b is between 45 degree to 80 degrees. One skilled in the art would understand that this angle will vary due to multiple parameters.

The instrument guide assembly 36 limits or restricts sliding and rotation of the drill 25. The instrument guide assembly 36 can include a slider 36a slidably secured on a base portion 35a of the first guide tool portion 35. In one aspect, the base portion 35a of the first guide tool portion 35 defines a track 35b having a predetermined stoke or length for the slider 36a to slide along. A support interface 36b can be pivotably secured to the slider 36a and include a channel or receptacle for attaching to the drill 25. The drill interface may be formed as U-shaped bracket or holder dimensioned to engage a portion of the drill 25. This arrangement provides for sliding and rotational movement of the drill 25, and ensures that the stroke or movement of the drill 25 is restricted to a predetermined geometry.

The surgical tool assembly 34 can both provide stability and orientation via providing openings for K-wires (i.e. K-wires 37a, 37b, 37c) and can also provide the ability to control movement of the drill 25.

The recipient site with the exposed joint bearing surface damage can be prepared or treated with a round burr in the center of the damage. The cutting guide 38 (which is also referred to as a platform guide, or rotating drill guide) is configured to rest or sit in a half round or spherical depression created by the burr and can be stabilized by a flat disc 39 that extends around a perimeter of the cutting guide 38. In one aspect, the cutting guide 38 is coated with a hydrogel or soft durometer polymer to protect the perimeter cartilage, and is leveled to the circumferential contiguous cartilage surface through compression with both the engaged K-wire 37c and the first guide tool portion 35.

Figure 10E:
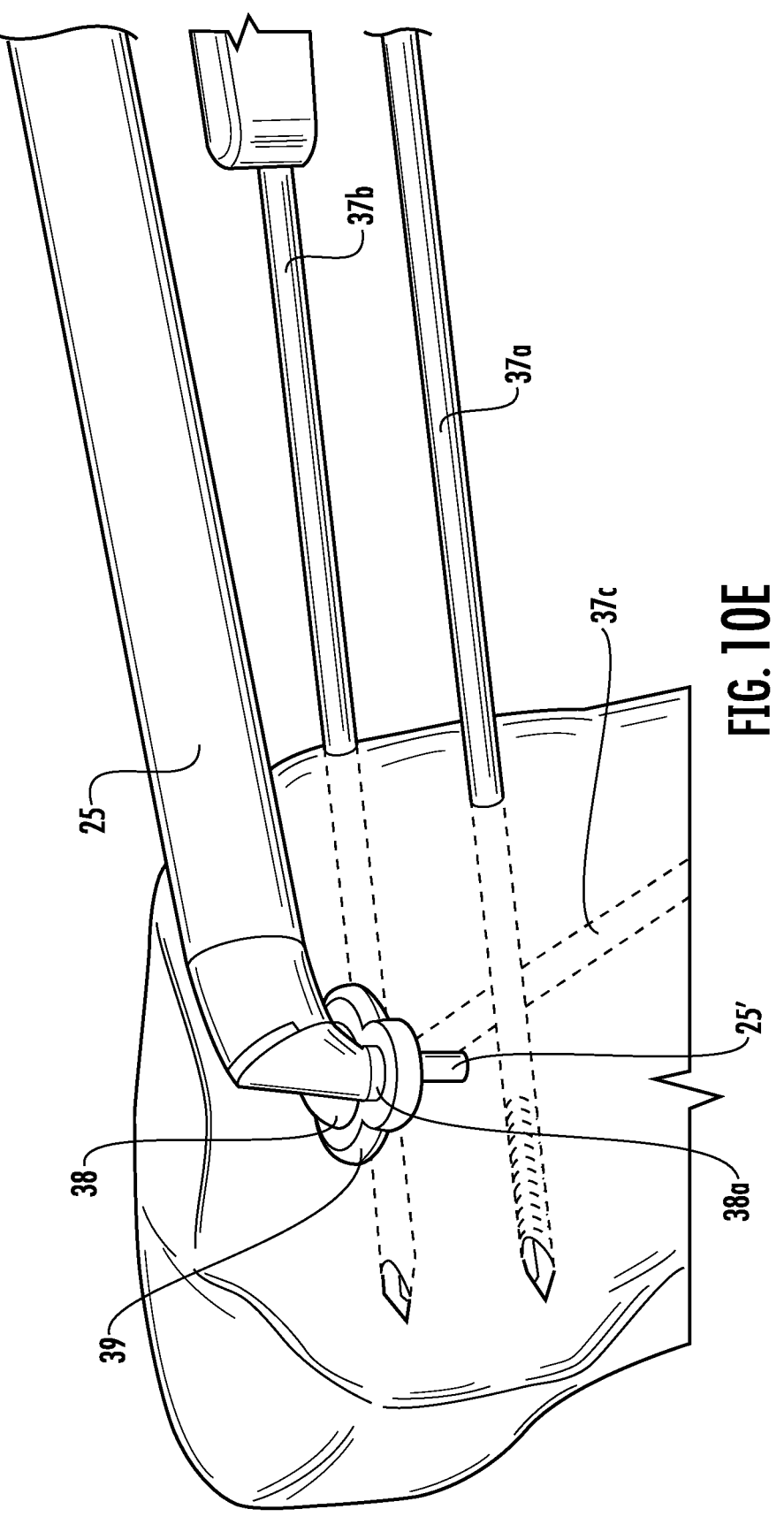
FIG. 10E is a perspective view of a portion of the surgical tool assembly and the drill engaged with a patient's anatomy.
Figure 10F:
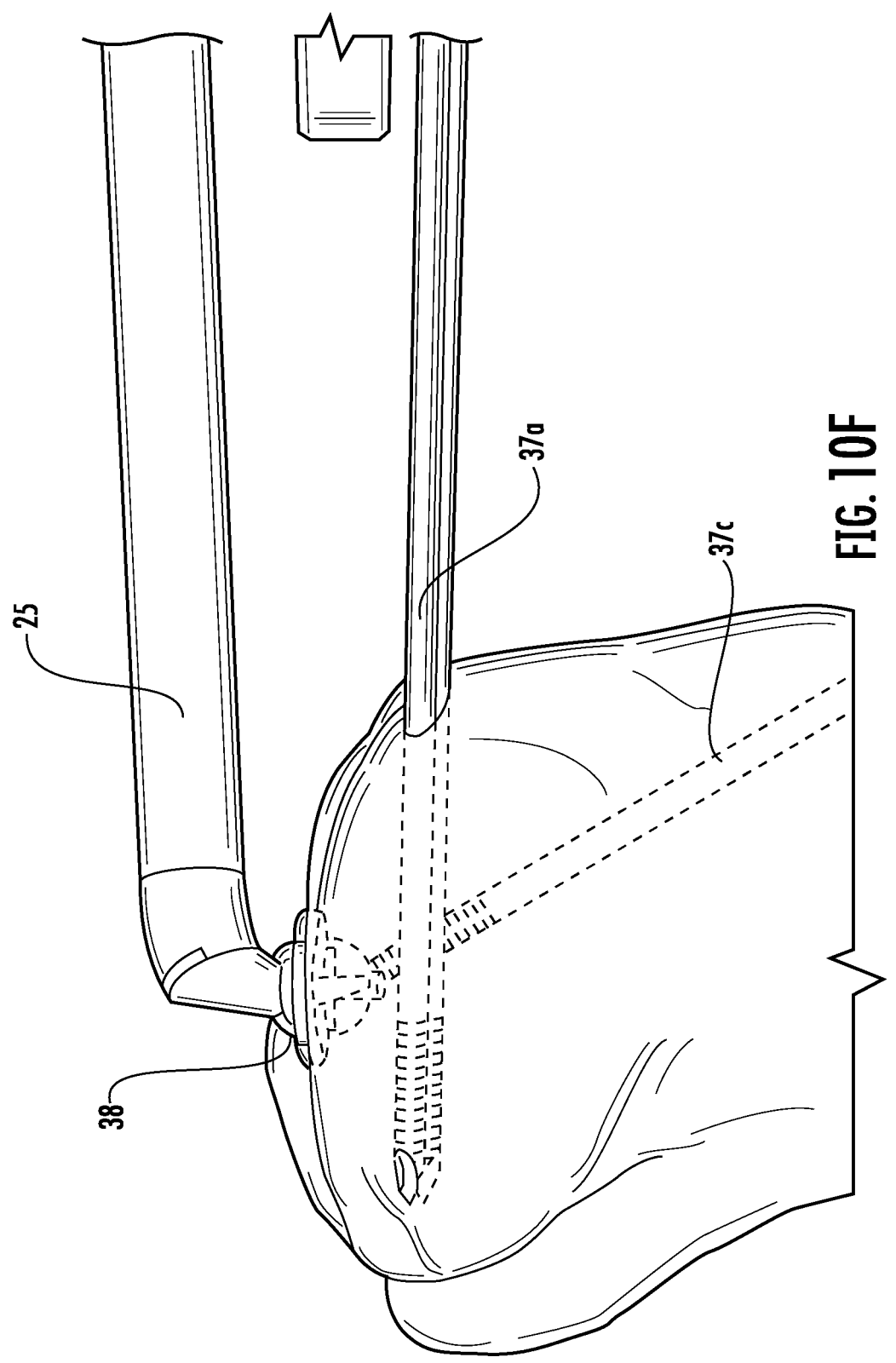
FIG. 10F is a side view of a portion of the surgical tool assembly and the drill engaged with a patient's anatomy.
Figure 10G:
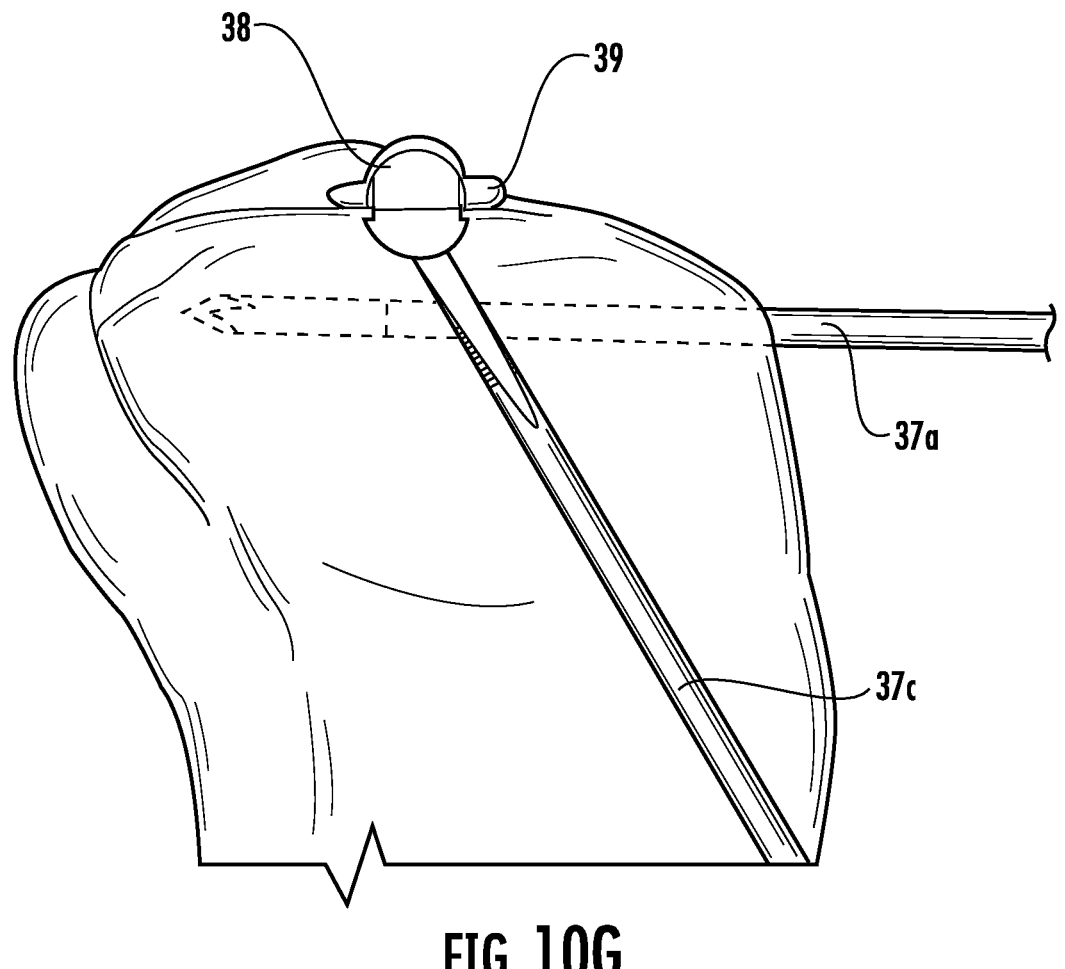
FIG. 10G is a cross-sectional view of a portion of the surgical tool assembly and the drill engaged with a patient's anatomy.
Figure 10H:
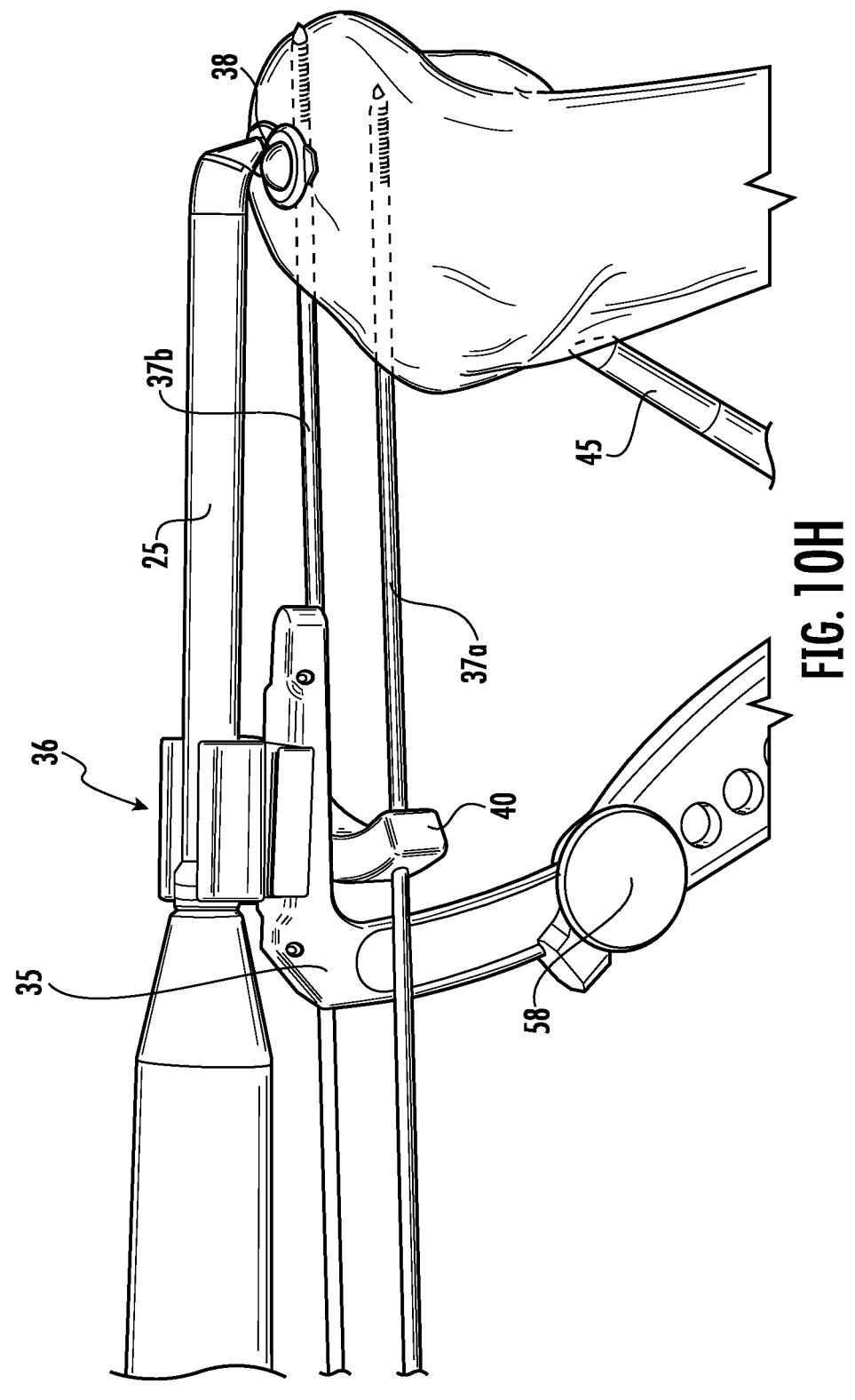
FIG. 10H is another side view of the surgical tool assembly and the drill.
Figure 10I:
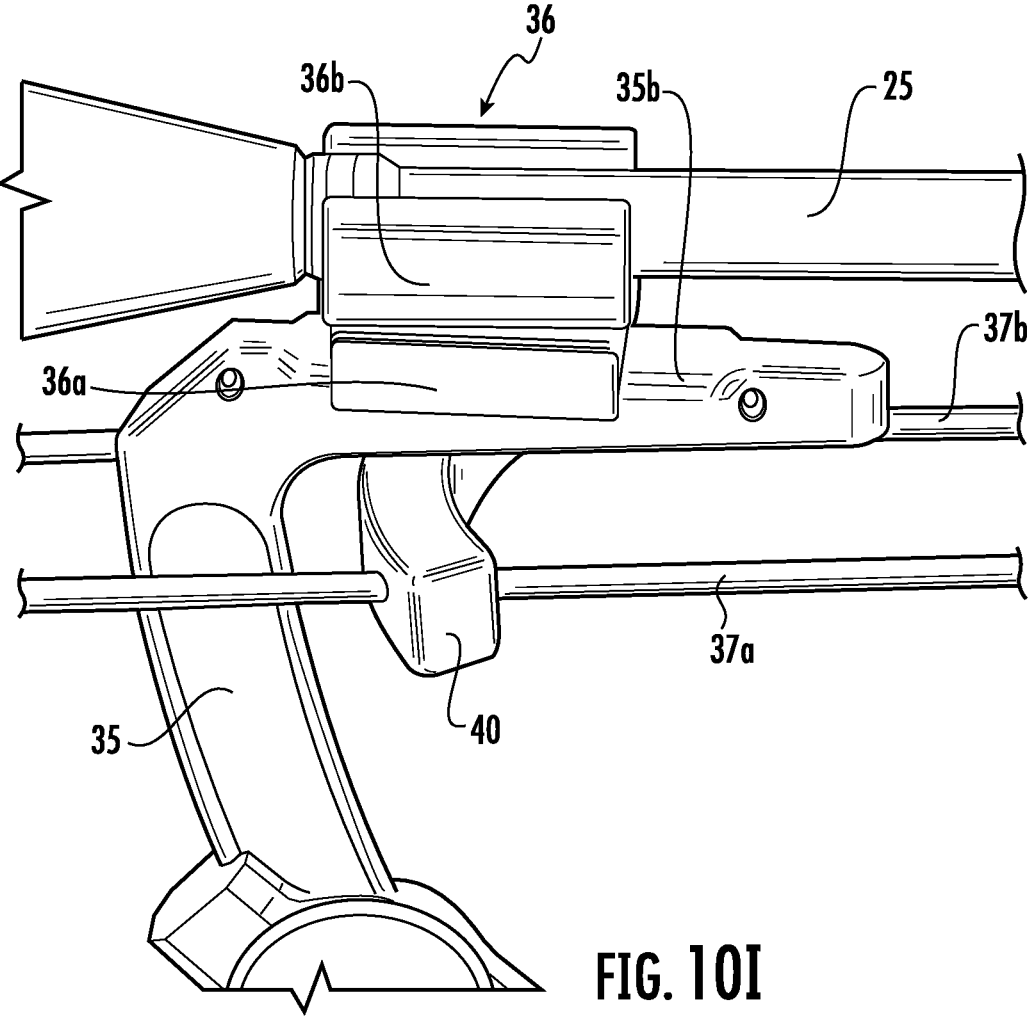
FIG. 10I is a magnified view of a portion of the surgical tool assembly.
Figure 10J:
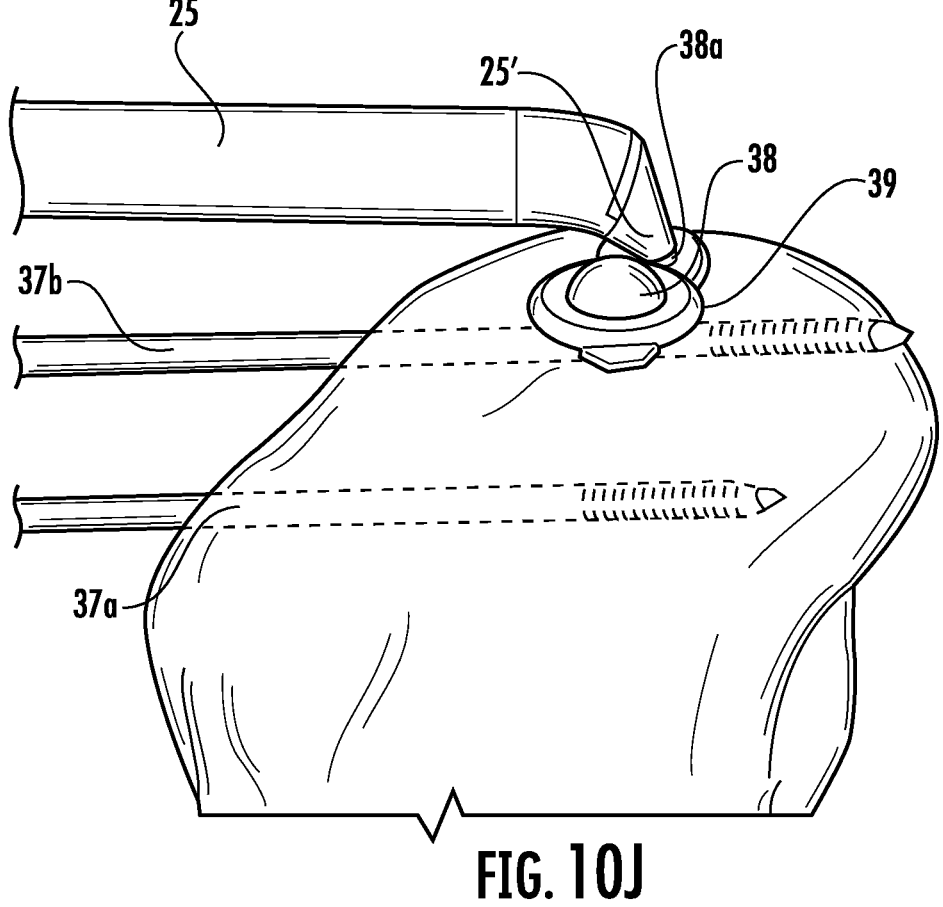
FIG. 10J is a magnified view of an interface between the drill and the patient's anatomy.
Figure 11A:
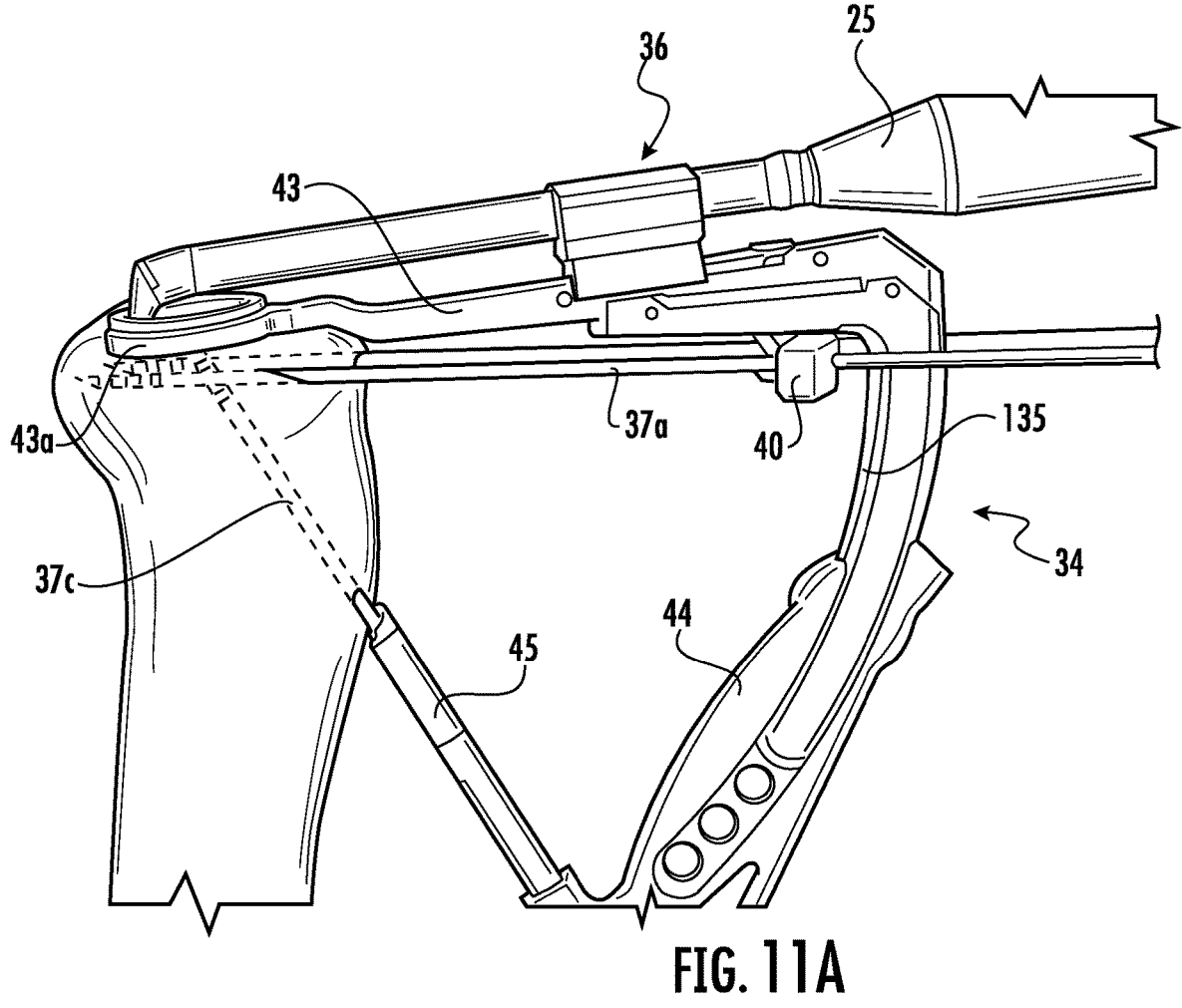
FIG. 11A is a side view of another surgical tool assembly and drill.
Figure 11B:
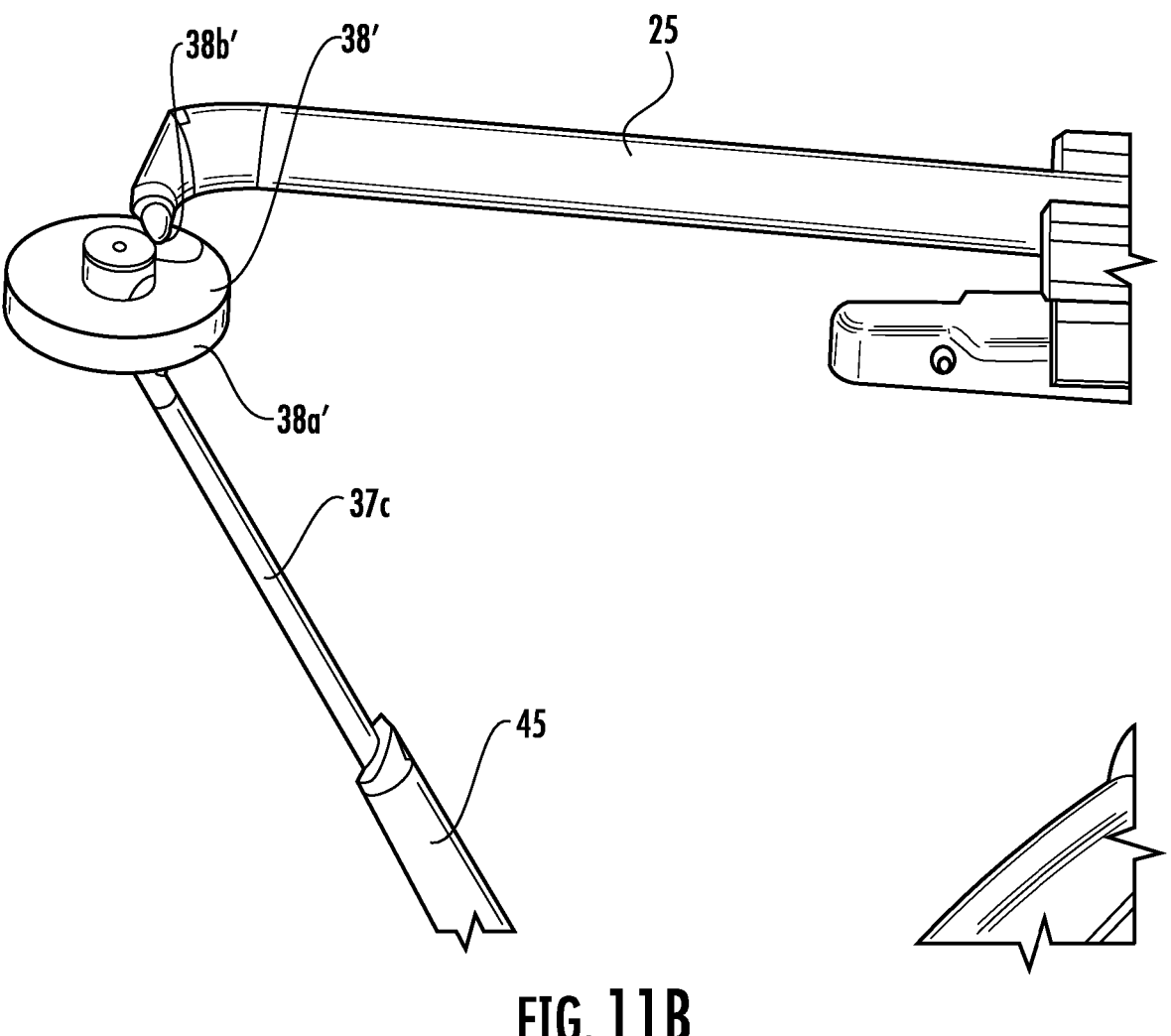
FIG. 11B is a magnified view of a rotary planar guide engaged with the drill.
Figure 11C:
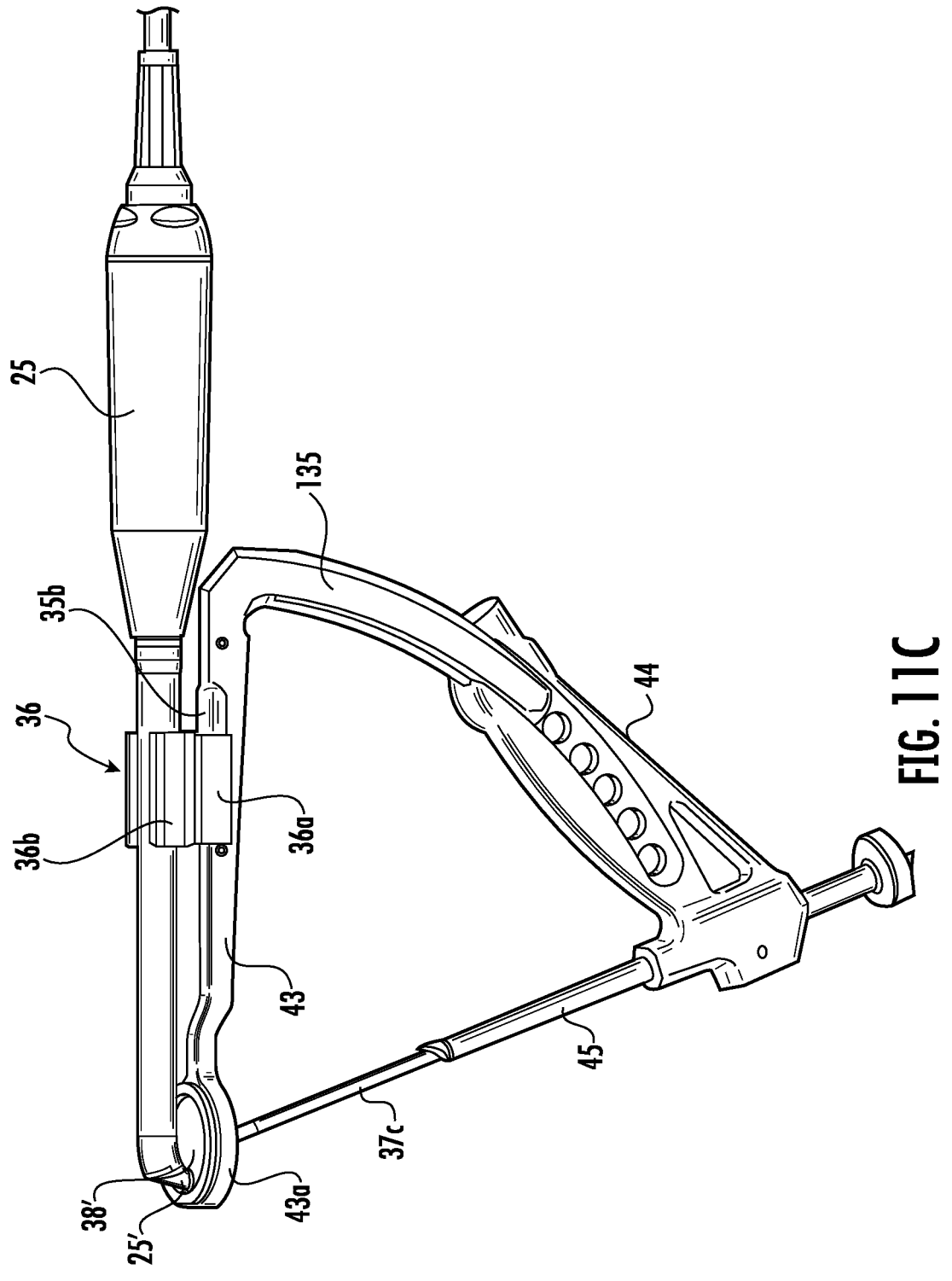
FIG. 11C is another side view of the surgical tool assembly and drill.
Figure 11D:
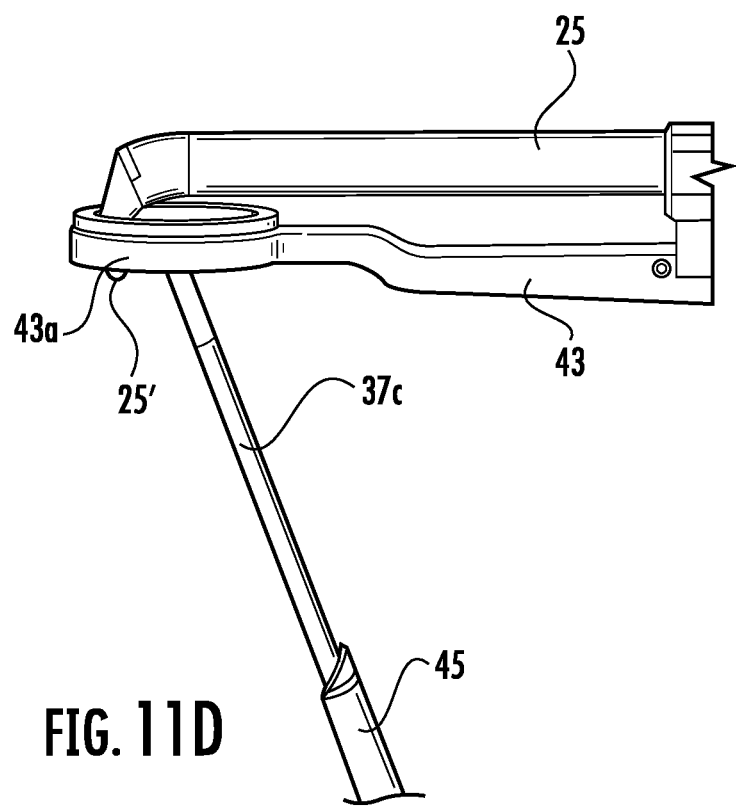
FIG. 11D is a side view of one area of the surgical tool assembly and the drill.
Figure 11E:
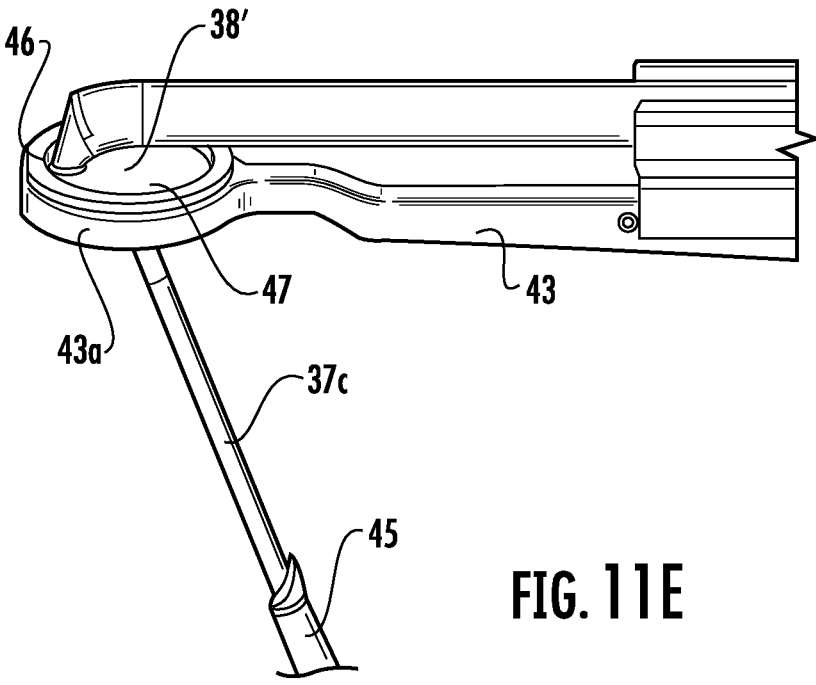
FIG. 11E is another view of one area of the surgical tool assembly and the drill.

The cutting guide 38 is configured to be coupled with the end of the drill 25 in one aspect, as shown in FIG. 10E. The cutting guide 38 can include an opening 38a configured to receive an end 25' (i.e. a cutting or drilling end) of the drill 25. In one aspect, the opening 38a is formed on a side protrusion extending radially from a main portion of the flat disc 39 perimeter. The cutting guide 38 can first be placed in the patient's anatomy, and then a surgeon can insert the end 25' of the drill 25 into the opening 38a of the cutting guide 38. The cutting guide 38 is configured to restrict the pathway of the end 25' of the drill 25. Based on this configuration, a cutting path of the drill 25 is limited to a predetermined geometry (i.e., a periphery of the cutting guide 38). One skilled in the art would understand that the shape of the cutting guide 38 can vary. The cutting guide 38 can act as a pivot ball planar guide, in one aspect.

The cutting guide 38 is configured to be compressed on one side (i.e., downward) by the drill 25 and compressed on a second side (i.e., upward) by the K-wire 37c. The drill 25 is then configured to cut in a circular pattern or geometry as defined by the circumference or profile of the cutting guide 38. The cutting guide 38 can act as a tracing component that defines a cutting path for the drill 25. One of ordinary skill in the art would understand that the cutting guide 38 can be used with any other embodiment disclosed herein.

As shown in FIGS. 11A-11E, a rotary planar guide 38' can be provided for a surgical tool assembly 134. The rotary planar guide 38' can be one variation of the cutting guide 38. The rotary planar guide 38' is configured to sit in the half round or spherical depression created by a burr in a patient's anatomy and is stabilized by a flat ring or perimeter 38a'. The rotary planar guide 38' includes an opening 38b' configured to receive the cutting end 25' of the drill 25, and is configured to guide the cutting end 25'. The ring or perimeter 38a' of the rotary planar guide 38' can be coated with a hydrogel or soft durometer polymer to protect the perimeter cartilage of the patient, and can be leveled to the circumferentially contiguous cartilage surface through compression with the K-wire 37c and the first guide tool portion 135, and/or the drill 25.

In one aspect, a guide arm 43 can extend from a main portion of the first guide tool portion 135. The guide arm 43 can extend in a perpendicular or tangential direction relative to the patient's recipient site for the implant. All other aspects of the first guide tool portion 135 of FIGS. 11A-11E are similar to the first guide tool portion 35 of FIGS. 10A-10J. An end 43a of the guide arm 43 can define a receptacle 47 for receiving or supporting the rotary planar guide 38'. In each of the embodiments disclosed herein, the end 43a can be considered a target guide. The target guide is generally configured to engage with the surface surrounding the defect in the patient.

A coupler 46 can be provided to connect the end 43a of the guide arm 43 with the rotary planar guide 38'. The coupler 46 can include a snap-fit ring or cap that is configured to secure the rotary planar guide 38' to the guide arm 43. One of ordinary skill in the art would understand that other structures, fasteners, couplers, and arrangements could be used to ensure that rotary planar guide 38' is secured to the guide arm 43. The rotary planar guide 38' is rotationally free when supported on the guide arm 43 by the coupler 46, such that a surgeon can rotate the rotary planar guide 38' to perform further cutting or drilling in a predetermined path based on the opening 38b' defined by the rotary planar guide 38'. The coupler 46 is configured to rotate around the edge of the end 43a of the guide arm 43, in one aspect, in order to provide more control of the cutting end 25' on the edge of the implant site to optimize the recipient patient site wall for the subsequent press fit with the implant 10.

As shown in FIGS. 12A-12F, the guide tool assembly 134 can be adapted for use without a rotary planar guide. Based on this arrangement, the cutting end 25' of the drill 25 is configured to freely move within the confines of a predetermined outer perimeter shape, as compared to being fixed to a predetermined path when attached or engaged with the rotary planar guide 38' or the cutting guide 38. In this aspect, the end 43a of the guide arm 43 defines a circular perimeter, guide ring, or receptacle 47 that is configured to limit the path of the cutting end 25' of the drill 25. The end 43a of the guide arm 43 with the receptacle 47 is configured to sit on the worn-out joint surface and is stabilized by its flat perimeter, which may be coated in a hydrogel or soft durometer polymer to protect the perimeter cartilage, and is leveled to the circumferential contiguous cartilage surface, through compression with the engaged K-wires and the guide tool or drill. All other aspects of the guide tool assembly 134 as shown in FIGS. 12A-12F are otherwise similar to the guide tool assembly 34 as illustrated in FIGS. 10A-10J, and the guide tool assembly 134 as illustrated in FIGS. 11A-11E.

Figure 12A:
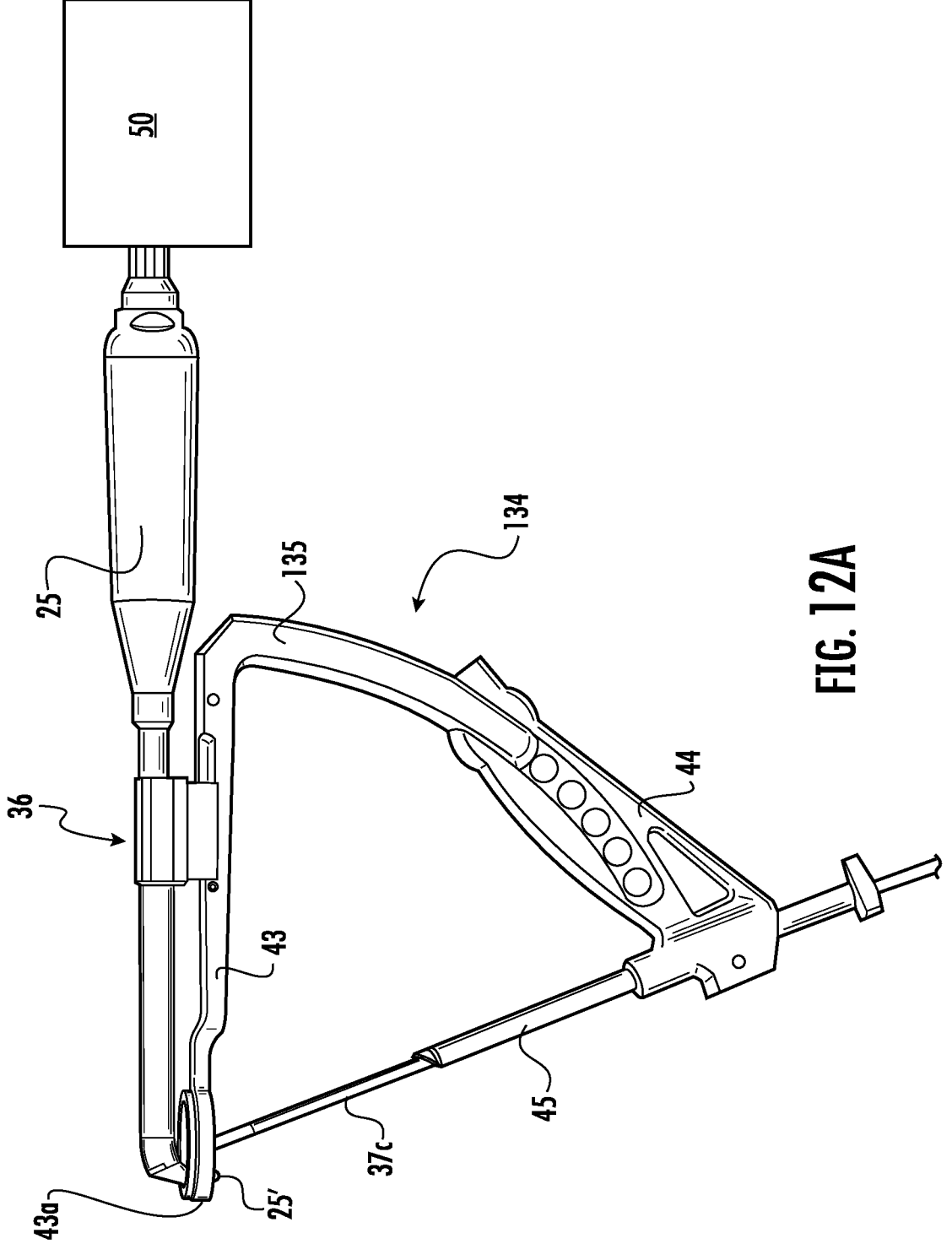
FIG. 12A is a side view of a surgical tool assembly interfacing with a robotic system.
Figure 12B:
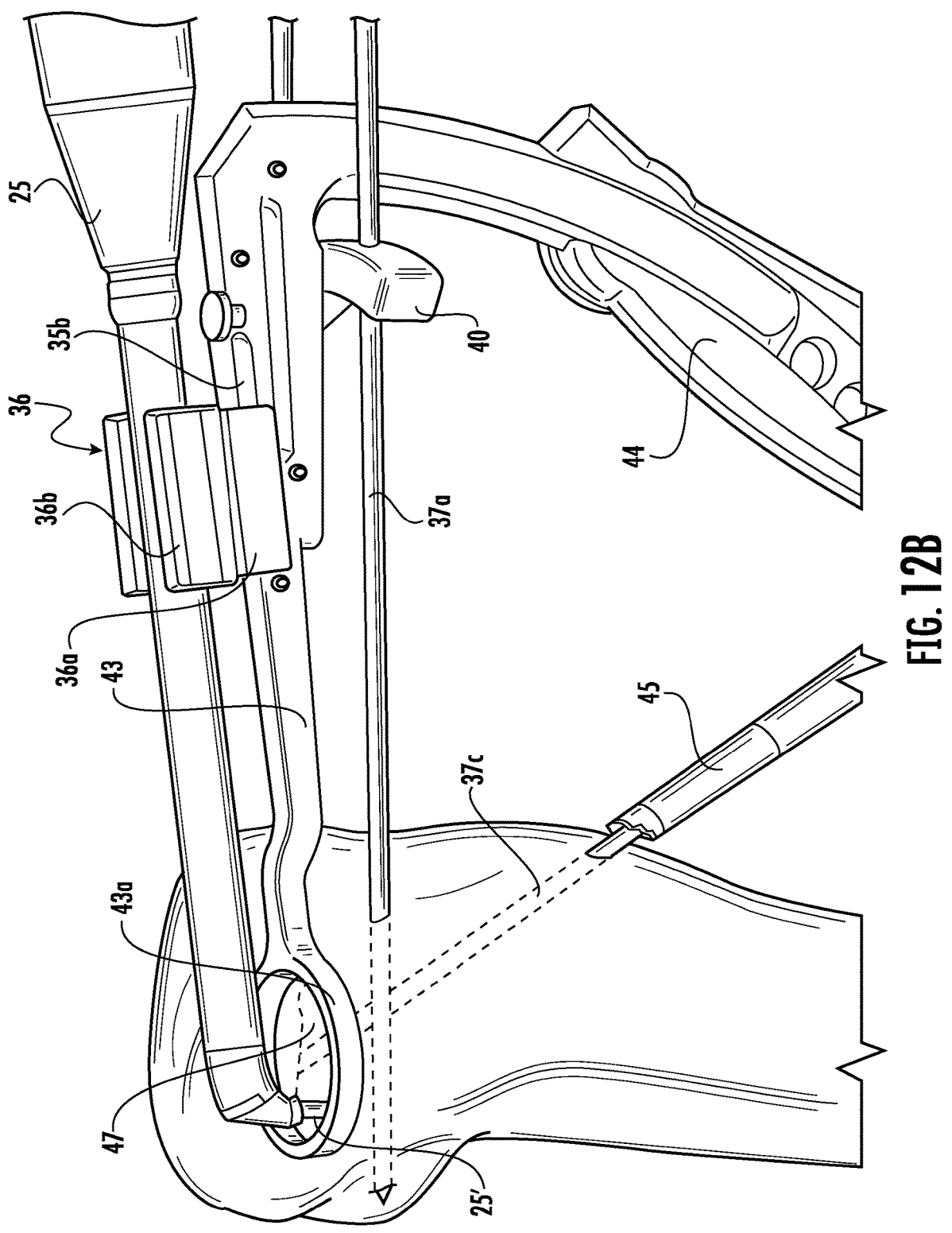
FIG. 12B is a side perspective view of one area of the surgical tool assembly and the drill engaged with a patient's anatomy.
Figure 12C:
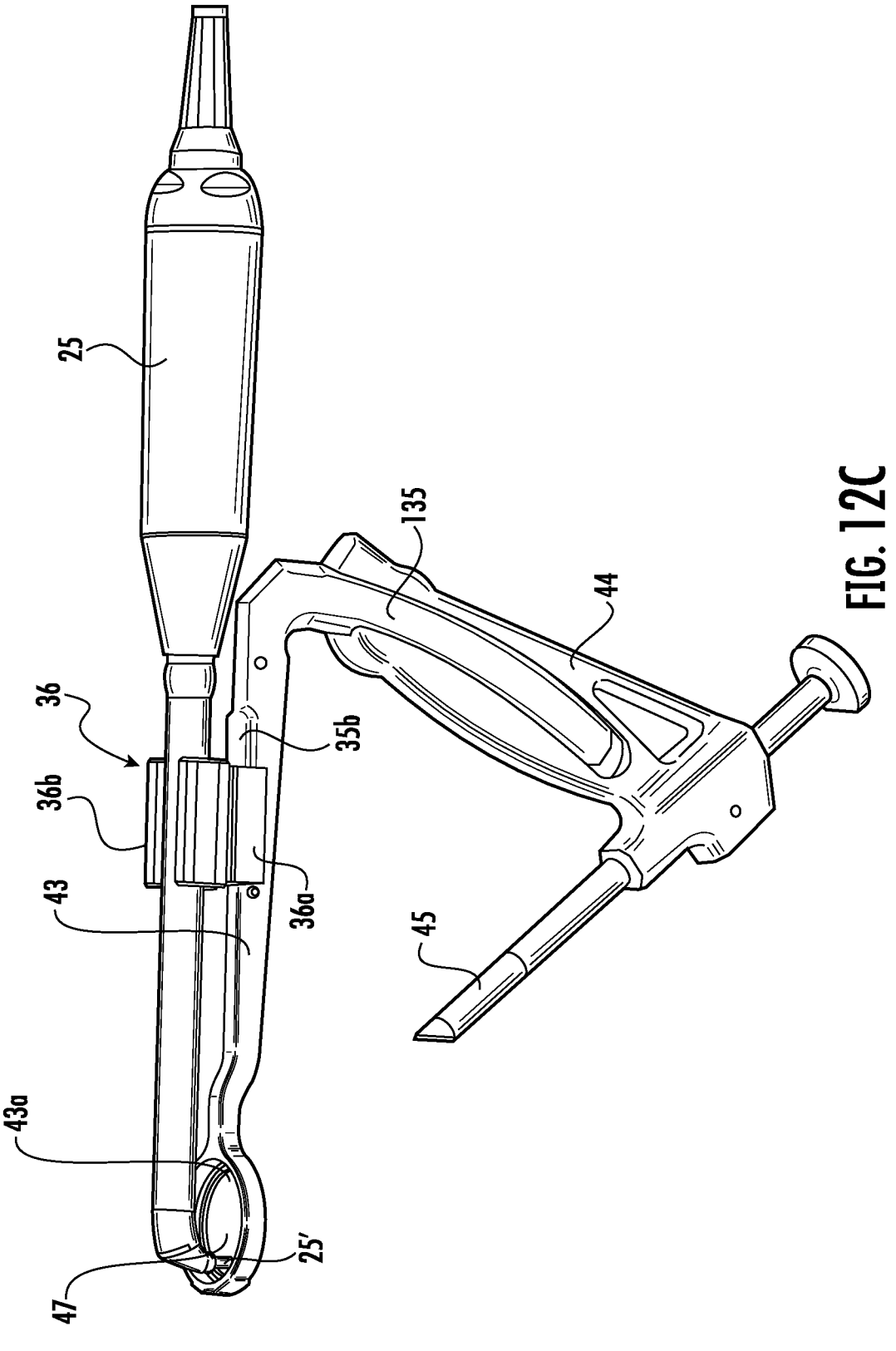
FIG. 12C is another side perspective view of the surgical tool assembly and the drill.
Figure 12D:
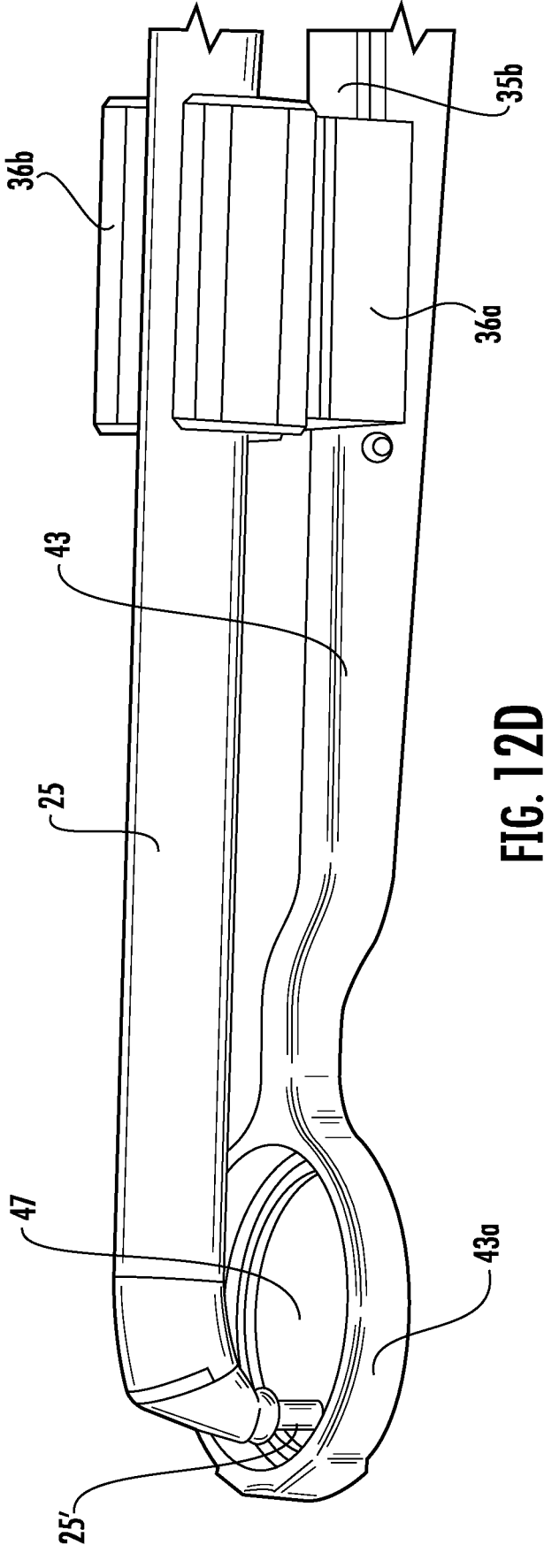
FIG. 12D is a magnified view of one area of the surgical tool assembly and the drill.
Figure 12E:
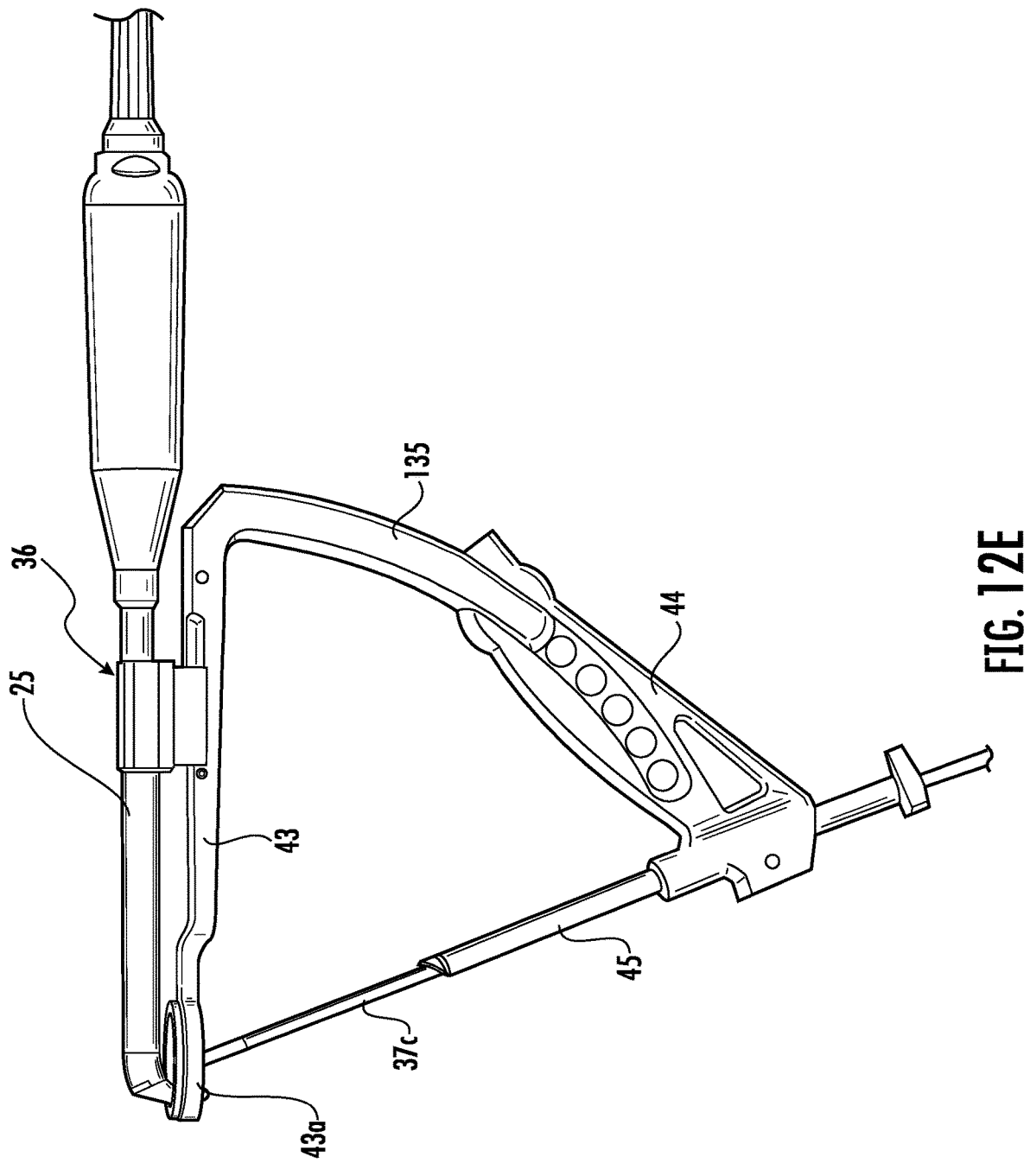
FIG. 12E is a side view of the surgical tool assembly and the drill.
Figure 12F:
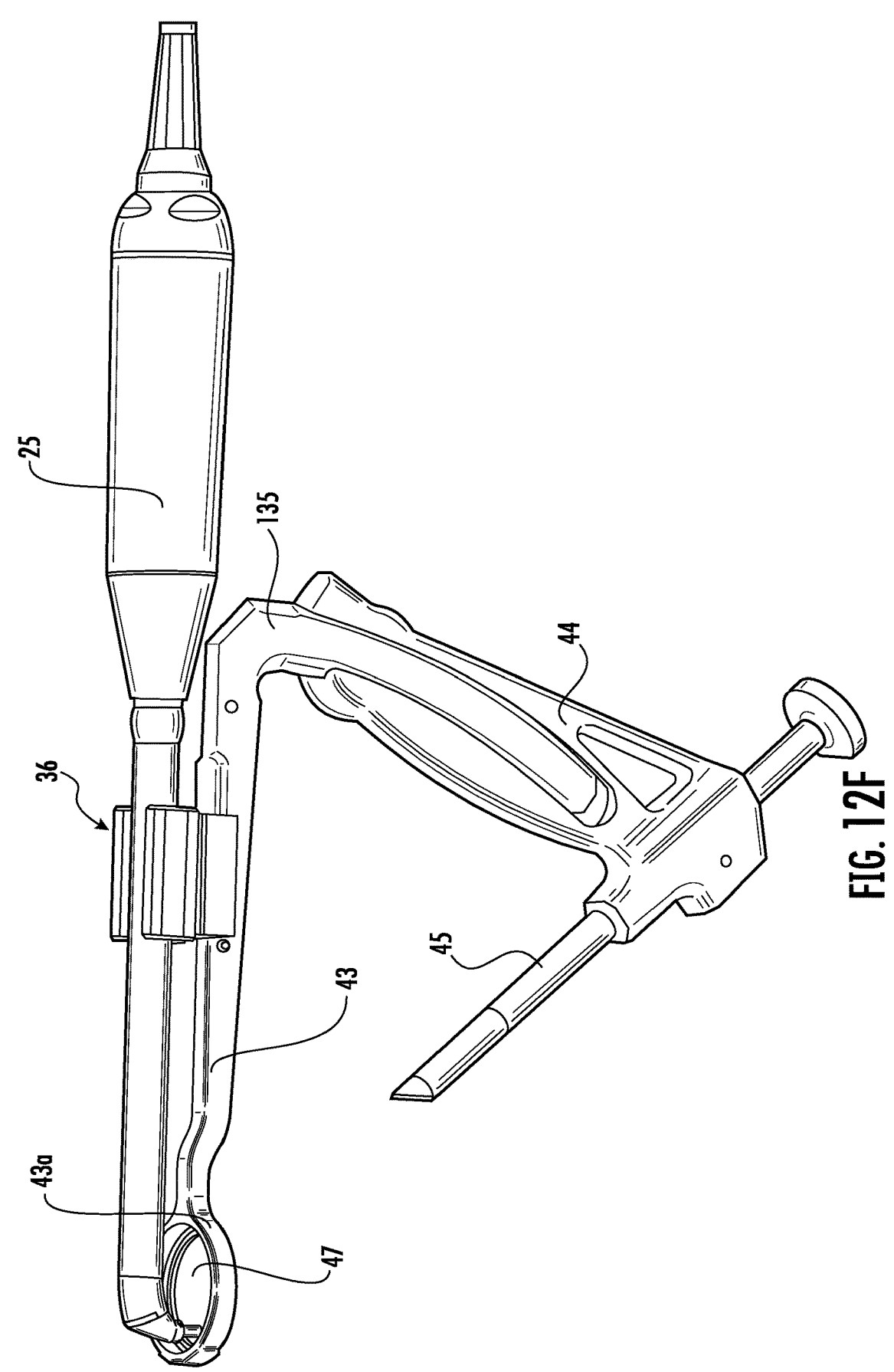
FIG. 12F is another side view of the surgical tool assembly and the drill.

In one aspect, a robotic system 50 can be configured to drive movement of the drill 25, as shown schematically in FIG. 12A. As used herein, a robotic system refers to any electrical, mechanical, and/or electromechanical system, which may be configured to perform activity such as cutting, drilling, moving another component, imaging, modeling, indexing, etc. In one aspect, the robotic system 50 is configured to perform activity with limited human intervention, and can be semi-autonomous or fully autonomous. The robotic system 50 can be computerized, and can include a processor configured to control functions of the robotic system, as well as an input/output interface or controller, memory, CPU, and/or other electrical components.

This robotic system 50 can be implemented within any one of the configurations disclosed herein. The robotic system 50 can be configured to ensure that the drill 25 does not cut outside of the container or receptacle 47. Additionally, indexing of the patient anatomy can be achieved by using a combination of the surgical tool assembly 34 and the robotic system 50.

In one aspect, the robotic system 50 is configured to be coupled with any portion of the guide components disclosed herein. In one aspect, the robotic system 50 can be used without the guide components that are configured to control the terminal end of the instrument, such as elements 38, 38', 47, etc., because the robotic system 50 can be automatically driven to control the burr/drill excursion within the targeted recipient site. The target guide, being indexed directly to and coupled with the robotic system 50, obviates the need for indexing the surface anatomy, because the surgeon centers the guide over the target recipient site, stabilizes it with k-wires and the guide simply targets and/or marks the site for the robotic system 50 or instrument 25 to create the desired recipient site with specific dimensions programmed into the robotic system 50 for the desired specific implant, with its specific guide.

In one aspect, the robotic system 50 can be configured to index the patient's anatomy based on movement of the drill 25. Based on the predetermined cutting path or pattern provided by any one of the guiding elements disclosed herein (i.e. guide interface 26c, receptacle 28, cutting guide 38, rotary planar guide 38', receptacle 47, the receptacle 235d, and/or the instrument guide assembly 36, etc.), the tools can act as an indexing assistance system for any robotic system 50. The robotic system 50 can be configured to have a probe or other device that is systematically moved and location and position information is generated during said movement. The robotic system 50 can generate an accurate array or image of the patient's anatomy by being limited in its movement using the tools disclosed herein. Therefore, indexing can be more reliably and accurately achieved as compared to a robotic system 50 that is not being limited or guided by the tools disclosed herein.

Figure 13A:
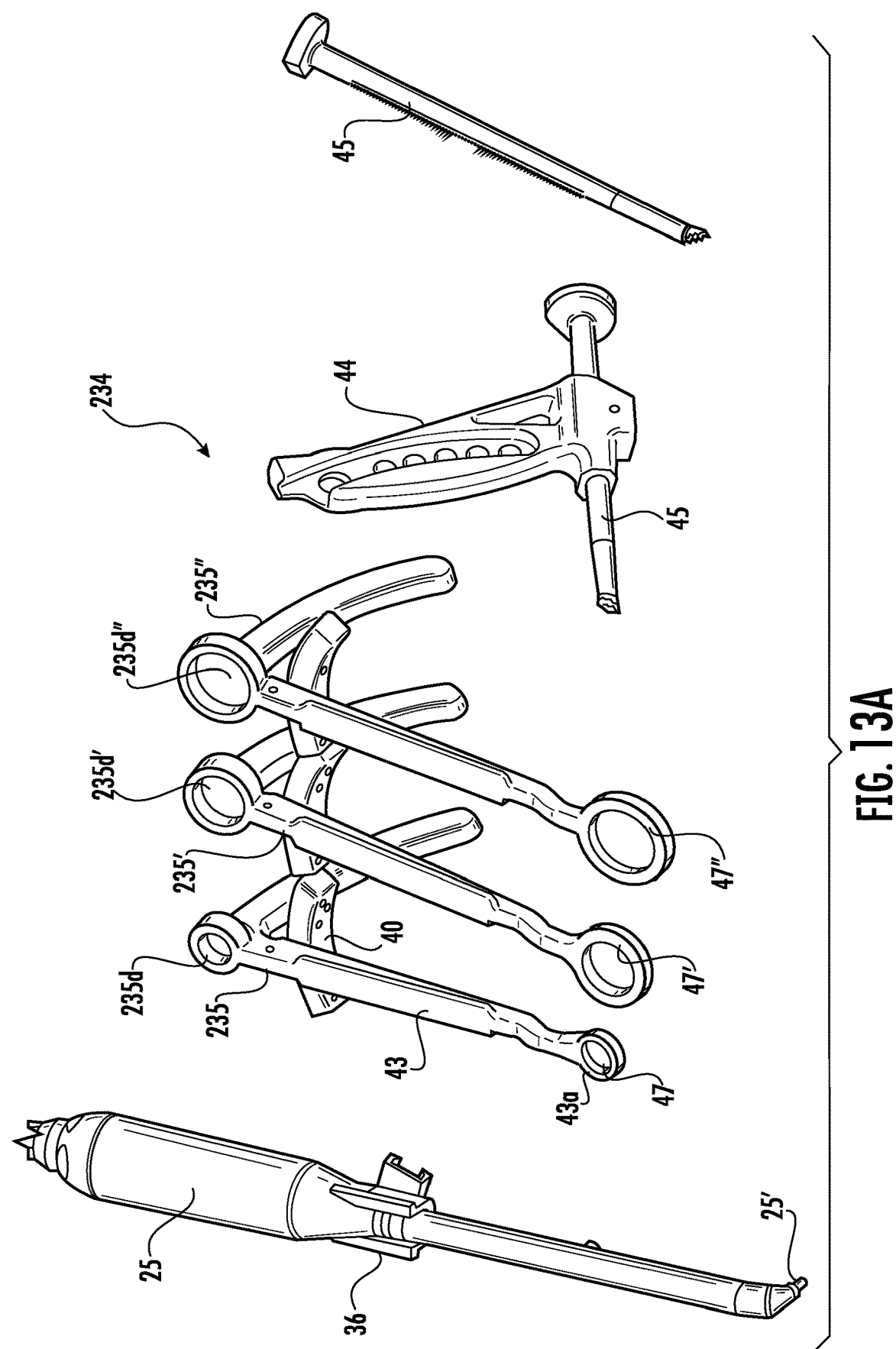
FIG. 13A illustrates a surgical tool assembly.
Figure 13B:
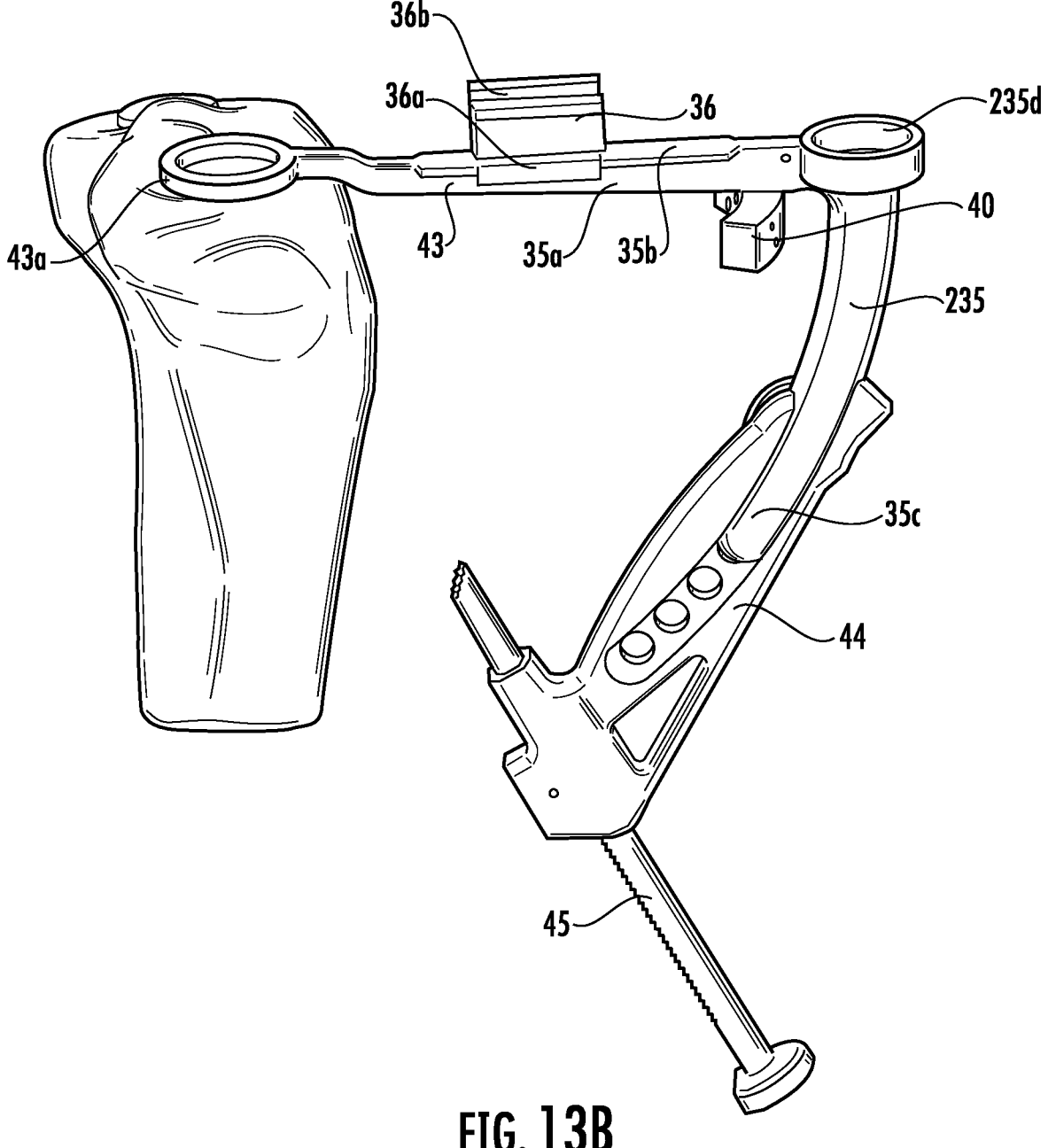
FIG. 13B is a side perspective view of the surgical tool assembly engaged with a patient's anatomy in a first state.
Figure 13C:
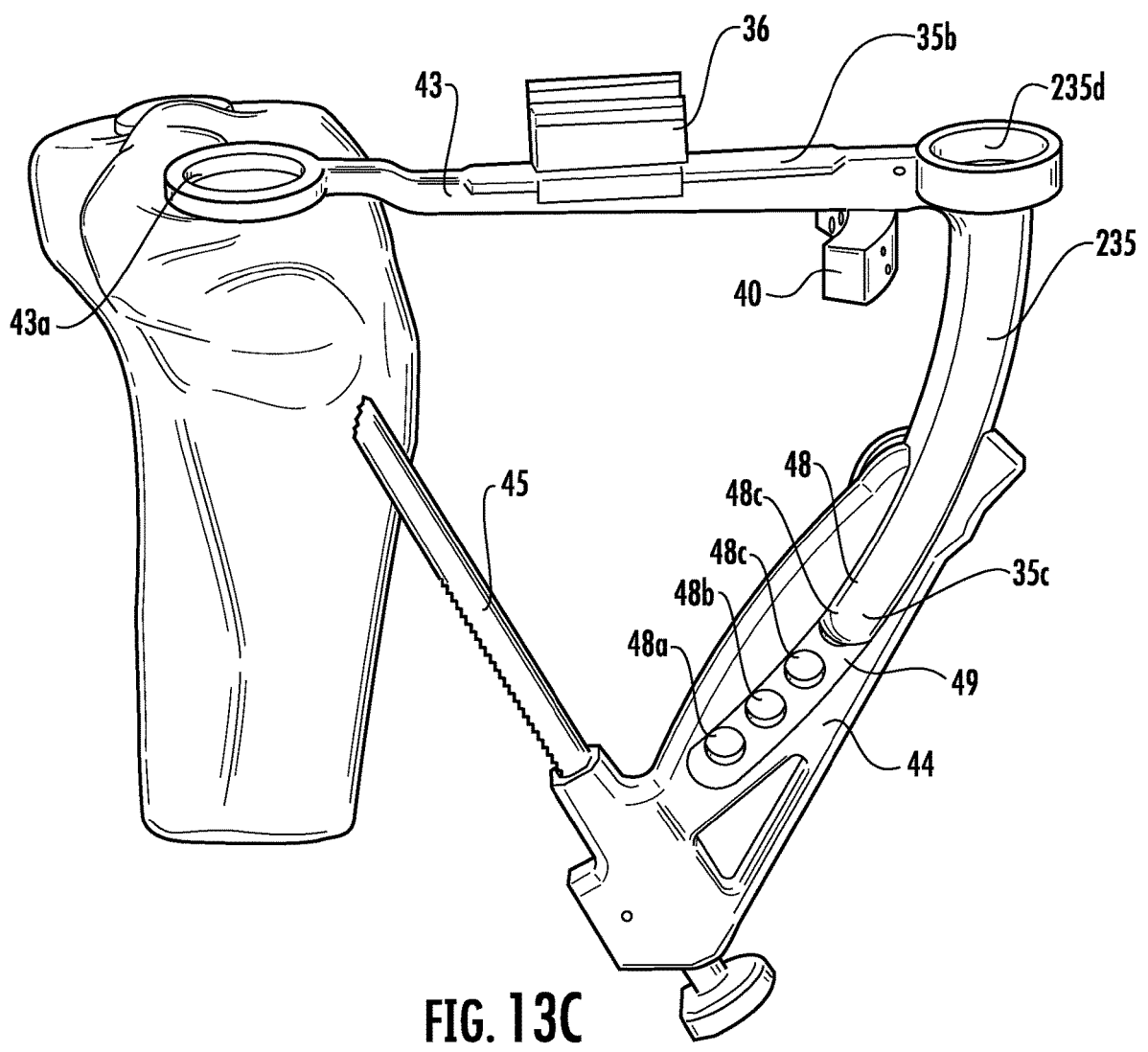
FIG. 13C is a side perspective view of the surgical tool assembly engaged with a patient's anatomy in a second state.
Figure 13D:
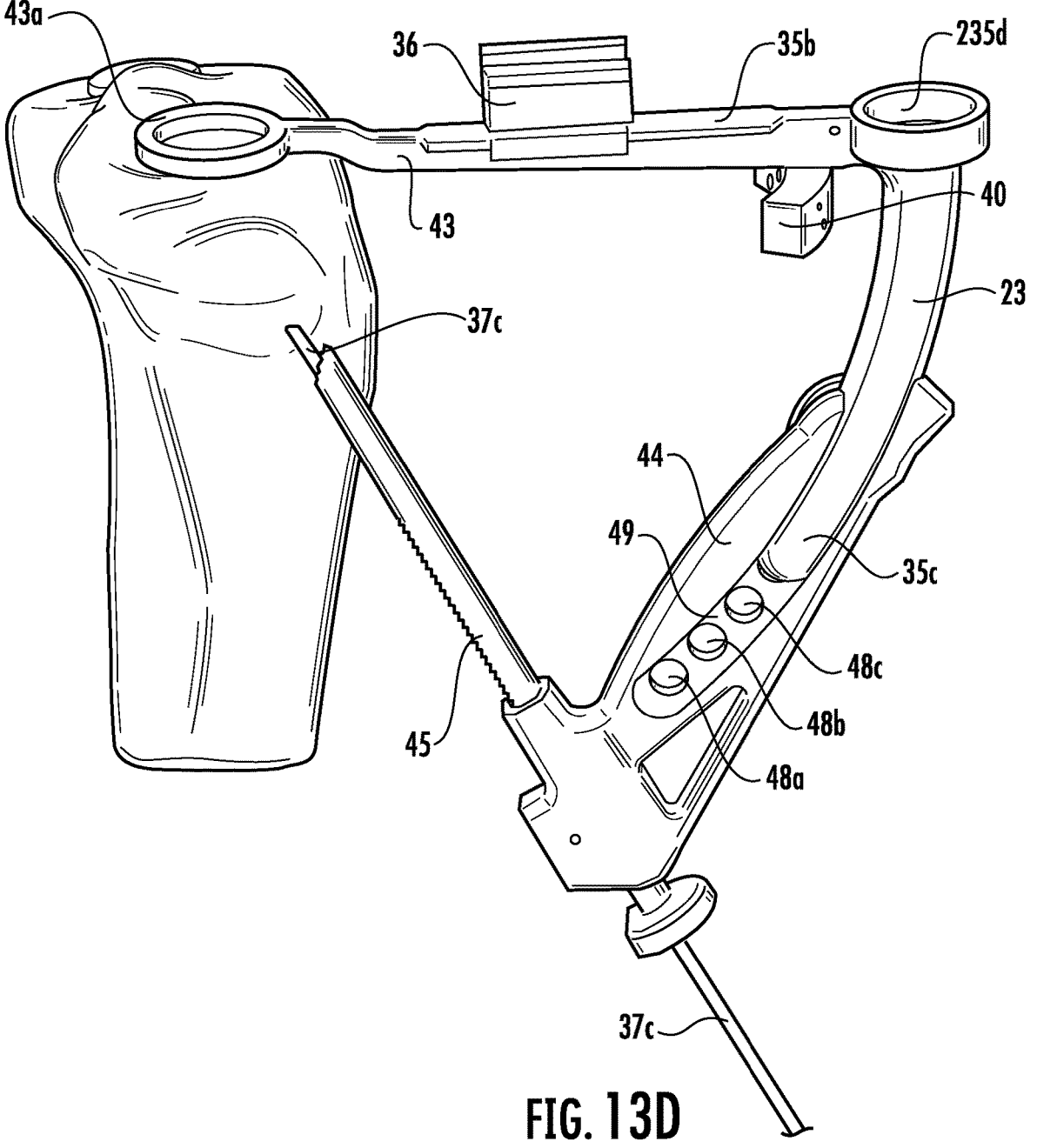
FIG. 13D is a side perspective view of the surgical tool assembly engaged with a patient's anatomy in a third state.
Figure 13E:
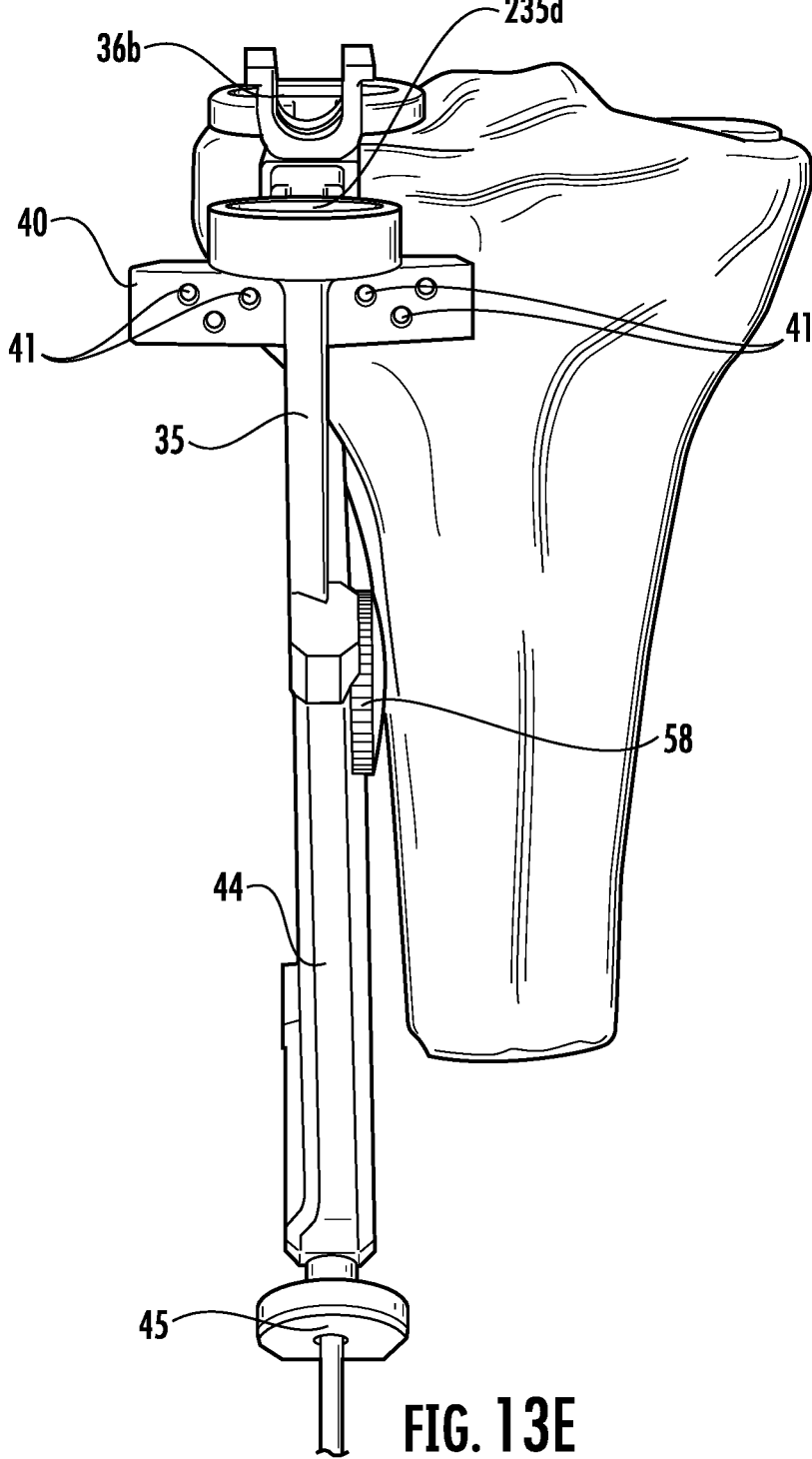
FIG. 13E is a rear view of the surgical tool assembly engaged with a patient's anatomy.
Figure 13F:
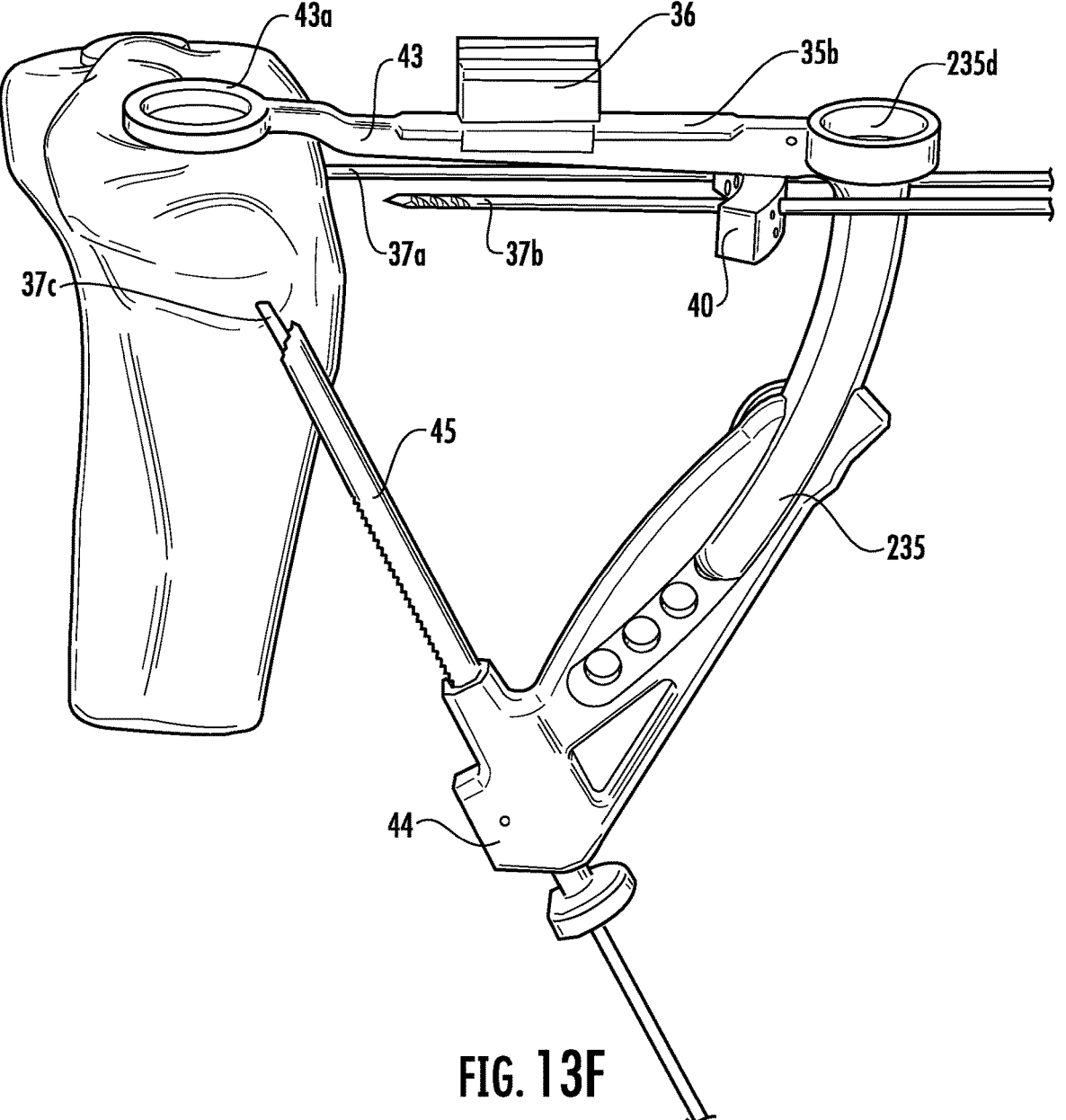
FIG. 13F is a side perspective view of the surgical tool assembly engaged with a patient's anatomy in a fourth state.
Figure 13G:
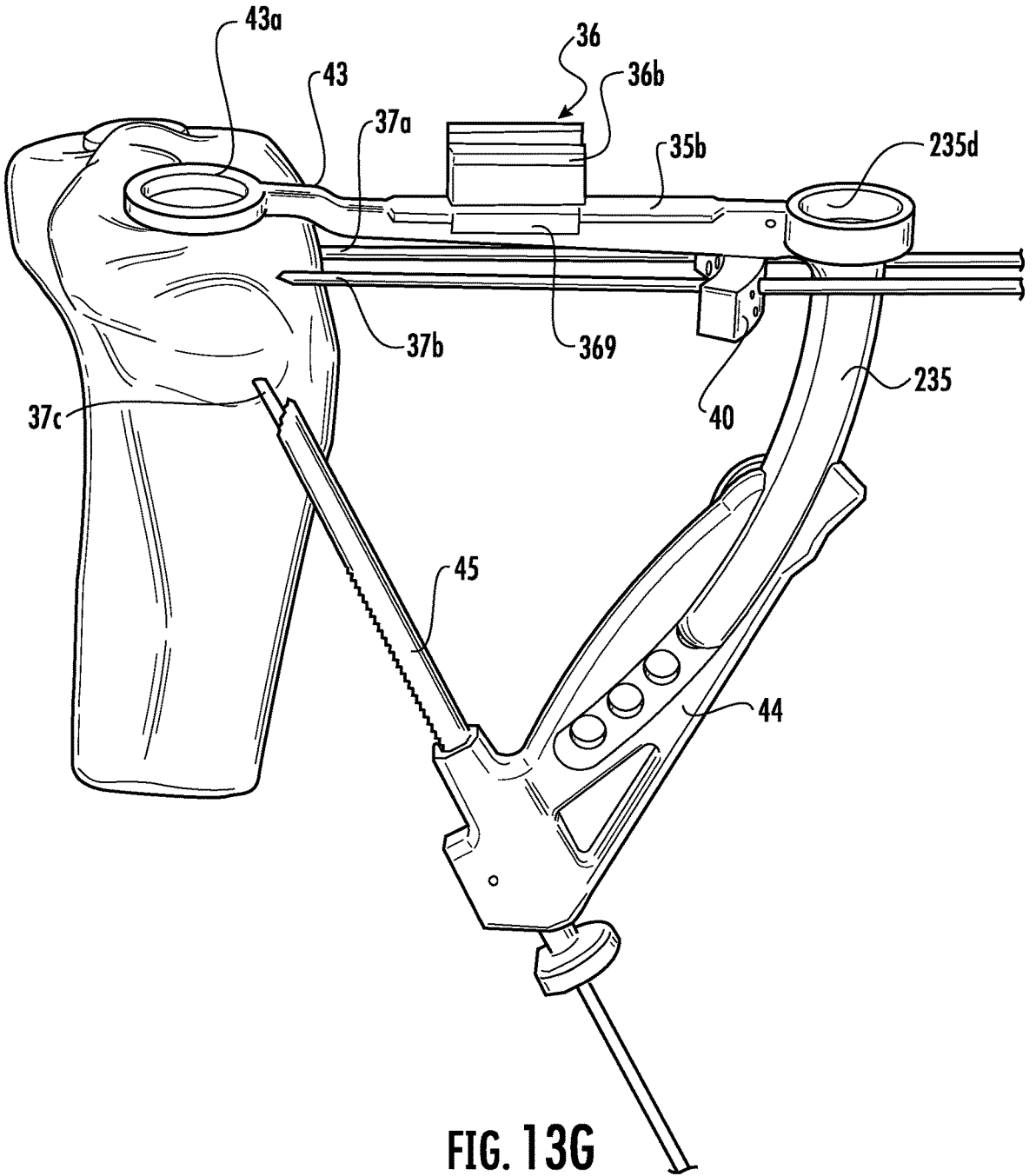
FIG. 13G is a side perspective view of the surgical tool assembly engaged with a patient's anatomy in a fifth state.
Figure 13H:
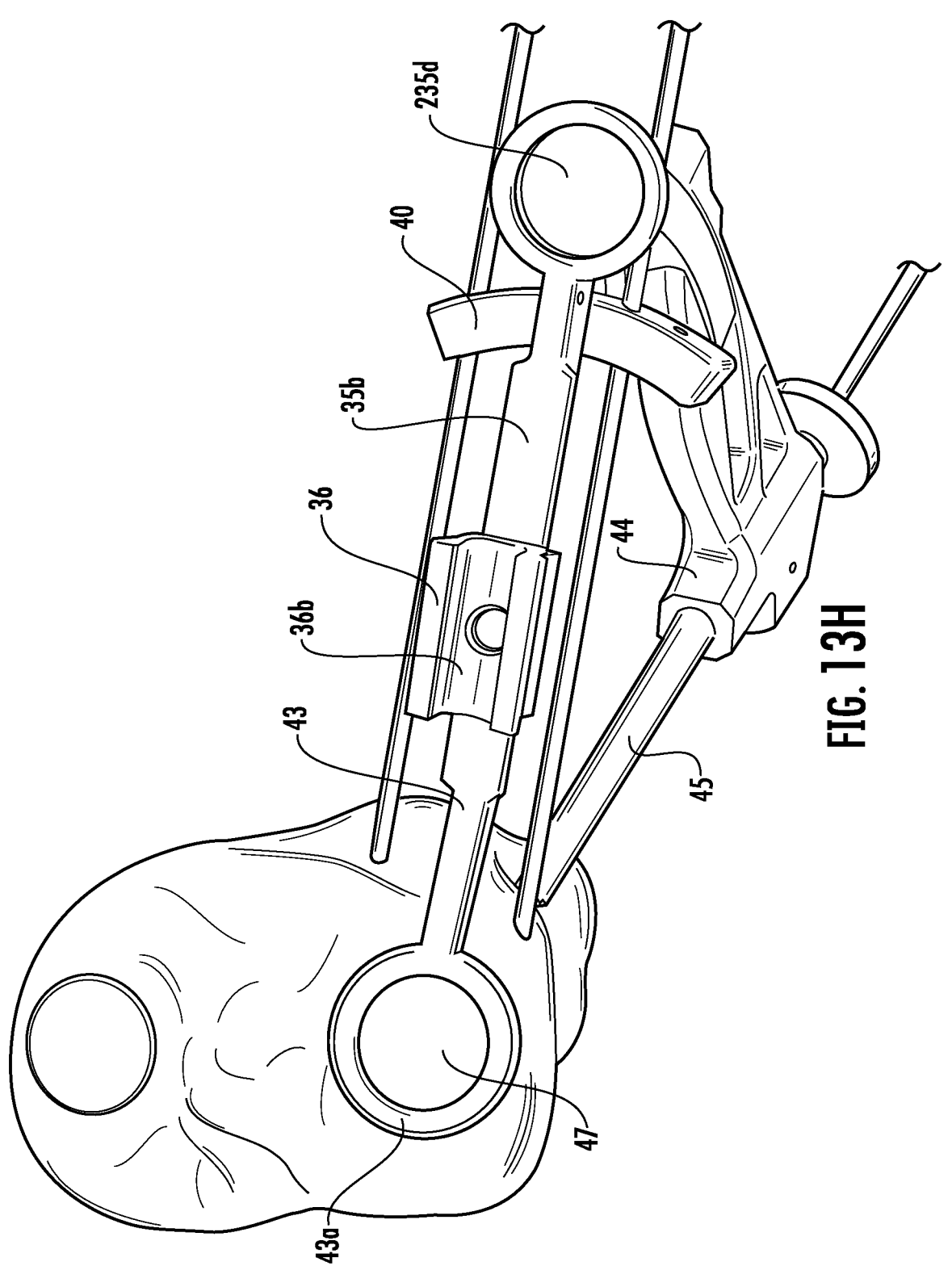
FIG. 13H is a top view of the surgical tool assembly engaged with a patient's anatomy.
Figure 13I:
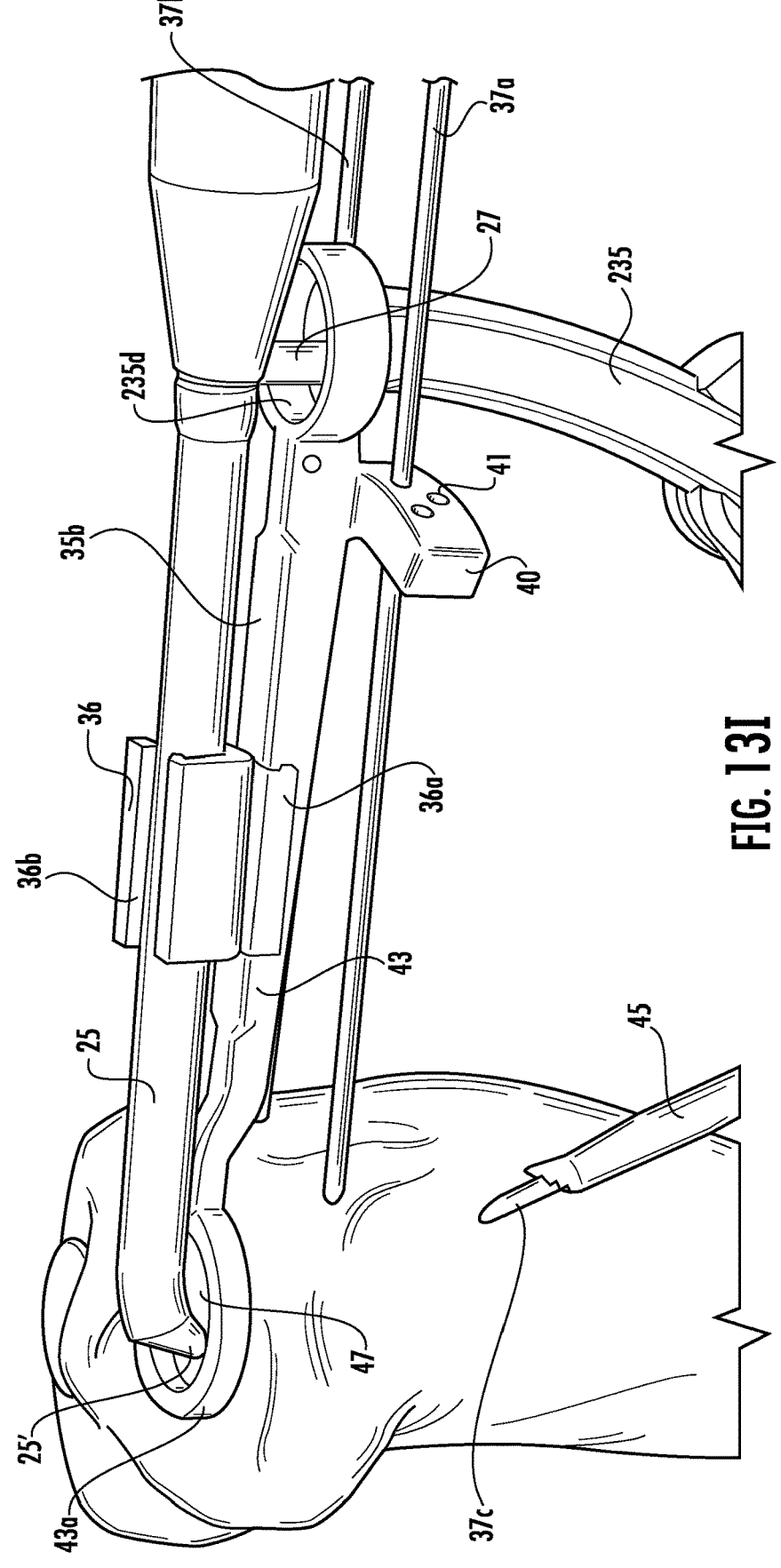
FIG. 13I is a magnified view of the surgical tool assembly engaged with a patient's anatomy.
Figure 13J:
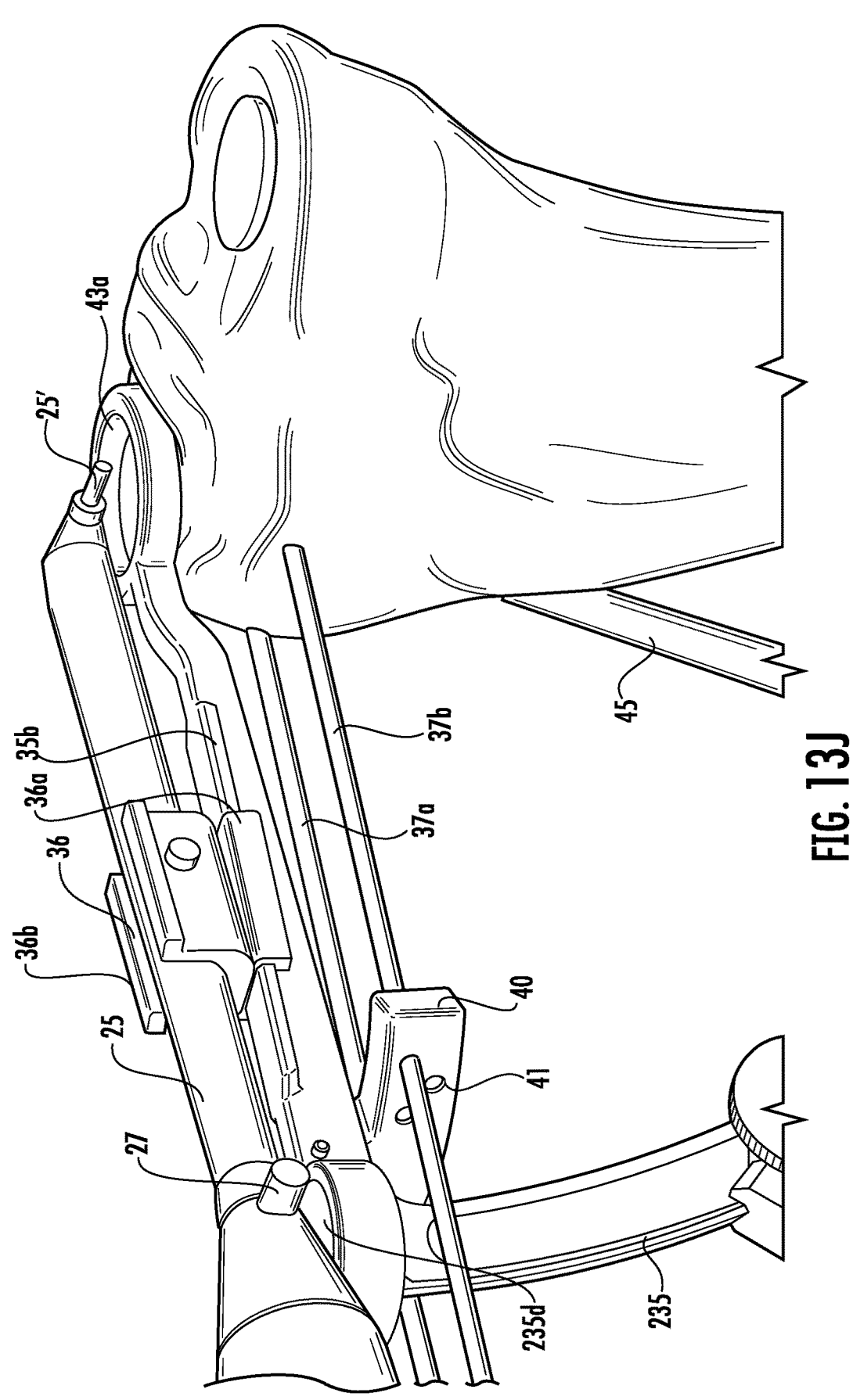
FIG. 13J is a rear perspective view of the surgical tool assembly engaged with a patient's anatomy.
Figure 13K:
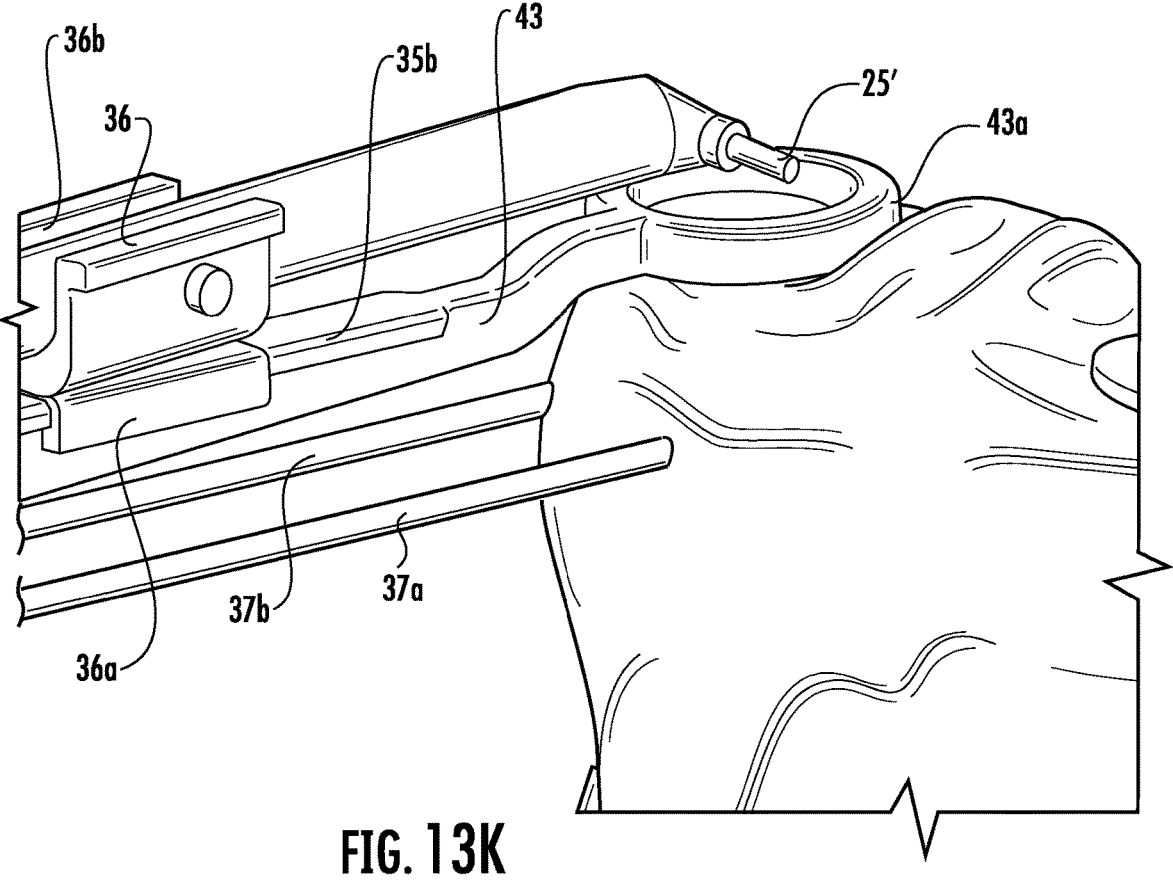
FIG. 13K is a magnified view of the surgical tool assembly engaged with a patient's anatomy.
Figure 13L:
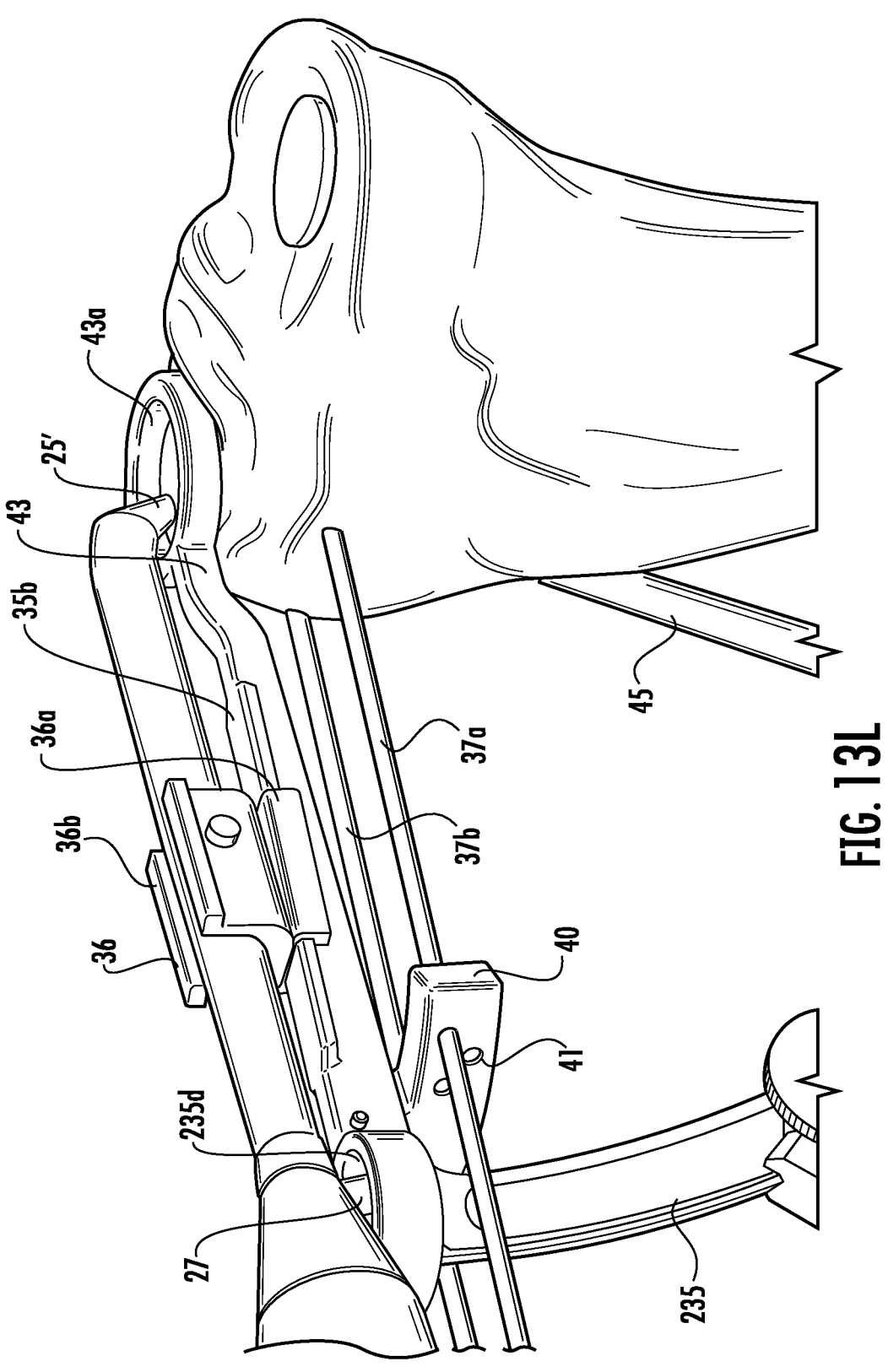
FIG. 13L is another rear perspective view of the surgical tool assembly engaged with a patient's anatomy.

FIGS. 13A-13L illustrate another aspect of the surgical tool assembly 234. As shown in FIGS. 13A-13L, the surgical tool assembly 234 includes a first guide tool portion 235 and a second guide tool portion 44. The first guide tool portion 235 is similar to the first guide tool portions 35, 135 unless specified herein. As shown in FIG. 13A, the surgical tool assembly 234 can include a plurality of first guide tool portions 235, 235', 235", as described in more detail herein.

The first guide tool portion 235 and the second guide tool portion 44 can be formed as separate structures in one embodiment. In another embodiment, the first guide tool portion 235 and the second guide tool portion 44 can be formed integrally with each other. The first guide tool portion 235 generally includes a support or instrument guide assembly 36 for the drill 25, and a first support guide 40. A plurality of K-wires 37a, 37b, 37c can be provided to stabilize the surgical tool assembly 234. The first support guide 40 can be provided on the first guide tool portion 235, and the first support guide 40 defines a plurality of openings 41 dimensioned to permit the K-wires 37a, 37b, 37c to extend therethrough. The K-wires, once installed in the openings 41, fix the first guide tool portion 235 in place and prevent movement of the surgical tool assembly 234.

The second guide tool portion 44 can be connected to the first guide tool portion 235 via an interface 48. The interface 48 can include a plurality of adjustment openings 48a, 48b, 48c, 48d that are configured to allow for relative adjustment between a connection of the first guide tool portion 235 to the second guide tool portion 44. For example, a terminal end 35c of the first guide tool portion 235 can include a prong or post configured to be received within the plurality of adjustment openings 48a, 48b, 48c, 48d. A track 49 can be defined on the second guide tool portion 44 that is dimensioned to receive a portion of the first guide tool portion 235, i.e. terminal end 35c. The track 49 can be formed as a slot or recess. A locking assembly 58, shown in FIG. 13E, can be provided to secure the first guide tool portion 235 with the second support guide 44. In one aspect, this configuration allows the first guide tool portion 235 to slide relative to the second support guide 44 thereby adjusting the angle of the cannula 45 while maintaining the end 43a of the guide arm 43 target centered on the recipient site. Basically, this configuration keeps the k-wire extending through cannula 45 aimed at the center of end 43a of the guide arm 43. The relative geometries of the target site (i.e. patient recipient site for implant 10) to target guide constraint (i.e. end 43a of the guide arm 43), drill constraint couple (i.e. opening 38a in cutting guide 38) to drill bit (i.e. end 25'), and distance of the rotating swivel guide (i.e. instrument guide assembly 36) from target and target constraint (i.e. end 43a of the guide arm 43) can be one-to-one in one aspect. In another aspect, one of ordinary skill in the art would understand that multiple varying geometries and relationships can be provided between these elements.

The second support guide 44 is secured with the first guide tool portion 235 and includes at least one opening configured to receive at least one K-wire, such as K-wire 37c. The second support guide 44 can be considered a stabilizing guide, in one aspect. The second support guide 44 can include a cannula 45 for the K-wire 37c that is generally oriented at an oblique angle relative to K-wires 37a, 37b supported by the first support guide 40 of the first guide tool portion 235.

In this arrangement, triangulation targeting of the desired joint surface implant recipient site is controlled. The K-wire 37c engages the cutting guide 38, which restricts and guides the right-angle drill 25 relative to the desired recipient site. Additional K-wires 37a, 37b can be used to stabilize the first guide tool portion 235 relative to the joint surface recipient site. In one aspect, an angle defined between the K-wire 37c and either one of the other two K-wires 37a, 37b is between 45 degree to 80 degrees. One skilled in the art would understand that this angle will vary due to multiple parameters and will be varied when this indirect guide system is used for other joint applications such as the shoulder humerus and glenoid joint surfaces.

The instrument guide assembly 36 limits or restricts sliding and rotation of the drill 25. The instrument guide assembly 36 can include a slider 36a slidably secured on the base portion 35a of the first guide tool portion 235. In one aspect, the base portion 35a of the first guide tool portion 235 defines a track 35b having a predetermined stoke or length for the slider 36a to slide along. The track 35b can be formed as a T-shaped track with a corresponding receptacle formed on the slider 36a to engage with the T-shaped track. A support interface 36b can be pivotably secured to the slider 36a and can include a channel or receptacle for attaching to the drill 25. The support interface 36b may be formed as U-shaped bracket or holder dimensioned to engage a portion of the drill 25. The support interface 36b can include fastening elements to secure the drill 25 in place. The support interface 36b can be elastically deformed by insertion of the drill 25 such that the support interface 36b grips the drill 25. This arrangement provides for sliding and rotational movement of the drill 25, and ensures that the stroke or movement of the drill 25 is restricted to a predetermined geometry or length of the track 35b.

The first guide tool portion 235 can include a guide arm 43 extending from a base portion 35a of the first guide tool portion 235. An end 43a of the guide arm 43 can define a first receptacle 47. The guide arm 43 can extend at an oblique angle relative to the opposite terminal end 35c. The first receptacle 47 is configured to limit the path or stroke of the cutting end 25' of the drill 25. In one aspect, the first receptacle 47 has a circular perimeter that generally mimics or matches the profile of the implant 10. In one aspect, the first receptacle 47 is slightly smaller than an outer perimeter of the implant 10. In one aspect, the track 35b has a length that is greater than a diameter of the first receptacle 47. This ensures that the slider 36a can move the necessary distance to accommodate the relative geometry of the first receptacle 47.

The end 43a of the guide arm 43 with the first receptacle 47 is configured to sit on the worn-out joint surface and is stabilized by its flat perimeter, which may be coated with a hydrogel or soft durometer polymer to protect the perimeter cartilage, and is leveled to the circumferential contiguous cartilage surface, through compression with the engaged K-wires and the guide tool or drill. The end 43a can be pressed downward onto the patient's anatomy to further stabilize the assembly relative to the patient, in addition to the engagement of the K-wires with the patient's anatomy.

Based on this configuration, movement of the drill 25 is generally limited by the first guide tool portion 235 by at least three features: the first receptacle 47, the second receptacle 235*d*, and the instrument guide assembly 36.

As shown in FIG. 13A, the plurality of first guide tool portions 235, 235', 235" can have first receptacles 47, 47', 47" and second receptacles 235*d*, 235*d'*, 235*d"* of varying sizes. This allows a surgeon to select an appropriately sized first guide tool portion based on the size of implant and recipient site in a patient.

Robot Targeting Device for Treating Cartilage Disorders

Surgical robots, which can include multiple tools having both software and hardware aspects and components, may enhance the precision of the surgical intervention in treatment of a disease process, such as osteoarthritis. The robotic surgical tool must be accurately guided for its use in surgery to deliver precise results for the benefit of the patient. One such embodiment of a robotic system 50 is illustrated schematically in FIG. 12A, and can be implemented with any one or more of the embodiments disclosed herein.

One example of a surgical robotic system includes the da Vinci Surgical System. This system provides surgeons with more precise control for a range of procedures. Using magnified 3D high-definition vision and controls that attach to a surgeon's wrists and hands, the da Vinci Surgical System is capable of making tiny, exact incisions that human hands might not otherwise be able to make. This offers enhanced control to surgeons and, since the surgery is less invasive than traditional surgery, a faster healing time for patients.

Another example of a surgical robot system includes the ROSA® Knee System, which is indicated as a stereotaxic instrumentation system for total knee arthroplasty (TKA). This system is configured to assist the surgeon in providing software-defined spatial boundaries for orientation and reference information to identifiable, anatomical structures for the accurate placement of knee implant components.

Another example of a surgical robot system includes the NAVIO™ Surgical System, which is a surgical planning, navigation and intraoperative visualization system combined with a handheld smart instrument for bone sculpting. The camera cart communicates the relative position of the handpiece, the femur, and the tibia (via rigid tracker arrays) to the computer cart. The patient's bone is prepared according to an intraoperative plan that combines soft-tissue balancing and collected anatomic information with controlled bone removal and predictable long-leg alignment Robotic surgical tools for total joint replacement all generally include a robotic guidance system that must be registered relative to the pre-operation diagnostic studies, including X-rays, CT scans and MRI scans. The registration is then completed at the beginning of the surgical procedure. Femoral and tibial arrays are placed or oriented at the femoral and tibial checkpoints, for navigation orientation of the robotic system. Patient landmarks are collected and the process also includes registering the landmarks relative to the arrays modeled or visualized by the robotic navigational system. Bone registration and verification are performed on both the femoral and tibial surfaces. Boney osteophytes are removed to the extent that the surgeon can passively correct the coronal deformity.

The magnitude of the valgus stress during these processes must be such that it opens up the collapsed medial compartment and tensions the medial collateral ligament (MCL) to achieve the desired degree of correction and joint stability. This is all critical when addressing joint surface damage, which has progressed to the point that boney deformities become evident, with resultant bone and joint malalignment occurring.

One aspect of this disclosure provides a surgical treatment option earlier in the disease process of osteoarthritis or post traumatic osteoarthritis, before boney deformity and associated malalignments become an issue. The positioning of navigational arrays are necessarily invasive and thereby increase potential morbidity for the patient, especially in arthroscopic surgical procedures. When performing an open joint surgery, through an arthrotomy such as a joint replacement, this additional morbidity is minimal. When performing an arthroscopic interventional surgery, the additional morbidity of the robotic navigational array could potentially be greater than the arthroscopic intervention.

The guide tool assemblies and triangulation configurations disclosed herein may be used in conjunction with any robotic surgical tool in order to aid with the arrays, or any other aspects of robotic surgical tools. In other words, the guide tool and assembly disclosed herein can be implemented with a robotic surgical tool such that the robotic surgical tool can effectively and efficiently index based off of the targeting device (i.e., the cutting guide, such as elements 36, 43, 47, etc.). Additionally, any robotic surgical tool can be implemented to work in conjunction with the embodiments disclosed herein, such that a robotic surgical tool controls the cutting tool or drill.

Just as each of the robotic systems described herein index the robotic navigation based upon the anatomic indexing utilizing the arrays placed in the patient during surgery referencing the anatomy defined from pre-operation x-rays and scans, the disclosure and embodiments described herein are configured to base the robotic guidance upon the targeting guide, as placed or arranged by the surgeon and then coupled, stabilized, and secured to the triangulation guide and robot control system. In other words, the devices disclosed herein can be used in conjunction with robotic systems. The targeting guide can be configured to identify the starting point and orientation for the robotic system, which is necessary for the robotic system in the preparation of the recipient site for the implant intended to replace the damaged cartilage. The targeting guide is configured to be aligned and placed in the joint relative to the cartilage surrounding the damaged cartilage being replaced. The guide is integral to and secured with the triangulation guide, so that the robot will prepare a recipient site based upon the alignment of the targeting guide. In one aspect, this would be done in lieu of indexing the entire joint and bone anatomy and would rather be based upon the targeting device directly rigidly coupled to the robotic system, through the angled drill bit. The surgeon would thereby align the target guide, i.e. elements 43*a* and 47, centered over the cartilage defect, and secure it in place with the triangulation guide, with the additional stabilizing K-wires. In one aspect, the robotic system is programmed to prepare a hole in the bone with a specific size, outer geometry and depth, for fixation of a device in the hole. The specific alignment of the robotic system is determined by the targeting guide orientation and alignment, which the surgeon placed in the joint in preparation for the robotic system to make the specific hole aligned and oriented in a fixed way to the specific matched targeting guide.

Figure 14A:
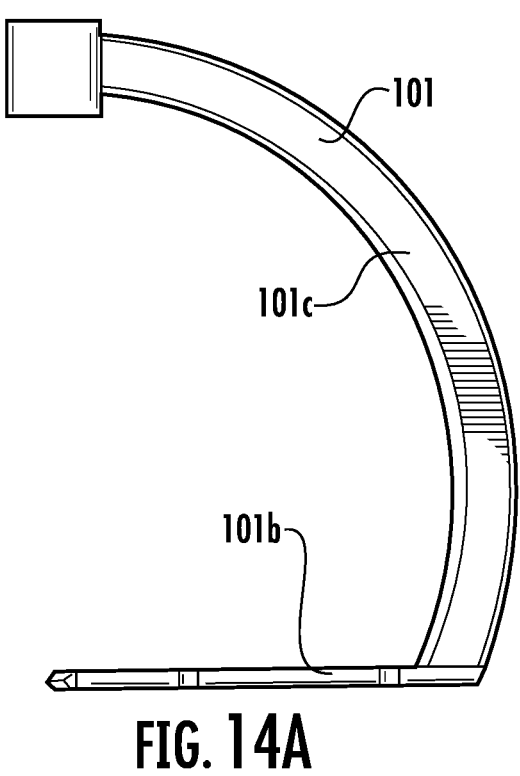
FIG. 14A is a side view of an impactor handle tool.
Figure 14B:
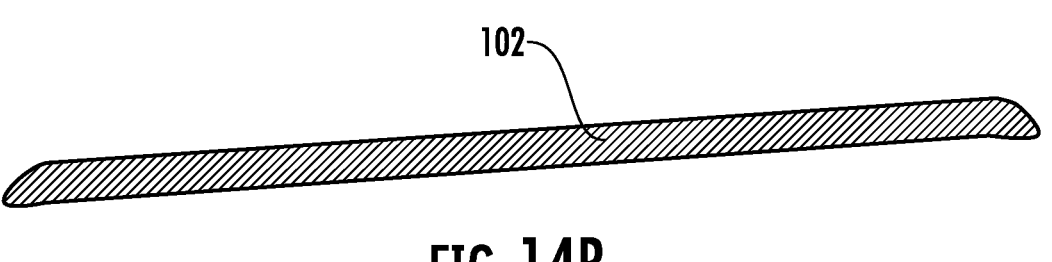
FIG. 14B is a side view of a skid.
Figure 14C:
FIGS. 14C and 14D are side views of an inserter.
Figure 14D:
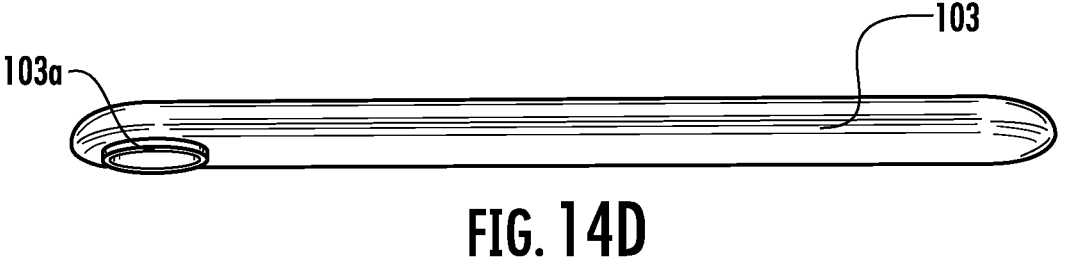
Figure 14E:
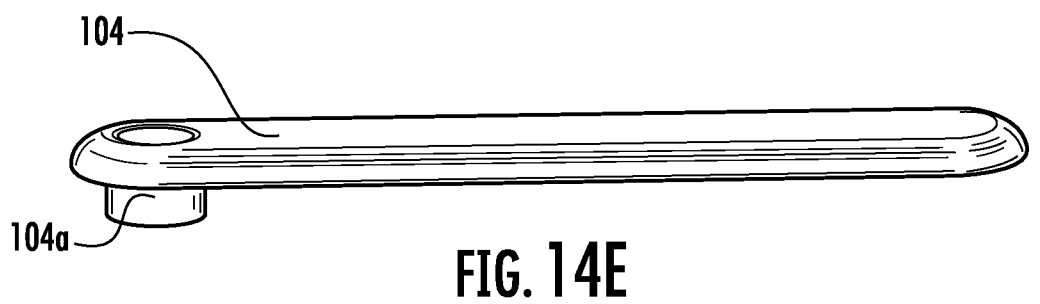
FIGS. 14E and 14F are side views of an impactor.
Figure 14F:
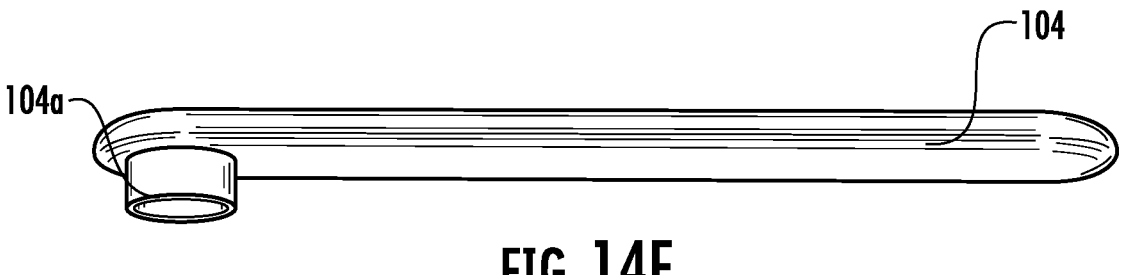
Figure 14G:
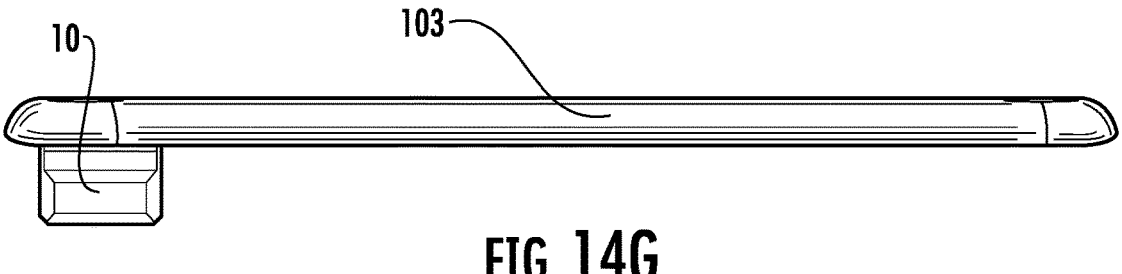
FIG. 14G is a side view of the inserter with the implant.
Figure 14H:
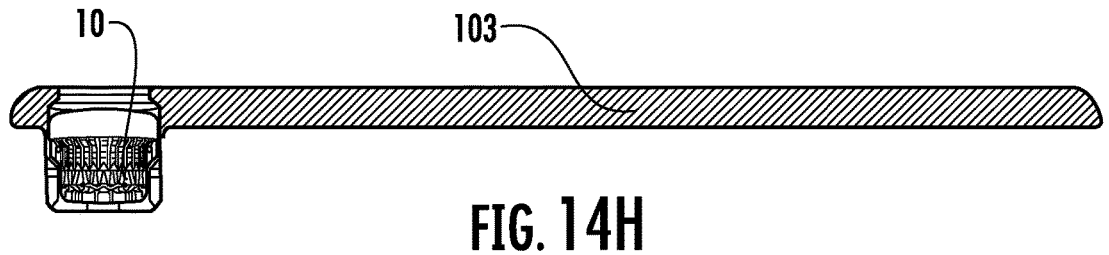
FIG. 14H is a cross-sectional view of the inserter with the implant.
Figure 14I:
FIG. 14I is side view of an impactor with the implant.
Figures 14J, 14K, 14L:
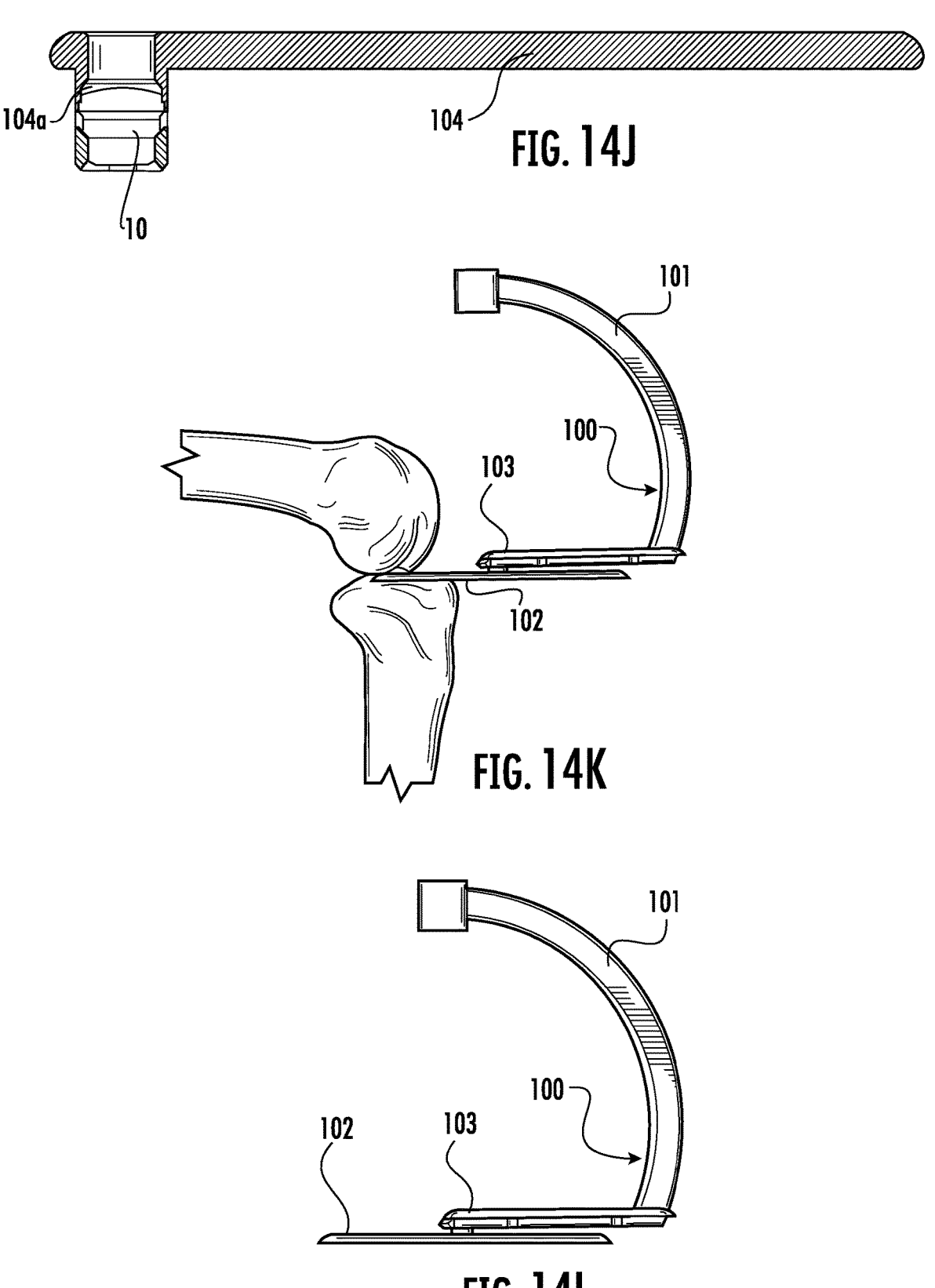
FIG. 14J is a cross-sectional view of an impactor with the implant
FIG. 14K is a side view of an inserter assembly engaging a patient's anatomy.
FIG. 14L is a side view of the inserter assembly.
Figure 14M:
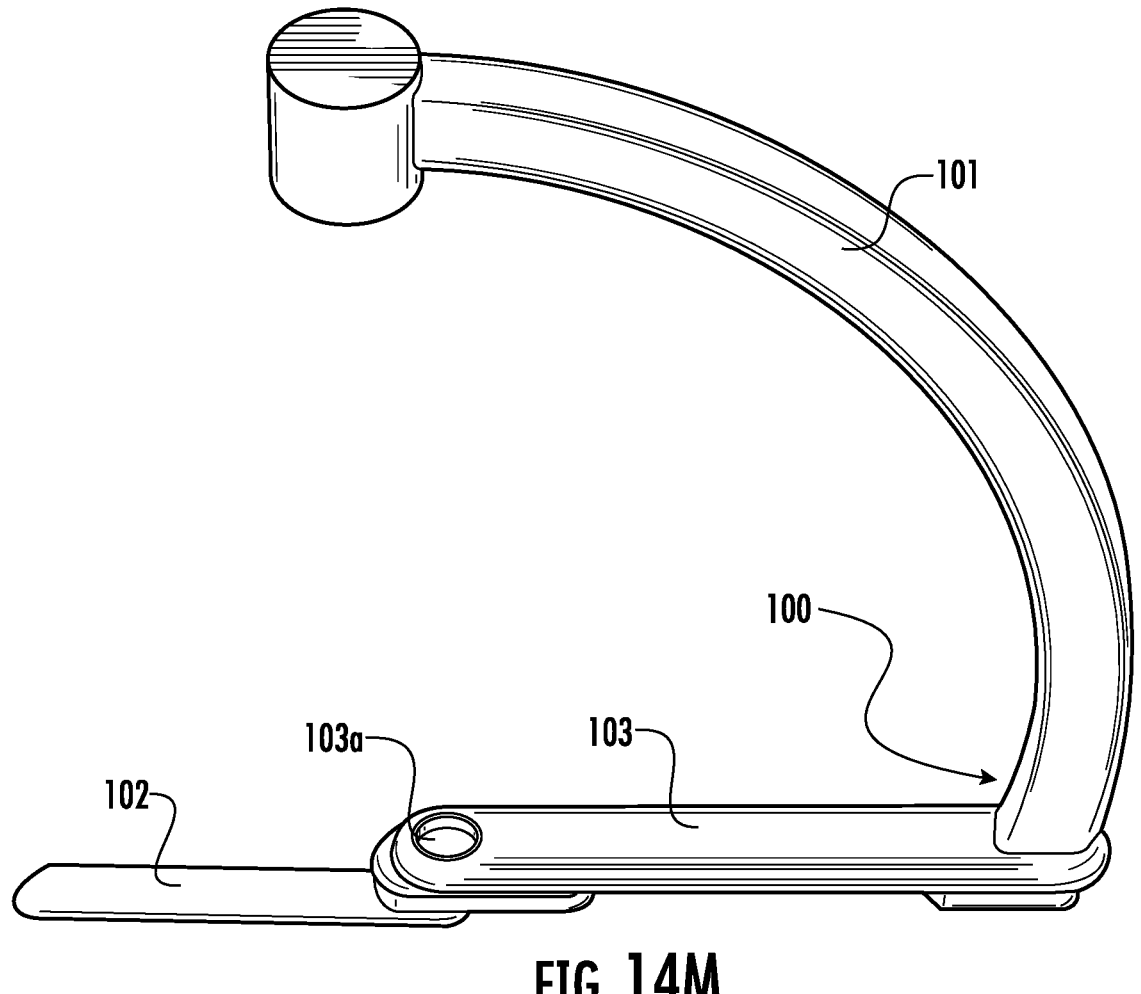
FIG. 14M is a perspective view of the insert assembly.
Figure 14N:
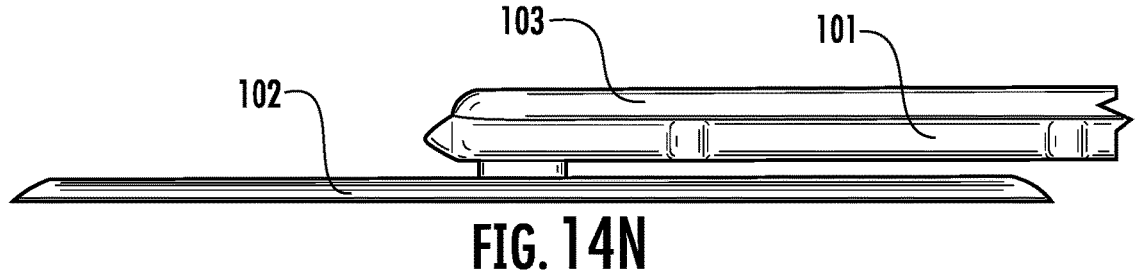
FIG. 14N is a side view of the impactor handle tool, skid, and inserter in a first state.
Figure 14O:
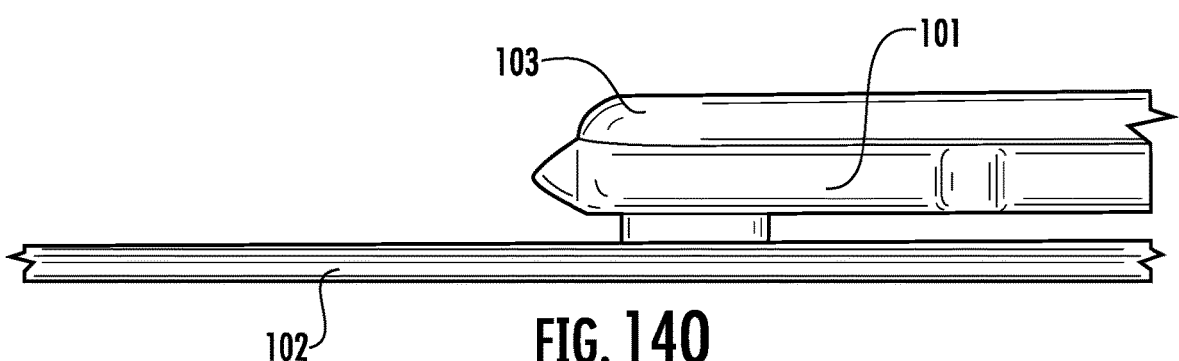
FIG. 14O is another side view of the impactor handle tool, skid, and inserter in a second state.
Figure 14P:
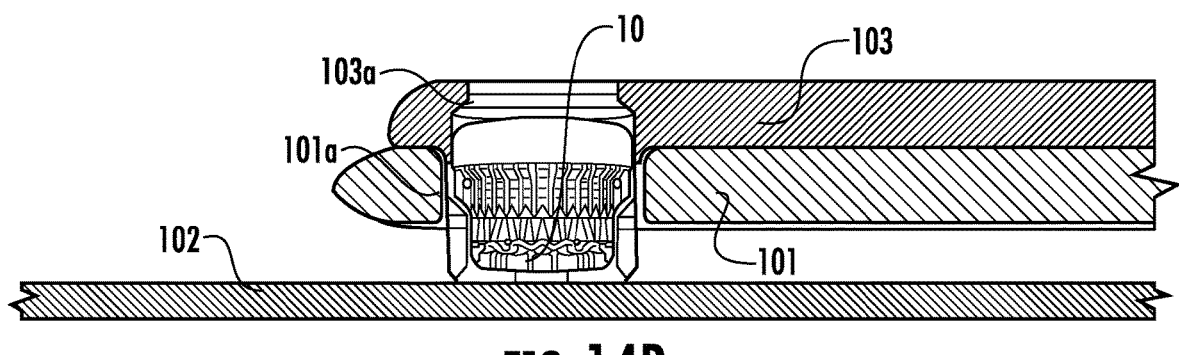
FIG. 14P is a cross-sectional view of the impactor handle tool, skid, and inserter.
Figure 14R:
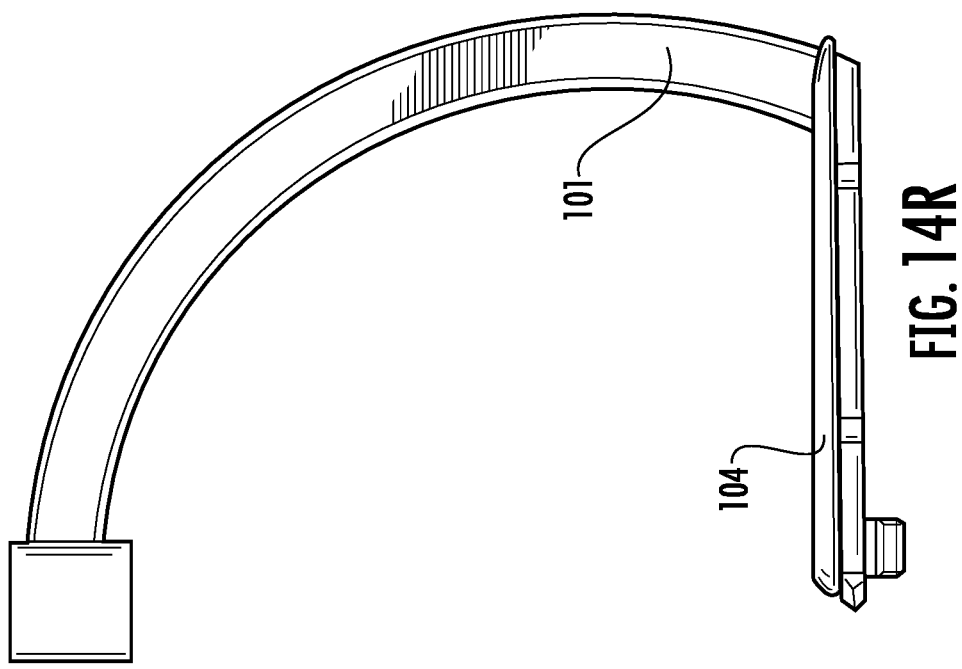
FIG. 14R is a side view of the impactor handle tool and impactor in a second state.
Figure 14Q:
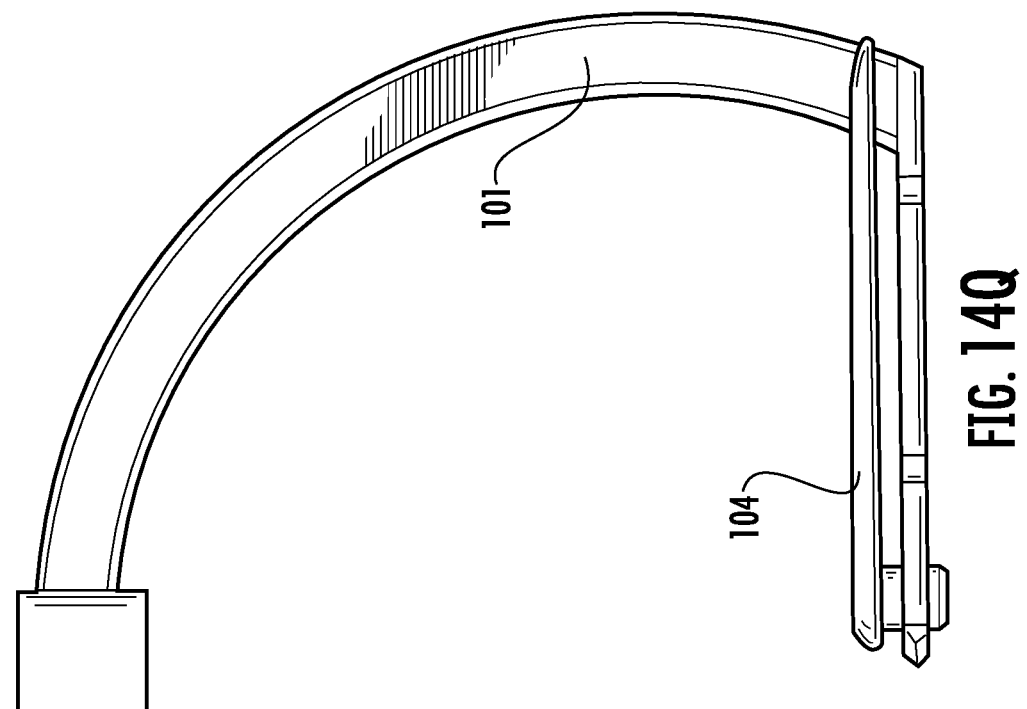
FIG. 14Q is a side view of the impactor handle tool and impactor in a first state.
Figures 14S, 14T:
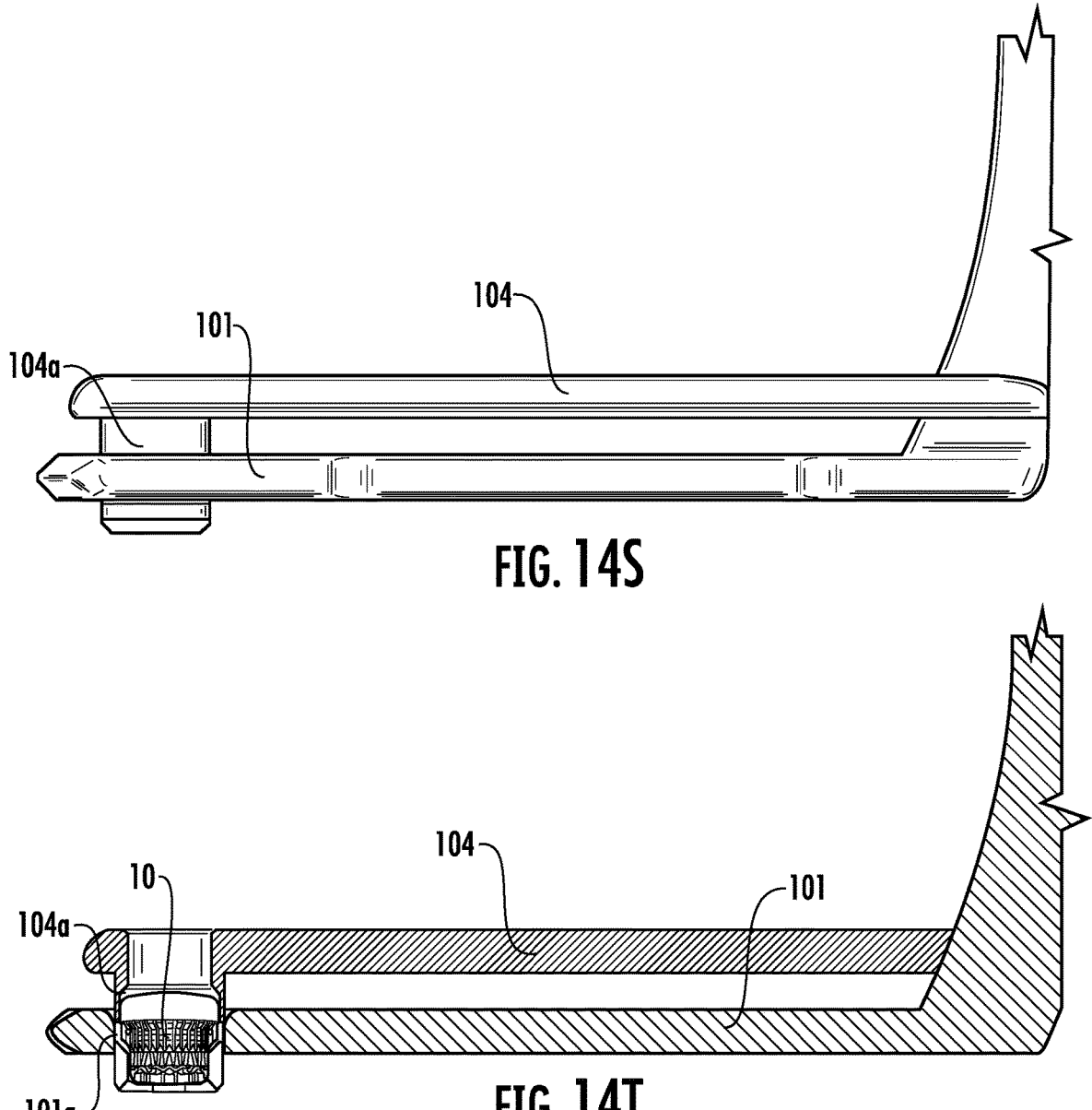
FIG. 14S is a side view of a portion of the impactor handle tool and impactor in a third state.
FIG. 14T is a side cross-sectional view of a portion of the impactor handle tool and impactor in the third state.
Figure 14U:
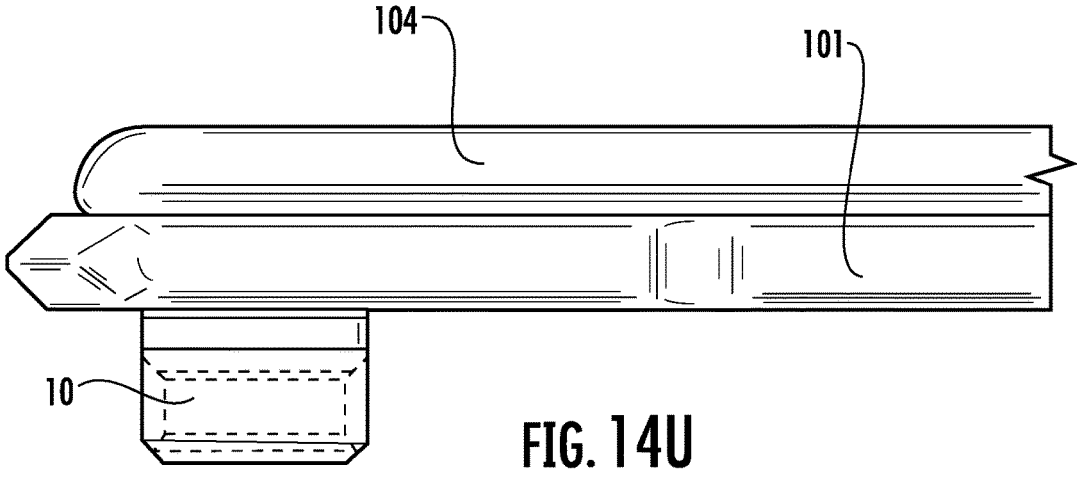
FIG. 14U is a side view of the impactor handle tool and impactor in a fourth state.
Figure 14V:
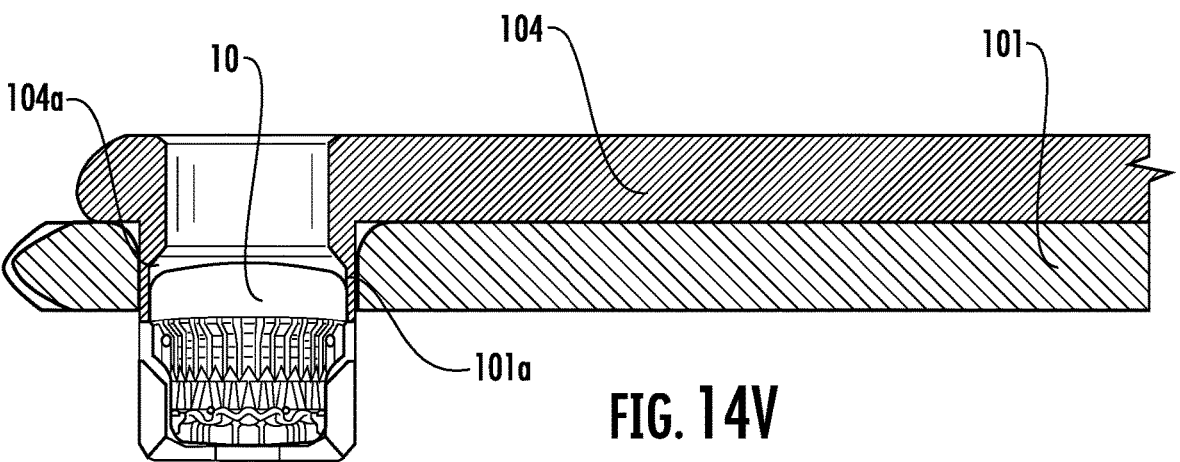
FIG. 14V is a cross-sectional view of the impactor handle tool and impactor in the fourth state.
Figure 14W:
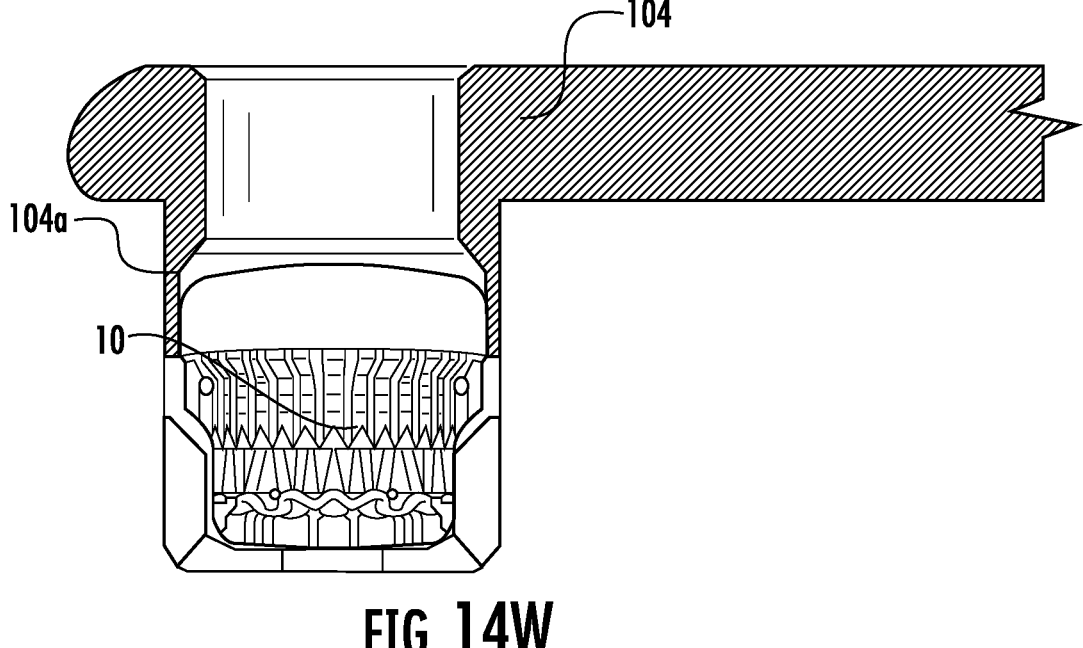
FIG. 14W is a magnified cross-sectional view of the impactor engaging the implant.

FIGS. 14A-14W illustrate various components, tools, arrangements, etc., for installing an implant when indirect access to the recipient site is provided.

FIG. 14A illustrates an impactor handle tool 101. The impactor handle tool 101 can include at least two arms, including a first straight arm 101*b* defining an opening 101*a*, and a second curved arm 101*c* defining a handle for user or surgeon. The opening 101*a* can be dimensioned to support the implant 10 and allow the implant 10 to pass through the opening 101a. FIG. 14B illustrates a skid 102 that generally has a flat profile. FIGS. 14C and 14D illustrate an inserter 103. The inserter 103 includes an opening or interface 103a configured to hold or retain the implant 10.

FIGS. 14E and 14F illustrate an impactor 104. A plunger 104a on the impactor 104 is configured to engage with the implant 10. Specifically, the plunger 104a can have a contact surface configured to engage with the implant 10. The plunger 104a can include a rim dimensioned to engage with a solid rim or body of the implant 10, as shown in FIG. 14W. This engagement prevents any damage to the bearing element of the implant 10. The impactor 104 provides adequate length to facilitate the compression of the implant 10 down into a recipient hole. FIGS. 14G and 14H illustrate the inserter 103 holding the implant 10, and FIGS. 14I and 14J illustrate the impactor 104 engaging the implant 10.

FIG. 14K illustrates an inserter assembly 100 (including any one or more of the components shown individually from FIGS. 14A-14J) aligned with a patient's anatomy for insertion. As shown, the impactor handle tool 101 is assembled with the skid 102 and the inserter 103. In one aspect, the implant 10 is delivered into the knee along the skid 102 to prevent damage to other joint cartilage surfaces.

FIG. 14L is a side view of the inserter assembly 100, and FIG. 14M is a perspective view of the inserter assembly 100. FIGS. 14N-14P illustrate further aspects of the skid 102, the impactor handle tool 101, and the inserter 103. The opening 101a in the impactor handle tool 101 is dimensioned to allow the plunger 104a formed on the impactor 104 to pass through. These figures illustrate how the implant 10 is delivered to the prepared recipient site along the skid 102. The tool system is used to initially position the implant 10 into the recipient site hole and begin to compress the anchor body of the implant 10 into the recipient hole.

FIGS. 14Q-14W illustrate the impactor 104 being used in conjunction with the impactor handle tool 101 in order to drive the implant 10 downward and into a recipient site.

These drawings illustrate how the implant 10 is pressed through the impactor handle tool 101 and is impacted and compressed into the recipient hole. This can be accomplished by screws connecting the impactor 104 down onto the impactor handle tool 101, thus pushing the implant 10 down into the recipient hole. Alternatively, this could be accomplished with a vice grip compressing the implant 10 through the impactor handle tool 101 into the recipient hole.

In one embodiment, the desired recipient site with exposed grade IV joint bearing surface damage can be identified and prepared with identification of the center of the damage. The appropriate planar orientation of the bearing surface of the implant is identified and locked in with the planar aspect of the stabilizing guide which aligns with the perimeter of the cartilage surface defect contiguous cartilage bearing surface. This configuration of a guide assembly with triangulating targeting of the desired bone implant recipient site for an angled drill allows for localization control, restricting the machining of the bone to the desired shape outlined by the targeting guide or platform (such as the cutting guide). The stabilizing guide (specifically the guide tool), with two horizontal guide K-wires and central targeting K-wire for the targeting platform localization, provides stabilization and fixation for right angle drill. The targeting platform which sits on the worn-out joint surface and is aligned and stabilized by its flat perimeter, which may be coated in a hydrogel or soft durometer polymer to protect the perimeter cartilage. This is aligned and leveled to the circumferential contiguous cartilage surface, through compression with the engaged K-wires and triangulated guide tool.

In another aspect, the damaged recipient site can be prepared with a round planar cutting tool in the center of the damage. An angled drill rotating platform (i.e. a cutting guide) can be used for localization control, restricting the machining of the bone to the desired shape outlined by a telescoping planar tool coupled to the guide tool. The stabilizing guide, with central targeting K-wire and two stabilizing K-wires for the targeting platform (such as the cutting guide) aligns and stabilizes right angle planar tool. The cutting guide (i.e. end 43a of the guide arm 43) sits on the worn-out joint surface and is stabilized by a flat perimeter, coated in a hydrogel or soft durometer polymer to protect the perimeter cartilage. The platform or cutting guide is leveled to the circumferential contiguous cartilage surface, through compression with the three engaged K-wires and triangulated guide tool.

In another aspect, a telescoping guide tool is provided to adjust the cutting tool to a desired depth, which is controlled by the excursion of the telescoping assembly. This is all stabilized by the cutting guide which sits on the worn-out joint surface and can be stabilized by the flat perimeter, coated in a hydrogel or soft durometer polymer to protect the perimeter cartilage, leveled to the circumferential contiguous cartilage surface, through compression with the three engaged K-wires and the triangulated profile of the guide tool. In one aspect, the cutting guide may have two axes of rotational freedom to permit the cutting guide or platform to rotate until flush with joint surface being repaired, thereby defining the optimal alignment of the implant bearing surface, which is determined by the recipient site location and alignment.

In one embodiment, the desired recipient site with exposed grade IV joint bearing surface damage can be prepared with a round burr in the center of the damage. A guide tool with a cutting guide and a drill restricts the machining of the bone to the desired shape outlined by the cutting guide. The guide tool, with two horizontal guide K-wires and central targeting K-wire for the cutting guide, is centered over the worn-out cartilage joint surface to be repaired. This arrangement, and more particularly the cutting guide, can serve as a landmark for a robotic system coupled to the guide tool and potentially reinforced with a direct optical orientation system for a robotic actuator to precisely machine the recipient site in the bone under the worn-out joint cartilage surface.

In one aspect, the cutting tool (for example, a right-angle drill) is robotically controlled and guided by the cutting guide. The cutting guide sits on the worn-out joint surface and is stabilized by the flat perimeter, which sits upon the rim of contiguous intact joint cartilage surface on the perimeter of the recipient site. The cutting guide rim, which sits upon the contiguous intact joint cartilage surface, is coated in a hydrogel or soft durometer polymer to protect the perimeter cartilage. The cutting guide rim is leveled and aligned to the circumferential contiguous cartilage surface, through compression with the three engaged K-wires and guide tool.

In one aspect, a method of preparing an implant site and a system for preparing an implant site are provided. The methods and systems include a guide tool and a cutting tool. In one aspect, the cutting tool is a right-angle drill. The guide tool can have a triangular profile when view from the side. In one aspect, a cutting guide (also referred to as a platform) is dimensioned to be partially arranged within a recipient site, and the cutting guide is coupled with the cutting tool. The cutting tool can be coupled to the guide tool such that a geometric cutting profile of a cutting end of the cutting tool is restricted via the guide tool.

In one aspect, at least three K-wires are provided for stabilizing the guide tool and/or securing the cutting guide in place. At least two of the K-wires extend approximately parallel to each other, and a third K-wire extends at an angle relative to the two other K-wires.

In one aspect, the cutting guide limits a cutting profile of the cutting tool to a circular profile.

In another aspect, a robotic system is configured to at least control the cutting tool.

An alignment guide assembly can be provided on the guide tool that defines a plurality of openings dimensioned to allow K-wires to extend therethrough.

An instrument guide assembly can be provided that includes a bracket slidably secured on a base portion of the guide tool, the base portion of the guide tool defining a track having a predetermined stoke or length for the bracket to slide along, and an interface pivotably secured to the bracket and including a channel or receptacle configured to couple with the cutting tool.

The cutting guide can include a flat perimeter configured to sit on a worn-out joint surface and stabilized via a flat perimeter edge. In one aspect, the flat perimeter of the cutting guide is coated with a hydrogel or soft durometer polymer. In one aspect, a coupler can be configured to attach a cutting end of the cutting tool to a guide arm of the guide tool.

In one aspect, the present disclosure provides arrangements that facilitate arthroscopic joint resurfacing of bone-on-bone synovial joint pathologies using a hydrogel, before progressive bone erosion manifests to cause joint deformities indicating more drastic treatment is necessary.

In one aspect, a targeting device for preparing a bone recipient site for a medical device is provided. The targeting device is precisely located, positioned, aligned and dimensioned to enable identification, localization, precise machining of the recipient bone cavity for delivery and fixation of the medical implant anchor into the bone recipient site to replace damaged cartilage.

In another aspect, a targeting device for robotic surgical systems is provided that simplifies and streamlines the registration process for the navigational component of the robot interfacing with the patient's anatomy. The targeting device for the robotic system may be integral and calibrated to the robotic surgical system. With the targeting device disclosed herein, the surgeon can orient the targeting device relative to the joint surface damage which needs to be repaired. When treating focal joint cartilage defects, early in the disease process, it is critical for success that the joint disease being treated has not progressed to the point that boney malalignment has occurred, such as a *varus* bowleg or valgus knock knee deformity. When treating joint cartilage lesions early in the disease process, before bone deformities, the surgeon can orient the targeting device to the joint surface being replaced, keying off the surrounding joint cartilage as a critical reference. Generally, the goal of cartilage replacement devices, for which the instrumentation herein has been designed, is to replace the damaged joint surface. The success of the joint surface replacement device is dependent upon the anatomic and physiologic placement of the device's joint bearing surface such that it is coplanar with the surrounding intact contiguous cartilage surface.

The robotic targeting device, system, process, and methods disclosed herein are useful with the surgical robots that use haptic technologies, as well as other alignment guides, whether handheld or platform based. The targeting configuration can be calibrated and integral to an existing robotic surgical system, which would obviate the need for the navigational arrays and associated morbidities. This would lead to more successful outcomes for patients, surgeons, hospitals, surgery centers, etc.

One skilled in the art understands that any one or more of aspects from any set of Figures can be implemented with any one or more of the configurations illustrated by the other Figures. For example, any of the aspects of the alignment guide tool 26 and the drill 25 from FIGS. 9A-9R may be used in any one or more of the embodiments disclosed by FIGS. 10A-10J; FIGS. 11A-11E; FIGS. 12A-12F; FIGS. 13A-13L; and/or FIGS. 14A-14W, and vice versa.

A process for using the instruments is also disclosed herein. In one aspect, the process begins with confirming the size, location, and alignment of the patient recipient site. This process can include determining the size of the cartilage surface defect with an appropriate target guide centered over an osteoarthritic Grade III-IV lesion of tibial plateau articular surface. For example, this could include selecting the correct sized first guide tool portions 235, 235', 235". The process can then include assembling and aligning the second guide tool portion 44 with the appropriately sized first guide tool portions 235, 235', 235", and centering the assembly over eroded cartilage exposed bone. The process can include adjusting an angle of the first and second guide tool portions until the ends of the first and second guide tool portions are in the appropriate positions relative to the joint cartilage surface to optimize restored joint surface congruity. The process can include adjusting the tool assembly to maximize circumferential contact of the end 43a of the first guide tool portion with the recipient site cartilage to optimize surface congruity of intact host joint cartilage and the implant surfaces.

The process can also include confirming that the end 43a of the tool covers the cartilage eroded exposed bone. The process can include adjusting the alignment relative to the tibial plateau parallel to a tangential plane of cartilage defect. The process can include confirming the size, location and alignment via circumferential rim contact of the end 43a through direct arthroscopic visualization. To secure the tool assembly in place, the process can include engaging the cannula 45 with the patient. The cannula 45 can include a ratcheted trochar guide that is configured to stabilize the assembly while also maintaining the positioning of the end 43a on the recipient site. The cannula 45 can engage directly against the patient's anatomy, such as the patient's bone. Next, the process can include further stabilizing the assembly via engagement of a K-wire 37c through the cannula 45 to the patient. This ensures that the assembly remains stationary during the procedure.

The process can also include confirming that the end 43a is centered over the cartilage defect and further stabilizing the tool assembly by additional K-wires 37a, 37b. The process can include confirming that the end 43a is seated on an intact cartilage rim of the surface cartilage defect, which is identified as the intended recipient site. An additional two K-wires 37a, 37b can be inserted through the first support guide 40 to secure the assembly. This helps ensure that the end 43a is securely fixed over the cartilage defect to be resurfaced. Additional imaging techniques, such as radiologic imaging, can be used to confirm the location of the K-wires, if necessary.

Next, the process can include positioning an instrument 25, such as a drill or debris evacuator, near the end 43a on an opposite side of the arthroscope. The process can include engaging the instrument with the instrument guide assembly 36 and then arranging the terminal end 25' (i.e. cutting end, drill, burr) into the receptacle 47 defined by the end 43*a*.

Once the end of the instrument is centered over the intra-articular target, the user can rotate the instrument while engaged within the instrument guide assembly 36 such that the terminal end of the instrument can begin cutting or otherwise engaging with the target recipient site. This process and assembly are designed for precise constraint with a hand-controlled instrument or actuator to control engagement of the terminal end of the instrument relative to the patient's anatomy. The assembly disclosed herein has a triangulation aspect such that the assembly is stabilized with the patient via multiple points of contact and stabilization, and ensures that the end 43*a* of the assembly engaging the patient remains stationary, while also limiting the movement of the instrument.

A method of engaging an instrument with an implant recipient using a surgical tool assembly is also disclosed. The method includes providing a first guide tool portion comprising an instrument guide assembly and a guide arm defining a first receptacle, and a second guide tool portion configured to receive a K-wire. The first and second guide tool portions can be adjustable relative to each other. The method includes aligning the first receptacle with the implant recipient site. This can include directly engaging the end of the guide arm with the implant recipient site. The method includes stabilizing the surgical tool assembly via insertion of at least one K-wire through at least one of the first guide tool portion or the second guide tool portion. In one aspect, multiple K-wires can be inserted through respective regions of the first guide tool portion and the second guide tool portion. Once in position relative to a patient, the first guide tool portion and the second guide tool portion have a triangular profile when viewed from the side. Additionally, the guide arm extends tangentially relative to the implant recipient site. The method includes attaching an instrument to the instrument guide assembly. The instrument can include a drill, such as a right-angle drill in one aspect. The method includes maneuvering the instrument relative to the implant recipient site. This maneuvering can be performed to drill or cut out a predetermined shape for receiving an implant, such as a round implant having an elastic articulating surface.

The instrument guide assembly is configured to pivot such that the instrument is at least partially rotatable while attached to the instrument guide assembly. The first receptacle is configured to limit movement of a terminal end of the instrument. The first guide tool portion can include a second receptacle configured to engage a protrusion on the instrument. Based on this arrangement, the instrument is limited in its movement by at least three different interfaces.

Although a drill is illustrated in some Figures of this disclosure, one of ordinary skill in the art would understand that any type of instrument could be used in conjunction with the various guide assemblies and features.

Having thus described the presently preferred embodiments in detail, it is to be appreciated and will be apparent to those skilled in the art that many physical changes, only a few of which are exemplified in the detailed description, could be made without altering the inventive concepts and principles embodied therein. It is also to be appreciated that numerous embodiments incorporating only part of the preferred embodiment are possible which do not alter, with respect to those parts, the inventive concepts and principles embodied therein.

The present embodiments and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

What is claimed is:

1. A surgical tool assembly comprising:
a first guide tool portion configured to support an instrument, wherein the first guide tool portion is configured to limit movement of the instrument relative to a patient site; and
a second guide tool portion configured to receive at least one K-wire to stabilize the surgical tool assembly;
wherein the first guide tool portion further comprises an instrument guide assembly configured to engage with a portion of the instrument, and
wherein the instrument guide assembly comprises a slider that is slidably secured along a track defined by a base portion of the first guide tool portion, and a support interface configured to engage with the portion of the instrument, wherein the support interface is configured to pivot relative to the slider.

2. The surgical tool assembly according to claim 1, wherein the first guide tool portion further comprises a guide arm including an end defining a first receptacle, wherein the end is configured to engage against the patient site, the first receptacle is configured to constrict movement of an end of the instrument relative to the patient site, and the track has a length that is greater than a diameter of the first receptacle.

3. The surgical tool assembly according to claim 1, wherein the first guide tool portion further comprises a first support guide defining a plurality of openings each configured to receive at least one K-wire.

4. The surgical tool assembly according to claim 3, wherein the at least one K-wire is configured to be received in the first support guide and the second guide tool portion are configured to be arranged at an oblique angle relative to each other.

5. The surgical tool assembly according to claim 1, wherein the first guide tool portion and the second guide tool portion are adjustable relative to each other.

6. The surgical tool assembly according to claim 1, wherein the second guide tool portion is configured to support a cannula dimensioned to receive the at least one K-wire, and the cannula is configured to engage against a patient's anatomy.

7. A surgical tool assembly comprising:
a first guide tool portion configured to support an instrument, wherein the first guide tool portion is configured to limit movement of the instrument relative to a patient site; and
a second guide tool portion configured to receive at least one K-wire to stabilize the surgical tool assembly;
wherein the first guide tool portion further comprises a guide arm including an end defining a first receptacle, wherein the end is configured to engage against the patient site, and the first receptacle is configured to constrict movement of an end of the instrument relative to the patient site; and
wherein the end of the guide arm is coated with a hydrogel or soft durometer polymer.

8. The surgical tool assembly according to claim 7, wherein the guide arm is configured to extend in a tangential direction relative to the patient site.

9. The surgical tool assembly according to claim 7, wherein the first guide tool portion further comprises a second receptacle configured to receive another portion of the instrument.

10. The surgical tool assembly according to claim 9, wherein the instrument includes a protrusion configured to project within the second receptacle.

11. A surgical tool assembly comprising:

a first guide tool portion configured to support an instrument, wherein the first guide tool portion is configured to limit movement of the instrument relative to a patient site;

a second guide tool portion configured to receive at least one K-wire to stabilize the surgical tool assembly; and an instrument guide configured to receive a terminal end of instrument, wherein the instrument guide is configured to be engaged by the at least one K-wire received within the second guide tool portion.

12. A method of engaging an instrument with an implant recipient site using a surgical tool assembly, the method comprising:

providing a first guide tool portion comprising an instrument guide assembly and a guide arm defining a first receptacle, and a second guide tool portion configured to receive a K-wire;

aligning the first receptacle with the implant recipient site;

stabilizing the surgical tool assembly via insertion of at least one K-wire through at least one of the first guide tool portion or the second guide tool portion;

attaching an instrument to the instrument guide assembly; and maneuvering the instrument relative to the implant recipient site.

13. The method according to claim 12, wherein the instrument guide assembly is configured to pivot such that the instrument is at least partially rotatable while attached to the instrument guide assembly, the first receptacle is configured to limit movement of a terminal end of the instrument, and the first guide tool portion further comprises a second receptacle configured to engage a protrusion on the instrument.

14. The method according to claim 12, wherein at least two K-wires extend through the first guide tool portion and at least one K-wire extends through the second guide tool portion to stabilize the surgical tool assembly.

15. A method of installing an implant in a patient recipient site, the method comprising:

arranging a first instrument relative to the patient recipient site to confirm initial characteristics of the patient recipient site and inserting a K-wire through the first instrument into a patient's anatomy;

arranging a second instrument around the first instrument and removing the first instrument;

inserting a cutting tool inside of the second instrument and into engagement with the patient recipient site, wherein the cutting tool has an outer circumferential cutting profile that is less than an outer circumferential profile of the implant, and the cutting tool is configured to remove bone debris from the patient recipient site;

inserting a third instrument into the patient recipient site to determine characteristics of the patient recipient site after removing bone debris from the patient recipient site; and installing the implant into the patient recipient site using a fourth instrument, wherein the fourth instrument includes a rim configured to engage a peripheral sidewall of the implant.

\* \* \* \* \*